US011813132B2

(12) United States Patent
Pesach et al.

(10) Patent No.: US 11,813,132 B2
(45) Date of Patent: Nov. 14, 2023

(54) DENTAL DEVICE WITH PROBE

(71) Applicant: Dentlytec G.P.L. LTD., Tel-Aviv (IL)

(72) Inventors: Benny Pesach, Rosh Haayin (IL);
Amitai Reuvenny, Kfar-Saba (IL);
Blanc Zach Lehr, Tel-Aviv (IL); Ygael Grad, Tel-Aviv (IL)

(73) Assignee: DENTLYTEC G.P.L. LTD., Tel-Aviv (IL)

( * ) Notice: Subject to any disclaimer, the term of this patent is extended or adjusted under 35 U.S.C. 154(b) by 624 days.

(21) Appl. No.: 16/628,656

(22) PCT Filed: Jul. 4, 2018

(86) PCT No.: PCT/IL2018/050731
§ 371 (c)(1),
(2) Date: Jan. 3, 2020

(87) PCT Pub. No.: WO2019/008586
PCT Pub. Date: Jan. 10, 2019

(65) Prior Publication Data
US 2020/0155285 A1 May 21, 2020

Related U.S. Application Data

(60) Provisional application No. 62/528,496, filed on Jul. 4, 2017.

(51) Int. Cl.
*A61C 17/20* (2006.01)
*A61B 1/00* (2006.01)
(Continued)

(52) U.S. Cl.
CPC .......... *A61C 17/20* (2013.01); *A61B 1/00193* (2013.01); *A61B 1/24* (2013.01);
(Continued)

(58) Field of Classification Search
CPC ...... A61C 17/20; A61C 9/0053; A61B 5/0088; A61B 5/4547; A61B 5/0066; A61B 8/4488
See application file for complete search history.

(56) References Cited

U.S. PATENT DOCUMENTS

| 3,634,938 A | 1/1972 | Hutchinson |
| 4,279,598 A | 7/1981 | Scheicher |

(Continued)

FOREIGN PATENT DOCUMENTS

| CN | 101677757 A | 3/2010 |
| EP | 2165674 A1 | 3/2010 |

(Continued)

OTHER PUBLICATIONS

Invitation to Pay Additional Fees Dated May 12, 2020 From the International Searching Authority Re. Application No. PCT/IL2020/050040. (3 Pages).

(Continued)

*Primary Examiner* — Oommen Jacob
(74) *Attorney, Agent, or Firm* — COOLEY LLP

(57) ABSTRACT

An intra oral scanner (IOS) including a probe is disclosed. Optionally, the probe is calibrated to measure locations at a higher accuracy than the IOS. For example, the probe may be used to locate points in a 3D map at high precision and/or the points used to increase the precision of location of other points and/or surfaces in the map. In some embodiments, the probe includes a sensor. Optionally, the probe may be used to measure locations that are hard to view with the IOS. For example, the IOS probe combination may be used to produce 3D maps of a recess in a tooth and/or gums and/or a periodontal pocket and/or to traduce a 3D map or periodontal disease. In some embodiments the probe may be used to measure physical properties, for example, the IOS probe (Continued)

combination may be used to produce a 3D image of hardness of mucosa.

11 Claims, 29 Drawing Sheets

(51) Int. Cl.
- A61B 1/24 (2006.01)
- A61B 5/00 (2006.01)
- A61B 8/12 (2006.01)
- A61B 8/00 (2006.01)
- A61C 17/02 (2006.01)
- B06B 1/06 (2006.01)

(52) U.S. Cl.
CPC .......... *A61B 5/0066* (2013.01); *A61B 5/0088* (2013.01); *A61B 5/4547* (2013.01); *A61B 8/12* (2013.01); *A61B 8/4488* (2013.01); *A61B 8/4494* (2013.01); *A61C 17/0202* (2013.01); *B06B 1/0607* (2013.01)

(56) References Cited

U.S. PATENT DOCUMENTS

| | | |
|---|---|---|
| 4,478,580 A | 10/1984 | Barrut |
| 4,571,180 A | 2/1986 | Kulick |
| 4,665,621 A | 5/1987 | Ackerman et al. |
| 4,764,114 A | 8/1988 | Jeffcoat et al. |
| 4,790,751 A | 12/1988 | Reinhardt et al. |
| 4,823,809 A | 4/1989 | Gott, Jr. et al. |
| 4,873,651 A | 10/1989 | Raviv |
| 4,883,425 A | 11/1989 | Zimble |
| 4,935,635 A | 6/1990 | O'Harra |
| 5,049,070 A | 9/1991 | Ademovic |
| 5,051,823 A | 9/1991 | Cooper et al. |
| 5,176,687 A | 1/1993 | Hasson et al. |
| 5,178,536 A | 1/1993 | Werly et al. |
| 5,178,537 A | 1/1993 | Currie |
| 5,190,456 A * | 3/1993 | Hasegawa ............... B06B 1/186 433/118 |
| 5,215,521 A | 6/1993 | Cochran et al. |
| 5,224,049 A | 6/1993 | Mushabac |
| 5,230,621 A * | 7/1993 | Jacoby ................... A61B 1/015 433/29 |
| 5,244,387 A | 9/1993 | Fuierer |
| 5,257,184 A | 10/1993 | Mushabac |
| 5,313,053 A | 5/1994 | Koenck et al. |
| 5,318,442 A | 6/1994 | Jeffcoat et al. |
| 5,320,462 A | 6/1994 | Johansson et al. |
| 5,368,597 A | 11/1994 | Pagedas |
| 5,372,502 A | 12/1994 | Massen et al. |
| 5,423,677 A | 6/1995 | Brattesani |
| 5,435,722 A | 7/1995 | Mandell |
| 5,618,296 A | 4/1997 | Sorensen et al. |
| 5,634,790 A | 6/1997 | Pathmanabhan et al. |
| 5,743,731 A | 4/1998 | Lares et al. |
| 5,850,289 A | 12/1998 | Fowler et al. |
| 5,862,559 A | 1/1999 | Hunter |
| 5,897,509 A | 4/1999 | Toda et al. |
| 5,919,129 A | 7/1999 | Vandre |
| 5,944,523 A | 8/1999 | Badoz |
| 5,969,321 A | 10/1999 | Danielson et al. |
| 5,993,209 A | 11/1999 | Matoba et al. |
| 6,000,939 A | 12/1999 | Ray et al. |
| 6,007,333 A | 12/1999 | Callan et al. |
| 6,116,899 A | 6/2000 | Takeuchi |
| 6,142,936 A | 11/2000 | Beane et al. |
| 6,179,611 B1 | 1/2001 | Everett et al. |
| 6,257,889 B1 | 7/2001 | Boston |
| 6,276,934 B1 | 8/2001 | Rakocz |
| 6,309,219 B1 | 10/2001 | Robert |
| 6,406,440 B1 | 6/2002 | Stefanchik |
| 6,468,079 B1 | 10/2002 | Fischer et al. |
| 6,819,318 B1 | 11/2004 | Geng |
| 6,885,464 B1 | 4/2005 | Pfeiffer et al. |
| 7,041,056 B2 | 5/2006 | Deslauriers et al. |
| 7,056,329 B2 | 6/2006 | Kerr |
| 7,346,417 B2 | 3/2008 | Lueth et al. |
| 7,494,338 B2 | 2/2009 | Durbin et al. |
| 7,625,335 B2 | 12/2009 | Deichmann et al. |
| 7,668,583 B2 | 2/2010 | Fegert et al. |
| 7,813,591 B2 | 10/2010 | Paley et al. |
| 8,280,152 B2 | 10/2012 | Thiel et al. |
| 8,371,848 B2 | 2/2013 | Okawa et al. |
| 8,439,682 B1 | 5/2013 | Heath et al. |
| 8,744,194 B2 | 6/2014 | Kawasaki et al. |
| 8,936,470 B2 | 1/2015 | Pruckner et al. |
| 9,137,511 B1 | 9/2015 | LeGrand, III et al. |
| 9,179,987 B2 | 11/2015 | Goodacre |
| 9,463,081 B2 | 10/2016 | Urakabe |
| 9,522,054 B2 | 12/2016 | Kim et al. |
| 9,603,675 B2 | 3/2017 | Pruckner |
| 9,918,805 B2 | 3/2018 | Pruckner |
| 10,136,970 B2 | 11/2018 | Pesach |
| 10,299,880 B2 | 5/2019 | Ramirez Luna et al. |
| 10,470,846 B2 | 11/2019 | Kopelman et al. |
| 10,695,150 B2 | 6/2020 | Kopelman et al. |
| 2002/0037490 A1 | 3/2002 | Oyamada et al. |
| 2002/0103420 A1 | 8/2002 | Coleman et al. |
| 2002/0133096 A1 | 9/2002 | Toda et al. |
| 2004/0087937 A1 | 5/2004 | Eggers et al. |
| 2004/0097792 A1 | 5/2004 | Moll et al. |
| 2004/0106868 A1 | 6/2004 | Liew et al. |
| 2004/0117052 A1 | 6/2004 | Geng |
| 2004/0158261 A1 | 8/2004 | Vu |
| 2004/0191725 A1 | 9/2004 | Szymaitis |
| 2005/0116673 A1 | 6/2005 | Carl et al. |
| 2006/0085005 A1 | 4/2006 | Kenealy et al. |
| 2006/0154198 A1 | 7/2006 | Durbin et al. |
| 2007/0037125 A1 | 2/2007 | Maev et al. |
| 2007/0042315 A1 | 2/2007 | Boutoussov et al. |
| 2007/0064242 A1 | 3/2007 | Childers |
| 2007/0065782 A1 * | 3/2007 | Maschke ................... A61C 3/00 433/224 |
| 2007/0172112 A1 | 7/2007 | Paley et al. |
| 2007/0225744 A1 | 9/2007 | Nobles et al. |
| 2007/0260231 A1 | 11/2007 | Rose et al. |
| 2008/0002011 A1 | 1/2008 | Mizutani et al. |
| 2008/0002869 A1 | 1/2008 | Scharlack et al. |
| 2008/0038688 A1 | 2/2008 | Kopelman et al. |
| 2008/0145817 A1 | 6/2008 | Brennan et al. |
| 2008/0160477 A1 | 7/2008 | Stookey et al. |
| 2008/0201101 A1 | 8/2008 | Hebert et al. |
| 2008/0234579 A1 * | 9/2008 | Halevy-Politch .... A61B 8/0875 73/627 |
| 2008/0255498 A1 * | 10/2008 | Houle ................. A61C 17/0208 604/20 |
| 2008/0261165 A1 | 10/2008 | Steingart et al. |
| 2009/0017416 A1 | 1/2009 | Nguyen et al. |
| 2009/0043314 A1 | 2/2009 | Sevensson et al. |
| 2009/0061383 A1 | 3/2009 | Kang |
| 2009/0087050 A1 | 4/2009 | Gandyra |
| 2009/0306506 A1 | 12/2009 | Heger et al. |
| 2009/0326383 A1 | 12/2009 | Barnes et al. |
| 2010/0047733 A1 | 2/2010 | Nahlieli |
| 2010/0092908 A1 | 4/2010 | Rothenwaender et al. |
| 2010/0189341 A1 | 7/2010 | Oota et al. |
| 2010/0238279 A1 | 9/2010 | Thoms et al. |
| 2010/0239136 A1 | 9/2010 | Gandyra et al. |
| 2010/0239996 A1 | 9/2010 | Ertl |
| 2010/0268069 A1 | 10/2010 | Liang |
| 2010/0268071 A1 | 10/2010 | Kim |
| 2010/0305435 A1 | 12/2010 | Magill |
| 2011/0190781 A1 | 8/2011 | Collier et al. |
| 2011/0301419 A1 | 12/2011 | Craft et al. |
| 2012/0015329 A1 | 1/2012 | Gross et al. |
| 2012/0040305 A1 * | 2/2012 | Karazivan .......... A61B 1/00087 433/29 |
| 2012/0046536 A1 | 2/2012 | Cheung et al. |
| 2012/0062557 A1 | 3/2012 | Dillon et al. |
| 2012/0097002 A1 | 4/2012 | Thiedig |
| 2012/0179281 A1 | 7/2012 | Steingart et al. |

(56) References Cited

U.S. PATENT DOCUMENTS

| | | |
|---|---|---|
| 2012/0189182 A1 | 7/2012 | Liang et al. |
| 2012/0270177 A1 | 10/2012 | Nakashima et al. |
| 2012/0271176 A1 | 10/2012 | Moghaddam et al. |
| 2013/0000666 A1 | 1/2013 | Hu |
| 2013/0017507 A1 | 1/2013 | Moffson et al. |
| 2013/0027515 A1 | 1/2013 | Vinther et al. |
| 2013/0060144 A1* | 3/2013 | Culjat ............... A61B 8/14 600/459 |
| 2013/0188012 A1 | 7/2013 | Bellis et al. |
| 2013/0209953 A1 | 8/2013 | Arlinsky et al. |
| 2013/0253278 A1 | 9/2013 | Smith |
| 2013/0273492 A1 | 10/2013 | Suttin, Sr. et al. |
| 2014/0066784 A1 | 3/2014 | Yokota |
| 2014/0093835 A1 | 4/2014 | Levin |
| 2014/0111616 A1 | 4/2014 | Blayvas |
| 2014/0120492 A1 | 5/2014 | Ioannidis et al. |
| 2014/0120493 A1 | 5/2014 | Levin |
| 2014/0146142 A1 | 5/2014 | Duret et al. |
| 2014/0178832 A1 | 6/2014 | Choi et al. |
| 2014/0194696 A1 | 7/2014 | Fischvogt |
| 2014/0199650 A1 | 7/2014 | Moffson et al. |
| 2014/0221819 A1 | 8/2014 | Sarment |
| 2014/0276055 A1 | 8/2014 | Barthe et al. |
| 2014/0248577 A1 | 9/2014 | Tahmasebi et al. |
| 2014/0309523 A1 | 10/2014 | Daon et al. |
| 2014/0330285 A1 | 11/2014 | Rosenblatt et al. |
| 2014/0343395 A1 | 11/2014 | Choi et al. |
| 2015/0015701 A1 | 1/2015 | Yu |
| 2015/0118638 A1 | 4/2015 | Cowburn |
| 2015/0182299 A1 | 7/2015 | Koubi et al. |
| 2015/0223910 A1 | 8/2015 | Pruckner |
| 2015/0223916 A1 | 8/2015 | Kim et al. |
| 2015/0229911 A1 | 8/2015 | Ge et al. |
| 2015/0297254 A1 | 11/2015 | Sullivan et al. |
| 2015/0348320 A1 | 12/2015 | Pesach et al. |
| 2016/0120615 A1 | 5/2016 | Scurtescu |
| 2016/0163115 A1* | 6/2016 | Furst ............... G06T 7/344 433/29 |
| 2016/0259515 A1 | 9/2016 | Sabina et al. |
| 2016/0262856 A1 | 9/2016 | Atiya et al. |
| 2016/0270878 A1 | 9/2016 | Fulton, III |
| 2016/0338682 A1 | 11/2016 | Hoyle et al. |
| 2016/0338803 A1 | 11/2016 | Pesach |
| 2017/0007377 A1* | 1/2017 | Pesach ............... A61C 19/04 |
| 2017/0202483 A1 | 7/2017 | Sorimoto et al. |
| 2018/0360481 A1 | 12/2018 | Bonadio et al. |
| 2019/0125297 A1* | 5/2019 | Chan ............... A61C 9/0086 |
| 2019/0192262 A1 | 6/2019 | Pesach |
| 2019/0247033 A1 | 8/2019 | Yaari |
| 2019/0262098 A1 | 8/2019 | Pesach et al. |
| 2019/0343598 A1 | 11/2019 | Knobel et al. |
| 2020/0060550 A1 | 2/2020 | Pesach et al. |
| 2020/0155285 A1 | 5/2020 | Pesach et al. |
| 2020/0268410 A1 | 8/2020 | Yaari et al. |
| 2022/0071737 A1 | 3/2022 | Pesach et al. |

FOREIGN PATENT DOCUMENTS

| | | |
|---|---|---|
| EP | 2630929 A2 | 8/2013 |
| EP | 1901033 B1 | 1/2018 |
| ES | 2115544 A1 | 6/1998 |
| FR | 2692773 A1 | 12/1993 |
| GB | 2495522 A | 4/2013 |
| JP | 63-005742 A | 1/1988 |
| JP | 07-155297 A | 6/1995 |
| JP | 10-165425 A | 6/1998 |
| JP | H10-262996 A | 10/1998 |
| JP | 11-192207 A | 7/1999 |
| JP | 2002-125927 A | 5/2002 |
| JP | 2003-325451 A | 11/2003 |
| JP | 2006-102497 A | 4/2006 |
| JP | 2007-152004 A | 6/2007 |
| JP | 2007-296249 A | 11/2007 |
| JP | 2009-268614 A | 11/2009 |
| JP | 2010-104652 A | 5/2010 |
| JP | 2012-016573 A | 1/2012 |
| JP | 5016311 B2 | 6/2012 |
| JP | 2014-236957 A | 12/2014 |
| JP | 5661255 B2 | 1/2015 |
| KR | 10-1782740 B1 | 9/2017 |
| WO | WO 98/06352 A1 | 2/1998 |
| WO | WO 2005/104959 A1 | 11/2005 |
| WO | WO 2007/063980 A1 | 6/2007 |
| WO | WO 2008/013181 A1 | 1/2008 |
| WO | WO 2014/020247 A1 | 2/2014 |
| WO | WO 2014/102779 A2 | 7/2014 |
| WO | WO 2015/028646 A1 | 3/2015 |
| WO | WO 2015/107520 A1 | 7/2015 |
| WO | WO 2016/028789 A2 | 2/2016 |
| WO | WO 2016/064617 A1 | 4/2016 |
| WO | WO 2016/110855 A1 | 7/2016 |
| WO | WO 2016/113745 A1 | 7/2016 |
| WO | 2016178212 A1 | 11/2016 |
| WO | WO 2016/178212 A1 | 11/2016 |
| WO | WO 2017/125926 A2 | 7/2017 |
| WO | WO 2017/216803 A1 | 12/2017 |
| WO | WO 2018/047180 A1 | 8/2018 |
| WO | WO 2019/008586 A1 | 1/2019 |
| WO | WO 2019/021285 A1 | 1/2019 |
| WO | WO 2019/049152 A1 | 3/2019 |
| WO | WO 2020/144692 A2 | 7/2020 |

OTHER PUBLICATIONS

Official Action dated Jun. 12, 2020 from the US Patent and Trademark Office Re. U.S. Appl. No. 16/634,152. (41 pages).
Search Report and Written Opinion prepared for International Application No. PCT/IL2018/050731, dated Oct. 1, 2018.
Official Action dated Apr. 3, 2020 from the US Patent and Trademark Office Re. U.S. Appl. No. 16/199,954. (31 pages).
Official Action dated May 15, 2020 from the US Patent and Trademark Office Re. U.S. Appl. No. 16/071,058. (31 pages).
Official Action dated Feb. 19, 2021 From the US Patent and Trademark Office Re. U.S. Appl. No. 16/227,995. (27 Pages).
Final Official Action dated Dec. 28, 2020 from the US Patent and Trademark Office Re. U.S. Appl. No. 16/634,152. (29 pages).
Communication Pursuant to Article 94(3) EPC dated Nov. 19, 2020 From the European Patent Office Re. Application No. 13830124.7. (6 Pages).
Official Action dated Nov. 4, 2020 From the US Patent and Trademark Office Re. U.S. Appl. No. 15/274,756. (19 Pages).
Decision of Rejection dated Jan. 14, 2020 From the Japan Patent Office Re. Application No. 2017-228103 and Its Translation Into English. (7 Pages).
Summons to Attend Oral Proceedings Pursuant to Rule 115(1) EPC Dated Mar. 19, 2020 From the European Patent Office Re. Application No. 13830124.7. (13 Pages).
Notice of Allowance dated Jul. 13, 2021 from the US Patent and Trademark Office Re. U.S. Appl. No. 16/227,995. (7 pages).
International Search Report and the Written Opinion dated Jul. 23, 2020 From the International Searching Authority Re. Application No. PCT/IL2020/050040. (14 Pages).
Applicant-Initiated Interview Summary dated Aug. 2, 2017 From the US Patent and Trademark Office Re. U.S. Appl. No. 15/115,196. (3 pages).
Communication Pursuant to Article 94(3) EPC dated Aug. 10, 2017 From the European Patent Office Re. Application No. 13830124.7. (6 Pages).
Communication Pursuant to Article 94(3) EPC dated Nov. 19, 2018 From the European Patent Office Re. Application No. 13830124.7. (8 Pages).
Communication Relating to the Results of the Partial International Search and the Provisional Opinion dated Jun. 14, 2017 From the International Searching Authority Re. Application No. PCT/IL2017/050072. (12 Pages).
Communication Relating to the Results of the Partial International Search dated May 8, 2014 From the International Searching Authority Re. Application No. PCT/IL2013/051059. (7 Pages).

(56) References Cited

OTHER PUBLICATIONS

European Search Report and the European Search Opinion dated Feb. 4, 2020 From the European Patent Office Re. Application 19211372.8. (10 Pages).
International Preliminary Report on Patentability dated Aug. 2, 2018 From the International Bureau of WIPO Re. Application No. PCT/IL2017/050072. (10 Pages).
International Preliminary Report on Patentability dated Feb. 6, 2020 From the International Bureau of WIPO Re. Application No. PCT/IL2018/050825. (10 Pages).
International Preliminary Report on Patentability dated Jul. 9, 2015 From the International Bureau of WIPO Re. Application No. PCT/IL2013/051059. (17 Pages).
International Preliminary Report on Patentability dated Jan. 16, 2020 From the International Bureau of WIPO Re. Application No. PCT/IL2018/050731. (9 Pages).
International Preliminary Report on Patentability dated Nov. 16, 2017 From the International Bureau of WIPO Re. Application No. PCT/IL2016/050449. (11 Pages).
International Preliminary Report on Patentability dated Jul. 20, 2017 From the International Bureau of WIPO Re. Application No. PCT/IL2016/050023. (10 Pages).
International Preliminary Report on Patentability dated Jul. 27, 2017 From the International Bureau of WIPO Re. Application No. PCT/IL2016/050058. (7 Pages).
International Search Report and the Written Opinion dated Oct. 1, 2018 From the International Searching Authority Re. Application No. PCT/IL2018/050731. (16 Pages).
International Search Report and the Written Opinion dated Sep. 2, 2014 From the International Searching Authority Re. Application No. PCT/IL2013/051059. (22 Pages).
International Search Report and the Written Opinion dated Nov. 7, 2018 From the International Searching Authority Re. Application No. PCT/IL2018/050825. (17 Pages).
International Search Report and the Written Opinion dated Aug. 8, 2017 From the International Searching Authority Re. Application No. PCT/IL2017/050072. (17 Pages).
International Search Report and the Written Opinion dated Apr. 18, 2016 From the International Searching Authority Re. Application No. PCT/IL2016/050058. (12 Pages).
International Search Report and the Written Opinion dated Apr. 21, 2016 From the International Searching Authority Re. Application No. PCT/IL2016/050023. (14 Pages).
International Search Report and the Written Opinion dated Aug. 23, 2016 From the International Searching Authority Re. Application No. PCT/IL2016/050449. (19 Pages).
Notice Of Allowance dated Aug. 9, 2018 From the US Patent and Trademark Office Re. U.S. Appl. No. 15/571,231. (17 pages).
Notice Of Allowance dated May 12, 2016 From the US Patent and Trademark Office Re. U.S. Appl. No. 14/655,286. (16 Pages).
Notice of Reasons for Rejection dated May 7, 2019 From the Japan Patent Office Re. Application No. 2017-228103 and Its Translation Into English. (8 Pages).
Notice of Reasons for Rejection dated Jul. 11, 2017 From the Japan Patent Office Re. Application No. 2015-548888 and Its Translation Into English. (5 Pages).
Notice of Reasons for Rejection dated Feb. 14, 2017 From the Japan Patent Office Re. Application No. 2015-548888 and Its Translation Into English. (10 Pages).
Notice of Reasons for Rejection dated Sep. 25, 2018 From the Japan Patent Office Re. Application No. 2017-228103 and Its Translation Into English. (15 Pages).
Notice Requesting Submission of Opinion dated Jan. 21, 2020 From the Korean Intellectual Property Office Re. Application No. 10-2019-7034814. (3 Pages).
Notice Requesting Submission of Opinion dated Apr. 26, 2019 From the Korean Intellectual Property Office Re. Application No. 10-2015-7020305. (4 Pages).
Notification of Office Action and Search Report dated Jan. 5, 2017 From the State Intellectual Property Office of the People's Republic of China Re. Application No. 201380071840.0. (7 Pages).
Notification of Office Action dated Apr. 15, 2016 From the State Intellectual Property Office of the People's Republic of China Re. Application No. 201380071840.0. (3 Pages).
Office Action dated Aug. 6, 2019 From the Israel Patent Office Re. Application No. 264237 and Its Translation Into English. (6 Pages).
Official Action dated Mar. 9, 2017 From the US Patent and Trademark Office Re. U.S. Appl. No. 15/115,196. (26 pages).
Official Action dated Dec. 13, 2017 From the US Patent and Trademark Office Re. U.S. Appl. No. 15/115,196. (26 pages).
Official Action dated Jun. 13, 2019 From the US Patent and Trademark Office Re. U.S. Appl. No. 15/274,756. (39 pages).
Official Action dated Sep. 28, 2016 From the US Patent and Trademark Office Re. U.S. Appl. No. 15/115,196. (19 pages).
Requisition by the Examiner Dated Oct. 4, 2019 From the Innovation, Science and Economic Development Canada, Canadian Intellectual Property Office Re. Application No. 2,896,210. (3 Pages).
Restriction Official Action dated Nov. 14, 2019 From the US Patent and Trademark Office Re. U.S. Appl. No. 16/199,954. (6 pages).
Restriction Official Action dated Sep. 26, 2018 From the US Patent and Trademark Office Re. U.S. Appl. No. 15/274,756. (10 pages).
Supplementary European Search Report and the European Search Opinion dated Aug. 21, 2018 From the European Patent Office Re. Application No. 16789407.0. (6 Pages).
Translation Dated Feb. 2, 2020 of Notice Requesting Submission of Opinion dated Jan. 21, 2020 From the Korean Intellectual Property Office Re. Application No. 10-2019-7034814. (3 Pages).
Translation Dated May 9, 2019 of Notice Requesting Submission of Opinion dated Apr. 26, 2019 From the Korean Intellectual Property Office Re. Application No. 10-2015-7020305. (4 Pages).
Translation of Notification of Apr. 15, 2016 From the State Intellectual Property Office of the People's Republic of China Re. Application No. 201380071840.0. (2 Pages).
Translation of Notification of Office Action dated Jan. 5, 2017 From the State Intellectual Property Office of the People's Republic of China Re. Application No. 201380071840.0. (4 Pages).
Bouguet et al. "3D Photography Using Shadows in Dual-Space Geometry", The International Journal of Computer Vision, 35(2): 129-149, Nov./Dec. 1999.
Fluegge et al. "Precision of Intraoral Digital Dental Impressions With iTero and Extraoral Digitization With the iTero and A Model Scanner", American Journal of Orthodontics and Dentofacial Orthopedics, 144(3): 471-478, Sep. 2013.
Geng "Structured-Light 3D Surface Imaging: A Tutorial", Advances in Optics and Photonics, 3: 128-160, 2011.
Goshtasby et al. "A System for Digital Reconstruction of Gypsum Dental Casts", IEEE Transactions On Medical Imaging, 16(5): Oct. 1997.
Logozzo et al. "Recent Advances in Dental Optics—Part I: 3D Intraoral Scanners for Restorative Dentistry", Optics and Lasers in Engineering, 54: 203-221, Mar. 2014.
Maintz et al. "A Survey of Medical Image Registration", Medical Image Analysis, 2(1): 1-36, Mar. 1998.
Medeiros et al. "Coded Structred Light for 3D-Photography: An Overview", IEEE-RITA, (Latin-American Learning Technologies Journal), IV(2): 109-124, Jul. 1999.
OmniVision "OVM6946 400x400. Compact, Cost-Effective Wafer-Level Camera Module for Single-Use Endoscopes", OmniVision, Product Brief, 2 P., Aug. 10, 2016.
Paperno et al. "A New Method for Magnetic Position and Orientation Tracking", IEEE Transactions on Magnetics, XP011033696, 37(4): 1938-1940, Jul. 2001.
Salvi et al. "Pattern Codification Strategies in Structured Light Systems", Pattern Recognition, 37(4): 827-849, 2004.
Savarese et al. "3D Reconstruction by Shadow Carving: Theory and Practical Evaluation", International Journal of Computer Vision, 71(3): 305-336, Published Online Jun. 1, 2006.
Toshiba "IK-CT2: 0.7 x 0.7 mm, 220x220, CMOS", Toshiba Information Systems, Product Sheet, 1 P., Dec. 2016.

(56) References Cited

OTHER PUBLICATIONS

Notice Requesting Submission of Opinion dated Feb. 3, 2021 From the Korean Intellectual Property Office Re. Application No. 10-2020-7032325 and Its Translation Into English. (14 Pages).
Supplementary European Search Report and the European Search Opinion dated Aug. 24, 2022 From the European Patent Office Re. Application No. 20739036.0. (9 Pages).
Communication Pursuant to Article 94(3) EPC dated Jan. 18, 2023 from the European Patent Office Re. Application No. 19211372.8 (7 Pages).
Restriction Official Action dated Dec. 27, 2022 from the US Patent and Trademark Office Re. U.S. Appl. No. 17/211,640. (4 pages).
Supplementary European Search Report and the European Search Opinion dated Feb. 2, 2023 from the European Patent Office Re. Application No. 22207979.0 (7 Pages).
Communication Pursuant to Article 94(3) EPC dated Oct. 5, 2021 From the European Patent Office Re. Application No. 18759184.7. (6 Pages).
Communication Pursuant to Article 94(3) EPC dated Oct. 7, 2020 From the European Patent Office Re. Application No. 177805300.6. (5 Pages).
Communication Pursuant to Article 94(3) EPC dated Nov. 16, 2021 From the European Patent Office Re. Application No. 17707964.7. (4 Pages).
Communication Pursuant to Article 94(3) EPC dated Jan. 29, 2021 From the European Patent Office Re. Application No. 18769813.9. (9 Pages).
Communication Pursuant to Article 94(3) EPC dated Nov. 30, 2021 From the European Patent Office Re. Application No. 17780530.6. (4 Pages).
Communication Pursuant to Article 94(3) EPC dated Jan. 31, 2020 From the European Patent Office Re. Application No. 17780530.6. (3 Pages).
English Translation Dated Nov. 30, 2021 of Ground(s) of Reason of Rejection dated Nov. 19, 2021 From the Korean Intellectual Property Office Re. Application No. 2010-7032325. (2 Pages).
European Search Report and the European Search Opinion dated Jan. 3, 2022 From the European Patent Office Re. Application No. 21200149.9. (10 Pages).
Ground(s) of Reason of Rejection dated Nov. 19, 2021 From the Korean Intellectual Property Office Re. Application No. 2010-7032325. (2 Pages).
International Preliminary Report on Patentability dated Mar. 19, 2020 From the International Bureau of WIPO Re. Application No. PCT/IL2017/051014. (10 Pages).
International Preliminary Report on Patentability dated Mar. 21, 2019 From the International Bureau of WIPO Re. Application No. PCT/IL2017/051015. (13 Pages).

International Preliminary Report on Patentability dated Jul. 22, 2021 From the International Bureau of WIPO Re. Application No. PCT/IL2020/050040. (10 Pages).
International Search Report and the Written Opinion dated Dec. 11, 2018 From the International Searching Authority Re. Application No. PCT/IL2017/051014. (18 Pages).
International Search Report and the Written Opinion dated Jan. 24, 2018 From the International Searching Authority Re. Application No. PCT/IL2017/051015. (23 Pages).
Invitation to Pay Additional Fees, Communication Relating to the Results of the Partial International Search and the Provisional Opinion dated Nov. 17, 2017 From the International Searching Authority Re. Application No. PCT/IL2017/051015. (17 Pages).
Official Action dated Sep. 3, 2021 from the US Patent and Trademark Office Re. U.S. Appl. No. 16/634,152. (43 pages).
Summons to Attend Oral Proceedings Pursuant to Rule 115(1) EPC Dated Mar. 18, 2022 From the European Patent Office Re. Application No. 18769813.9. (9 Pages).
Summons to Attend Oral Proceedings Pursuant to Rule 115(1) EPC Dated Mar. 19, 2021 From the European Patent Office Re. Application No. 17780530.6. (7 Pages).
Summons to Attend Oral Proceedings Pursuant to Rule 115(1) EPC Dated Apr. 20, 2021 From the European Patent Office Re. Application No. 17780530.6. (2 Pages).
Supplementary European Search Report and the European Search Opinion dated Feb. 19, 2021 From the European Patent Office Re. Application No. 18837606.5. (7 Pages).
Translation Dated Nov. 30, 2021 of Ground(s) of Reason of Rejection dated Nov. 19, 2021 From the Korean Intellectual Property Office Re. Application No. 2010-7032325. (2 Pages).
Communication Pursuant to Article 94(3) EPC dated Jul. 1, 2022 From the European Patent Office Re. Application No. 18837606.5. (4 Pages).
Official Action dated Oct. 26, 2022 from the US Patent and Trademark Office Re. U.S. Appl. No. 16/634,152. (15 pages).
Final Official Action dated Nov. 9, 2021 from US Patent and Trademark Office Re. U.S. Appl. No. 15/274,756. (15 pages).
Notice of Allowance dated Nov. 9, 2022 from the US Patent and Trademark Office Re. U.S. Appl. No. 15/274,756. (8 pages).
Official Action dated Jun. 17, 2021 from the US Patent and Trademark Office Re. U.S. Appl. No. 15/274,756. (16 pages).
Official Action dated Jul. 20, 2022 from US Patent and Trademark Office Re. U.S. Appl. No. 15/274,756. (25 pages).
Requisition by the Examiner Dated Apr. 7, 2021 From the Innovation, Science and Economic Development Canada, Canadian Intellectual Property Office Re. Application No. 2,896,210. (16 Pages).
Notice of Allowance dated Feb. 13, 2023 from the US Patent and Trademark Office Re. U.S. Appl. No. 16/634,152, 11 pages.

\* cited by examiner

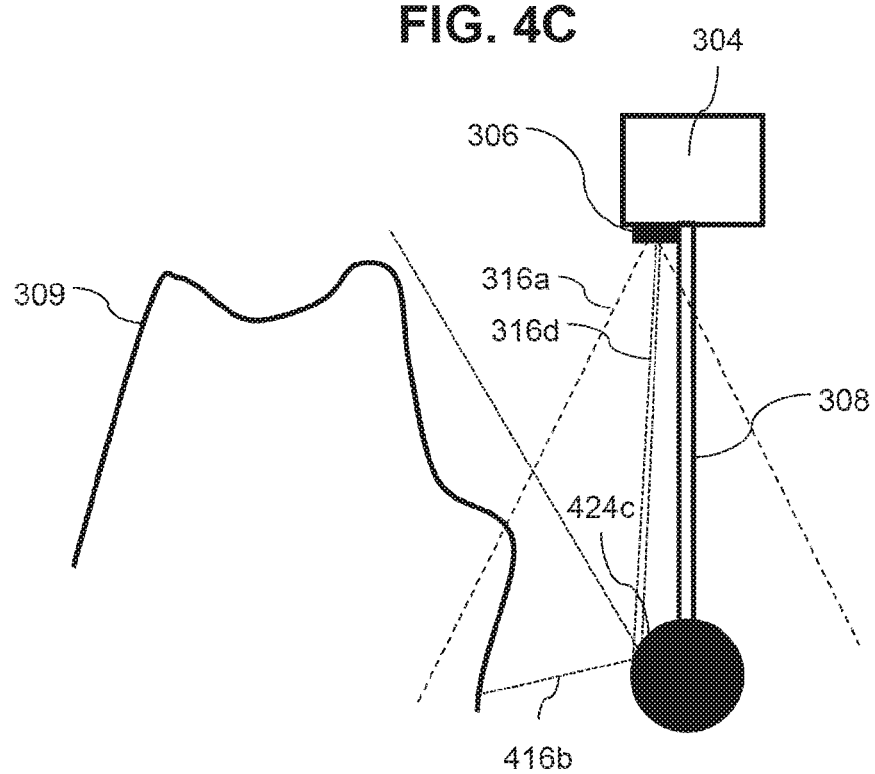

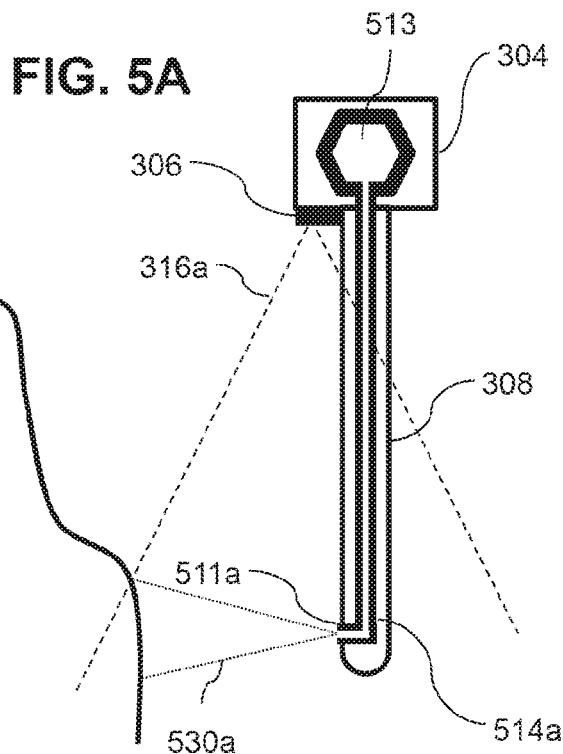
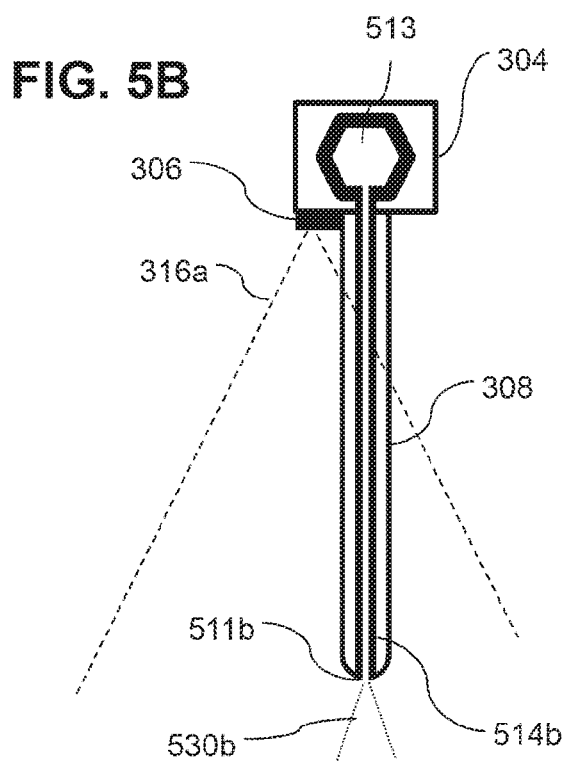

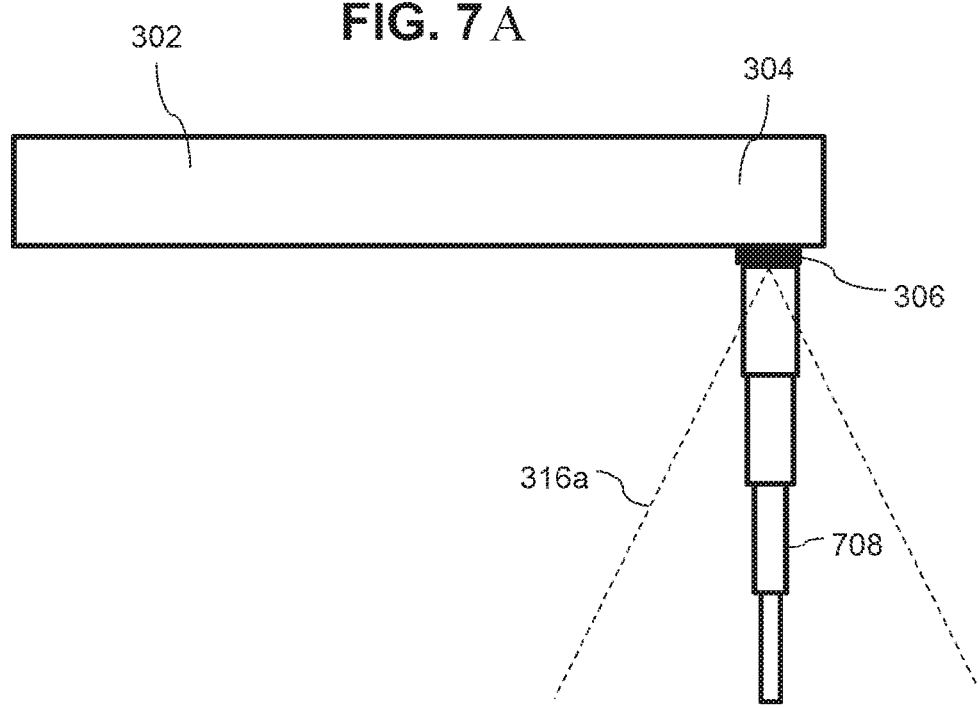

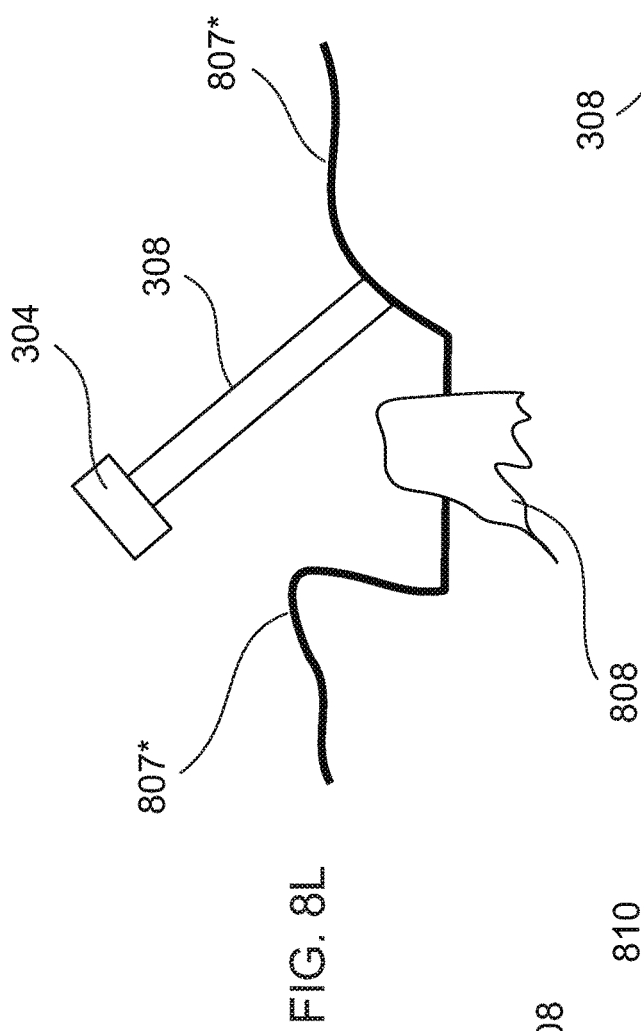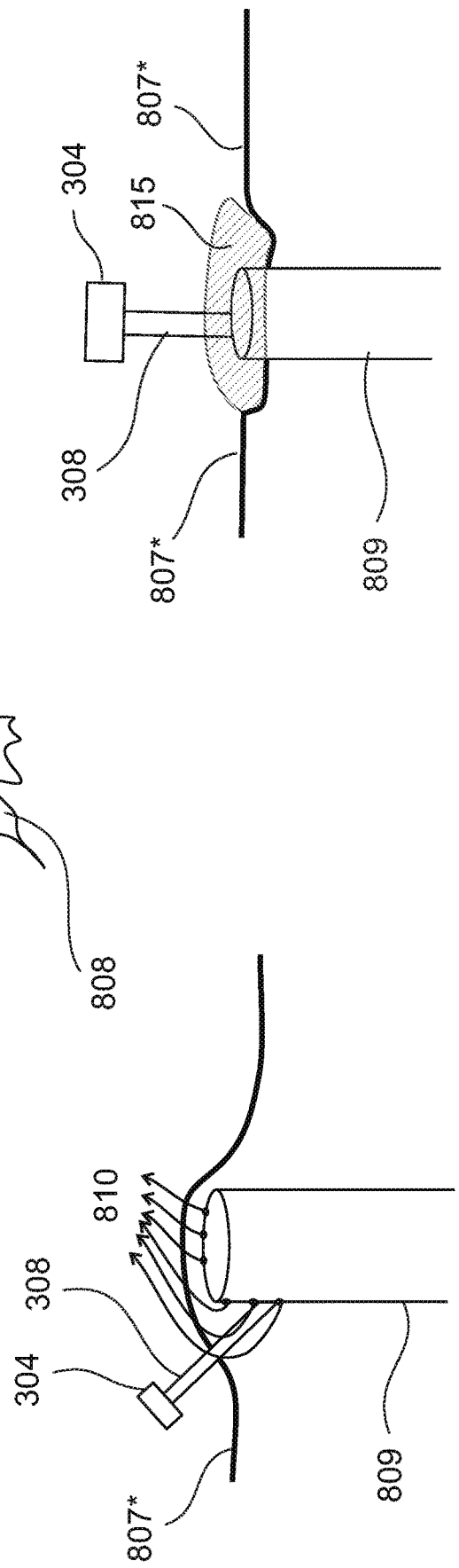

DENTAL DEVICE WITH PROBE

RELATED APPLICATION/S

This application is a National Phase of PCT application No. PCT/IL2018/050731 having International filing date of 4 Jul. 2018, which claims the benefit of and priority to U.S. Provisional Application No. 62/528,496 filed on 4 Jul. 2017.

The contents of all of the above applications are incorporated by reference as if fully set forth herein.

FIELD AND BACKGROUND OF THE INVENTION

The present invention, in some embodiments thereof, relates to a dental probe, optionally provided as part of or an attachment for an intra oral scanner (IOS) and/or optionally providing imaging or sensing or other functionality.

SUMMARY OF THE INVENTION

According to an aspect of some embodiments of the invention, there is provided a method of making oral measurements, including: providing an IOS with an elongate probe extending therefrom; contacting a plurality of points inside the oral cavity with the probe, while scanning the cavity with the IOS; and determining a position of each of the plurality of points from the scanning, using the IOS scanning to determine a position in space of the elongate probe.

According to some embodiments of the invention, the accuracy of the determined position is more accurate than the position accuracy of point locations obtained by the IOS without the probe.

According to some embodiments of the invention, the method further includes: calculating a location of a surface using the determined positions.

According to some embodiments of the invention, the method further includes: calculating a measurement of a length using the determined positions.

According to some embodiments of the invention, the method further includes: calculating a position of a curved plane using the determined positions.

According to some embodiments of the invention, the determining includes determining positions of the points relative to each other.

According to some embodiments of the invention, the determining includes determining positions of the points relative to an oral feature.

According to some embodiments of the invention, the contacting includes contacting natural tissue.

According to some embodiments of the invention, the contacting includes contacting within a recess in the body.

According to some embodiments of the invention, the recess includes one of a socket of a tooth extraction, an excavated hole or groove or cavity in a bone, a drilled hole in a tooth, an excavated cavity in a tooth for an inlay, an excavated cavity in a tooth for an onlay, a grinding area in a tooth and a root of a tooth.

According to some embodiments of the invention, the method according further includes determining position of points which are located on areas which are difficult to be determined using IOS including at least one of a steep wall, an interproximal wall with a narrow interproximal gap, optionally a gap smaller or equal to than 2 mm, a negative slope wall, a high reflectivity surface, a high absorbance surfaces, an obscured surface and a surface inside a recess.

According to some embodiments of the invention, the contacting includes contacting at least one point which is located on an area which is difficult to determined using IOS including at least one of a steep wall, an interproximal wall with a narrow interproximal gap, a negative slope wall, a high reflectivity surface, a high absorbance surfaces, an obscured surface and a surface inside a recess.

According to some embodiments of the invention, the recess is naturally formed or artificially formed in a bone, gum and/or a tooth.

According to some embodiments of the invention, the contacting includes contacting gum or other mucosal tissue.

According to some embodiments of the invention, the contacting includes inserting the probe through mucosal tissue to contact an underlying hard structure.

According to some embodiments of the invention, the contacting includes contacting gum is used for measuring gums thickness by comparing obtained 3D model to bone location in a CT 3D model.

According to some embodiments of the invention, the method includes measuring bone for an implant.

According to some embodiments of the invention, the contacting includes contacting tooth tissue.

According to some embodiments of the invention, the method includes measuring tooth abrasion or gaps between opposing teeth when a mouth is closed.

According to some embodiments of the invention, the method includes measuring gaps between opposing teeth when closed, for accurate closure mapping.

According to some embodiments of the invention, the method includes measuring a horizontal or vertical mismatch of a crown.

According to some embodiments of the invention, the method includes measuring the joint between a crown and a tooth to which it is attached.

According to some embodiments of the invention, the method includes measuring a tooth prepared for fitting of a crown.

According to some embodiments of the invention, the method includes estimating a mechanical or biomechanical property of the mechanical tissue by the contacting.

According to some embodiments of the invention, the mechanical property is one of tissue elasticity and tissue hardness.

According to some embodiments of the invention, the contacting includes contacting one or more artificially provided oral items.

According to some embodiments of the invention, the oral item includes a crown, a denture or an implant, brackets, laminates, esthetic elements, night guards, splints, surgical stents.

According to some embodiments of the invention, the method includes measuring a same intra-oral portion using the determining and the scanning, and improving an accuracy of a representation by the scanning using the determined positions.

According to some embodiments of the invention, the method includes using the scanning to generate a 3D reconstruction of an oral surface and identifying on the reconstruction one or more locations with a reduced accuracy and improving the accuracy using the determined positions.

According to an aspect of some embodiments of the invention, there is provided an iOS scanner, including: a body having a head; at least one imager suitable for intraoral scanning from the head; and a hollow probe with an opening, the probe extending from the head and within a field of view of the at least one imager.

According to some embodiments of the invention, the scanner includes a channel extending from the probe to a source of pressurized material suitable for flowing through the channel and the probe to the opening.

According to some embodiments of the invention, the source includes water, abrasive material or adhesive.

According to some embodiments of the invention, the scanner includes a channel extending from the probe to a source of negative pressure.

According to some embodiments of the invention, the channel contains an optical fiber.

According to some embodiments of the invention, the fiber is coupled to a light source suitable for one or more of ablation, coagulation, tissue cutting, illumination and sending via the fiber.

According to some embodiments of the invention, the channel contains an electrical signal conductor.

According to some embodiments of the invention, the probe includes a tip and the IOS is used for determining a locations of the tip during a procedure.

According to some embodiments of the invention, the opening is on a side of the hollow probe.

According to some embodiments of the invention, the opening is at a distal end of the hollow probe and facing along an axis of the probe.

According to an aspect of some embodiments of the invention, there is provided a dental probe, including: a body having a head and a long dimension; at least one imager suitable for imaging in a lateral direction from the head; and a probe extending in a lateral direction from the head and within a field of view of the imager and including a side viewer.

According to some embodiments of the invention, the side-viewer includes a mirror which reflects light from a lateral direction towards the body with distortion low enough for imaging.

According to some embodiments of the invention, the viewer includes an ultrasonic distance sensor.

According to some embodiments of the invention, the viewer includes an ultrasonic imager.

According to some embodiments of the invention, the body (probe) includes a side viewing ultrasonic imager (IVUS).

According to some embodiments of the invention, the body (probe) includes a Piezoelectric Micromachined Ultrasound Transducer (PMUT) array.

According to some embodiments of the invention, the body includes a channel for dispensing acoustic coupling liquid.

According to some embodiments of the invention, the viewer includes an optical imager.

According to some embodiments of the invention, the viewer includes a 3D imager.

According to some embodiments of the invention, the viewer includes side viewing OCT or interference imager or sensor.

According to some embodiments of the invention, the body includes a plurality of mechanical contact sensors.

According to some embodiments of the invention, the side viewer includes a plurality of sensors, wherein a preferred sensor can be chosen according to local clinical conditions.

According to some embodiments of the invention, the local clinical condition includes at least one of bleeding, fluids, gums, biotype of the gums, flexibility, finish line coverage.

According to some embodiments of the invention, probe includes ultrasonic scaler, and where the imager is configured to determine if all the plaque was removed.

According to an aspect of some embodiments of the invention, there is provided an iOS scanner, including: a body having a head; at least one imager suitable for intra-oral scanning; and a probe designed for easy replacement.

In some embodiments the probe is detachably connected to the IOS body or to the IOS head, with a connection designed for quick release. In some embodiments the quick release is optionally performed using a tool. In some embodiments the quick release is optionally performed using a tool typically found in a dentist tool kit, by way of a non-limiting example using forceps.

According to an aspect of some embodiments of the invention, there is provided an iOS scanner, including: a body having a head; at least one imager suitable for intra-oral scanning; and a probe designed for easy movement along an intra-oral surface.

In some embodiments the probe includes a tip with a ball at the tip, potentially implementing a rolling ball tip. In some embodiments the ball is a stainless steel ball, or a plastic ball constructed of phenolics, acetals, Teflon (PTFE), ultra high molecular weight polyethylene (UHMWPE), and/or nylon.

In some embodiments the probe includes a tip shaped for easy movement along an intra-oral surface. In some embodiments the tip of the probe is rounded.

In some embodiments the probe includes a tip including a material selected for easy movement along an intra-oral surface. In some embodiments the tip of the probe includes stainless steel, or a plastic such as phenolics, acetals, Teflon (PTFE), ultra high molecular weight polyethylene (UHMWPE), and/or nylon.

According to an aspect of some embodiments of the invention, there are provided method for using an iOS scanner and a probe for producing a model of insides of a mouth.

In some embodiments gingiva is optionally scanned, and a three dimensional shape of gingiva is optionally calculated. In some embodiments a three-dimensional (3D) model is optionally produced.

In some embodiments an abutment is optionally scanned. In some embodiments the abutment is scanned inside the oral cavity. In some embodiments the abutment is scanned separately from a scan of the oral cavity.

In some embodiments the 3D model is made to combine a model of the oral cavity and a model of the abutment.

In some embodiments the 3D model is optionally used to design a custom abutment, which is optionally shaped according to the gingiva shape.

In some embodiments the 3D model is optionally used to measure parameters of a dental implant. The parameters optionally include a location of a dental implant within an oral cavity, an orientation of the dental implant, a shape of the dental implant, and similar geometric parameters, optionally relative to adjacent teeth and/or relative to a jaw bone and/or relative to gums.

In some embodiments the measurement is optionally done using a number of known point locations on an implant or in the oral cavity.

In some embodiments the measurement is optionally done using a known location of the probe or of a tip of the probe relative to the scanner. In some embodiments the location of the probe or of the tip of the probe relative to the scanner is optionally saved during scanning. By way of a non-limiting example, replacement probes may optionally have different shapes and/or sizes, and scanning the probes provides known locations based on knowing shapes and/or sizes of the probes.

In some embodiments the number of points is selected to enable determining a specific shape of an implant which are enough to determine the parameters due to the implant's shape.

In some embodiments measurement of the implant is optionally done even in presence of blood covering some or all of the implant, for example after implant insertion into bone or after opening covering gingiva to expose the implant.

In some embodiments detection and/or location and/or measurement of the implant is optionally performed using a metal detecting component in the IOS device and/or the probe.

In some embodiments measurement or measurements are made of a hole or holes in the oral cavity. In some embodiments the measurement(s) include one or more of depth, width, diameter, shape and inside threading of the hole(s).

In some embodiments the measurement(s) are optionally made by inserting the probe into the hole.

According to an aspect of some embodiments of the present invention there is provided an oral measuring method configured to make oral measurement within the oral cavity of a patient including providing an Intra Oral Scanner (IOS) with an elongate probe extending therefrom, contacting a plurality of first points inside an oral cavity with the probe while scanning the cavity with the IOS, and determining a position of each of the plurality of first points based on the scanning to determine a position in space of the elongate probe.

According to some embodiments of the invention, further including calculating at least one of a location of a surface using the determined positions, a measurement of a length using the determined positions, and a position of a curved plane using the determined positions.

According to some embodiments of the invention, the determining includes determining positions of the points relative to an oral feature.

According to some embodiments of the invention, further including using the probe to collect data on periodontal health, producing a 3D model of the oral cavity, and automatically generating a periodontal chart.

According to some embodiments of the invention, further including using the elongate body to measure periodontal pocket depth, automatically generating a personalized periodontal chart that includes at least one of a map of clinical attachment level, a location of a cement to enamel junction, a mucogingival line, a periodontal conditions, an area of decay, a tooth cavity, a missing tooth, a depth of a gum pocket, a bleeding point discovered during probing, gum recession, an abnormality in a tooth, a 2D image of a tooth, and a 3D image of a tooth.

According to some embodiments of the invention, the contacting includes contacting within a recess of a tissue(s), a tooth(teeth), and a bone(s) within or proximate to the oral cavity.

According to some embodiments of the invention, the contacting includes contacting within a recess, and wherein the recess includes one of a socket of a tooth extraction, an excavated hole in a bone, a drilled hole in a tooth, an excavated cavity in a tooth for an inlay, an excavated cavity in a tooth for an onlay, and a root of a tooth.

According to some embodiments of the invention, further including determining a position of second points which are located on at least one of a steep wall, an interproximal wall with a narrow interproximal gap, a negative slope wall, a high reflectivity surface, a high absorbance surfaces, an obscured surface and a surface inside a recess.

According to some embodiments of the invention, the contacting includes contacting at least one point which is located on at least one of a steep wall, an interproximal wall with a narrow interproximal gap, a negative slope wall, a high reflectivity surface, a high absorbance surfaces, an obscured surface and a surface inside a recess.

According to some embodiments of the invention, the first plurality of points include gum or other mucosal tissue.

According to some embodiments of the invention, the contacting includes inserting the probe through mucosal tissue to contact an underlying tooth, implant or bone structure.

According to some embodiments of the invention, the plurality of first points include gum tissue, and wherein the method further includes determining gum thickness by creating a 3D model based on the determining step and comparing the 3D model to bone location in a CT 3D model.

According to some embodiments of the invention, the plurality of first points include points on tooth tissue.

According to some embodiments of the invention, further including measuring at least one of tooth abrasion and gaps between opposing teeth when a mouth is closed based upon the positions of the plurality of first points.

According to some embodiments of the invention, further including measuring a horizontal or vertical mismatch of a crown based upon the positions of the plurality of first points.

According to some embodiments of the invention, further including measuring the joint between a crown and a tooth to which it is attached based upon the positions of the plurality of first points.

According to some embodiments of the invention, further including measuring a tooth prepared for fitting of a crown based upon the positions of the plurality of first points.

According to some embodiments of the invention, further including estimating a mechanical property of a mechanical tissue by the contacting.

According to some embodiments of the invention, the mechanical property is at least one of tissue elasticity and tissue hardness.

According to some embodiments of the invention, the plurality of points includes points along artificially provided oral items.

According to some embodiments of the invention, the oral item includes a crown, a denture or an implant, brackets, laminates, esthetic elements, night guards, splints.

According to some embodiments of the invention, further including conducting a secondary scanning and determining positions of the first plurality of points so as to determine a refined determined position of the first plurality of points.

According to some embodiments of the invention, further including using the scanning to generate a 3D reconstruction of an oral surface, and identifying, on the reconstruction, one or more locations of one or more of the plurality of first positions having reduced accuracy.

According to an aspect of some embodiments of the present invention there is provided an IOS scanner, including a body having a head, at least one imager suitable for intra-oral scanning from the head, and a hollow probe with an opening, the probe extending from the head and within a field of view of the at least one imager.

According to some embodiments of the invention, further including a channel extending from the probe to a source of pressurized material suitable for flowing through the channel and the probe to the opening.

According to some embodiments of the invention, the source includes water, abrasive material or adhesive.

According to some embodiments of the invention, including a channel extending from the probe to a source of negative pressure.

According to some embodiments of the invention, including a channel extending from the probe to the opening, wherein the channel contains an optical fiber.

According to some embodiments of the invention, the fiber is coupled to a light source suitable for one or more of ablation, coagulation, tissue cutting, illumination and sending via the fiber.

According to some embodiments of the invention, including a channel extending from the probe to the opening, wherein the channel contains an electrical signal conductor.

According to some embodiments of the invention, the probe includes a tip and the IOS is configured for determining a location of the tip during a procedure.

According to some embodiments of the invention, the opening is on a side of the hollow probe.

According to some embodiments of the invention, the opening is at a distal end of the hollow probe and facing along an axis of the probe.

According to an aspect of some embodiments of the present invention there is provided a dental probe, including a body having a head, the body elongated in a first direction, at least one imager configured for imaging in a second direction different from the first direction, and a probe extending in the second direction and within a field of view of the imager and including a viewer.

According to some embodiments of the invention, the probe is configured for quick release from the body.

According to some embodiments of the invention, the quick release is configured for releasing using a standard dentist tool.

According to some embodiments of the invention, the viewer includes a mirror which reflects light towards the body with distortion low enough for imaging.

According to some embodiments of the invention, the viewer includes an ultrasonic distance sensor.

According to some embodiments of the invention, the viewer includes an ultrasonic imager.

According to some embodiments of the invention, the body (probe) includes a side viewing ultrasonic imager (IVUS).

According to some embodiments of the invention, the body (probe) includes a Piezoelectric Micromachined Ultrasound Transducer (PMUT) array.

According to some embodiments of the invention, the body includes a channel for dispensing acoustic coupling liquid.

According to some embodiments of the invention, the viewer includes an optical imager.

According to some embodiments of the invention, the viewer includes a 3D imager.

According to some embodiments of the invention, the viewer includes side viewing OCT or interference imager or sensor.

According to some embodiments of the invention, the body includes a mechanical contact sensor.

According to some embodiments of the invention, the viewer includes a plurality of sensors, wherein a preferred sensor can be chosen according to local clinical conditions.

According to some embodiments of the invention, a tip of the probe includes at least one of a structure and a material configured for gliding along a surface when the tip contacts the surface with limited to negligible friction.

According to some embodiments of the invention, a tip of the probe includes a ball for rolling along a surface when the tip contacts the surface.

According to some embodiments of the invention, wherein, probe includes an ultrasonic scaler, and where the imager is configured to determine if plaque was removed.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as 3D reconstruction, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4C are schematic showings of IOS including a laterally extending probe having a reflector in a field of view of the IOS, in accordance with some embodiments of the invention;

FIGS. 5A-5B are schematics showings of IOS including a laterally extending probe having a channel therein, in accordance with some embodiments of the invention;

FIG. 7A is a schematic showing of IOS including a telescopic probe, in accordance with some embodiments of the invention;

FIG. 8L is a simplified illustration of an IOS measuring gingiva surrounding a dental implant in accordance with some embodiments of the invention;

FIGS. 8M and 8N are simplified illustrations of an IOS measuring parameters of a dental implant in accordance with some embodiments of the invention;

DESCRIPTION OF SPECIFIC EMBODIMENTS OF THE INVENTION

Figure 1A:
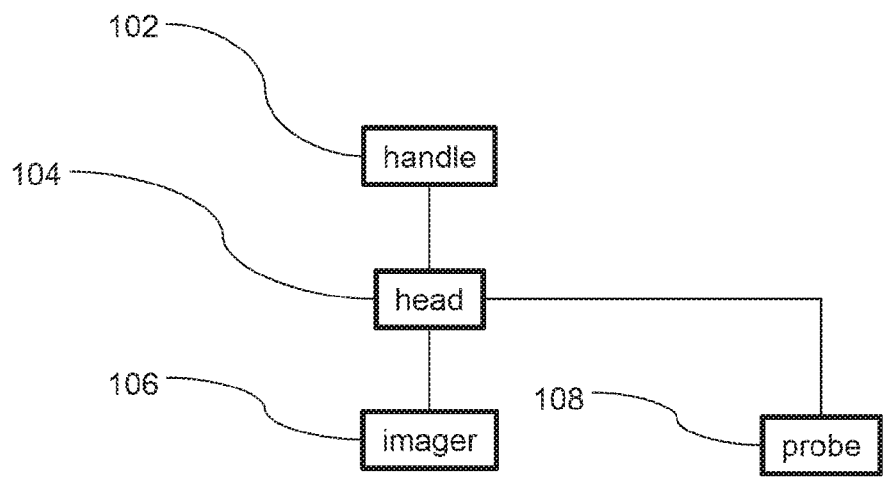
FIG. 1A is a block diagram showing of an IOS including a laterally extending probe, in accordance with some embodiments of the invention.

The present invention, in some embodiments thereof, relates to a dental probe, optionally provided as part of or an attachment for an intra oral scanner (IOS) and/or optionally providing imaging or sensing or other functionality.

An aspect of some embodiments of the invention relates to an IOS with a laterally extending probe, integral or add-on. In some exemplary embodiments of the invention, the probe is within a field of view of the IOS imager. In some exemplary embodiments of the invention, the probe is used to contact an intraoral surface for providing geometrical or other measurement thereof. In some exemplary embodiments of the invention, a mapping by the IOS is improved by said contact. Optionally or alternatively, the probe contact is used to detect surface properties other than geometry relative to the IOS, for example, tissue stiffness.

In some embodiments, a probe may have an average width (e.g. diameter) ranging between 0.1 to 0.5 mm and/or between 0.5 to 1.0 mm and/or between 1 to 2 mm and/or between 2 to 4 mm.

In some exemplary embodiments of the invention, the probe is used to measure one or more of a tooth extraction socket, a drilled socket, a soft tissue surface, a bone surface under soft tissue, a dental implant, a tooth, space between teeth, periodontal pocket, a sub-gingival section of a tooth, a dental abrasion pattern and or a recess in a tooth. Optionally, the measured space is measurable using the IOS, and the probe provides enhanced resolution. Optionally or alternatively, the probe is used to measure surfaces that are not measurable using the IOS, for example, due to field of view limitations thereof.

In some exemplary embodiments of the invention, the probe laterally extends, for example, at an angle of between 30 and 150 degrees relative to an axis of a handle of the IOS.

In some exemplary embodiments of the invention, the probe includes an imager, for example, an ultrasound imager (for example a side viewing ultrasonic imager (IVUS) or a Piezoelectric Micromachined Ultrasound Transducer (PMUT) array)), a sensor, for example, an ultrasound sensor or stain sensor and/or a mirror, for example, reflecting a view lateral to the probe to an imager of the IOS.

In some exemplary embodiments of the invention, the probe includes an effector, for example, a tool for tissue ablation or coagulation.

In some exemplary embodiments of the invention, the probe includes a channel, for example, for providing a fluid or removing fluid. Optionally, the channel is connected to a reservoir and/or a source, for example, of cement or sterilizing fluid. In some embodiments a channel may have an average cross sectional area along the probe ranging between 0.01 mm$^2$ to 0.1 mm$^2$ and/or between 0.1 mm$^2$ to 0.25 mm$^2$ and/or between 0.25 mm$^2$ to 1. mm$^2$ and/or between 1 mm$^2$ to 25 mm$^2$. Optionally the channel may take up between 1% to 10% and/or between 10% to 30% and/or between 30% to 60% and/or between 60% to 90% of the probe.

In some embodiments, IOS location measurement uncertainty will be reduced by between 50 to 90%. For example an IOS scanner may have a measurement error of less than 40 μm and/or a location of a feature at a probe tip may be measured with an error of less than 10 μm and/or 5 μm and/or less than 2 μm. One or more points of high accuracy measurements may be used to condition measurements in other locations to decrease measurement uncertainty in regions of the domain where the probe tip was not used for a direct measurement. For example, conditioning on accurately measured points, the error in a region may be reduced to below 5 μm and/or below 10 μm and/or below 20 μm and/or below 30 μm. For example, conditioning may be used to improve the accuracy of a depth mapped image.

An aspect of some embodiments of the invention relates to measurement of intraoral surfaces using an IOS having a laterally extending probe. In some exemplary embodiments of the invention, the probe tip is atraumatic. Optionally, the IOS is used to position the probe in a 3D representation of the oral cavity or apportion thereof.

In some exemplary embodiments of the invention, the IOS is used to measure one or more of mucosa, artificial objects (on their own, relative to each other, orientation, and/or relative to natural tissues and/or natural objects of various types), shapes of cavities (e.g., natural, artificial or resulting from tissue extraction), implant shapes, prosthesis shapes, shapes of surfaces that mate with prostheses (e.g., for bone onlay and/or supra-contact).

In some exemplary embodiments of the invention, measurement is used to determine one or more of teeth closure, abrasion patterns, plaque, post crown inaccuracy and/or root apex depth.

In some exemplary embodiments of the invention, the probe tip penetrates the gums and can be used to measure gum thickness by comparing pre- and post-penetration positions.

In some exemplary embodiments of the invention, the probe tip is used to sense non-geometrical properties, for example, elasticity (e.g., using a strain sensor) and/or color (e.g., using an optical detector). In some embodiments, the probe will be used to exert pressure on an object. Optionally, the IOS may collect data about the movement of the object and/or tissue and/or teeth due to forces exerted by the probe.

An aspect of some embodiments of the invention relates to measurement of intraoral surfaces using both IOS-based photometrics and using contact measurement. Optionally, the two measurements are combined to yield a higher accuracy, for example, a better resolution and/or better coverage of areas difficult to measure using only photometrics. Alternatively or additionally, a probe may include a fiducial marker. Optionally, a probe tip may include a sensor.

For example the probe tip may include an imager and/or a linear measurement sensor (for example a laser range finder and/or an ultrasound range finder). Optionally the probe tip sensor may augment IOS measurements in areas that are difficult to measure with a conventional IOS sensor, for example, inside a recess and/or between teeth and/or in an area angled away from the sensor and/or in an obscured area.

In some exemplary embodiments of the invention, a same measurement tool is used both intraorally and on objects outside of the mouth, for example, a yet-to-be deployed prosthesis.

In some exemplary embodiments of the invention, intraoral features are used to identify a location in a model or an image or a scan of a mouth.

In some exemplary embodiments of the invention, a location of a probe connected to the IOS is used to identify a location in a model or an image or a scan of a mouth relative to the IOS.

In some exemplary embodiments of the invention, a tip of a probe connected to the IOS is used to identify a location in a model or an image or a scan of a mouth relative to the IOS.

An aspect of some embodiments of the invention relates to augmenting an IOS with tools for treating tissue and/or assisting in dental treatment. In some exemplary embodiments of the invention, the IOS includes a laterally extending probe which includes one or more longitudinal channels for passage of materials to, from and/or within the intraoral cavity and optionally having an opening at the side and/or tip of the probe. For example, one or more of water, abrasive materials, adhesive materials, and/or filler materials may be provided via such a channel. Optionally or alternatively, the channel is connected to a suction source for material removal.

In some exemplary embodiments of the invention, such a channel includes an optical fiber for providing therapeutic and/or imaging light.

An aspect of some embodiments of the invention relates to an IOS having a laterally extending probe which supports side viewing. In some exemplary embodiments of the invention, the probe includes a mirror which reflects light towards an IOS imager component. Optionally or alternatively, the probe includes one or more optical or ultrasonic sensor or imager. Optionally, the imager is a 3D imager and/or software for reconstructing a 3D image form moving imagers is provided at a control station. Optionally a sensor may include an optical coherence tomography OCT system, for example to image areas below the surface of tissue.

An aspect of some embodiments of the invention relates to a probe may be used in evaluation and/or treatment of periodontal conditions. For example, a probe may be used to measure periodontal pocket depths. Alternatively or additionally, a probe with a sensor may be used to measure a periodontal condition. For example, the probe and/or the sensor may be inserted into a periodontal pocket. For example, the sensor may sense color. For example, a sensor may be used to identify a cemental enamel junction and/or bleeding and/or inflammation. Alternatively or additionally a probe may include a source of ultraviolet light and/or measure fluorescence, for example, to measure subgingival plaque.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary IOS with Laterally Extending Probe

Referring now to the drawings, FIG. 1A is a block diagram showing of an IOS including a laterally extending probe, in accordance with some embodiments of the invention. In some embodiment the probe includes an IOS imager 106 mounted on a head 104 of the device. For example head 104 may be mounted on a handle 102. Optionally, a laterally extending probe 108 is attached to head 104. In some embodiments, the tip of probe 108 is in the field of view (FOV) of imager 106 (for example in FIG. 1B a probe 108' is shown in a FOV 116 of an imager 106'). Optionally, the 3D position of the tip of probe 108 with respect to imager may be known to a high accuracy. Alternatively or additionally, the tip of probe 108 may include a fiducial marker. For example, markings on probe 108 and/or a size of the tip may be used in estimating location and/or distance to an object and/or size of the object. For example, the size and/or position of the tip of probe 108 may be known with an error of less than 5 μm.

In some embodiments, a probe may be made of stainless steel and/or another metal and/or plastic. Optionally the tip of the probe may be sharp. Alternatively or additionally, the tip may be rounded and/or blunt and/or include a widening. For example the widening may have width between 1 to 5 mm and/or between 5 to 10 mm and/or between 10 to 20 mm and/or between 20 to 30 mm.

In some embodiments, an IOS may include a handle. For example, the handle may be easily griped for example having a width of between 0.5 cm to 5 cm. Optionally, head 104 is sized for movement inside a mouth, for example a human mouth. Optionally the head has dimensions between 0.5 to 3 cm. For example, a user may manipulate handle 102 to scan the mouth with head 104 and/or probe 108.

In some embodiments, imager 106 has a high enough resolution to produce depth mapped images and/or an STL file mapping 3D features of an oral cavity with an error of less than 30 μm and/or less than 100 μm and/or less than 10 μm. Optionally, imager 106 includes a light source. For example, the light source may include a structured light and/or a coherent light.

In some embodiments, probe 108 is used to increase the accuracy of an IOS image and/or a STL mapping made from the image. Alternatively or additionally, having probe 108 on a scanner may save time of a dentist by facilitating producing an IOS scan while the dentist probes, checks and/or treats dental conditions. Optionally, the IOS will produce a hard record of the procedure. For example, the record may be used for evaluating and/or training of dentists. Additionally or alternatively, the record may be useful to as evidence in cases of malpractice and/or for evaluating the efficacy of interventions and/or improvements therein. Additionally or alternatively, the record may be used to evaluate progress of a procedure and/or condition and/or plan follow up. Alternatively or additionally, probe 108 may have functions that improve imaging, for example of difficult to sight surfaces (for example smooth and/or low reflectivity surfaces and/or surfaces that are obscured and/or located in a position which is difficult to reach at a good imaging pose).

Figure 1B:
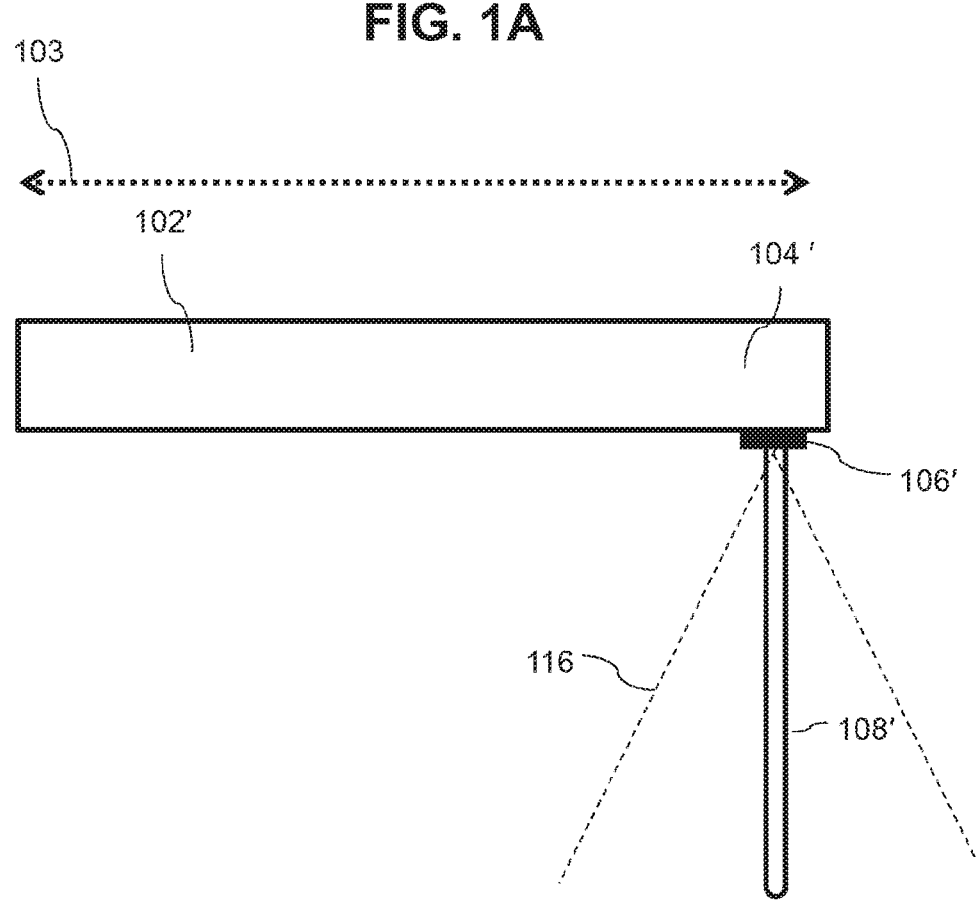
FIG. 1B is a schematic showing of an IOS including a laterally extending probe, in accordance with some embodiments of the invention.

FIG. 1B is a schematic diagram showing of an IOS including a laterally extending probe 108', in accordance with some embodiments of the invention. For example, a handle 102' and a head 104' may have a long axis 103. Optionally probe 108' is straight. Alternatively or additionally, a probe may be curved. For example, probe 108' is mounted perpendicular to axis 103. Alternatively or additionally, probe 108' is mounted at an angle between 45 to 135 degrees to axis 103.

Figure 2A:
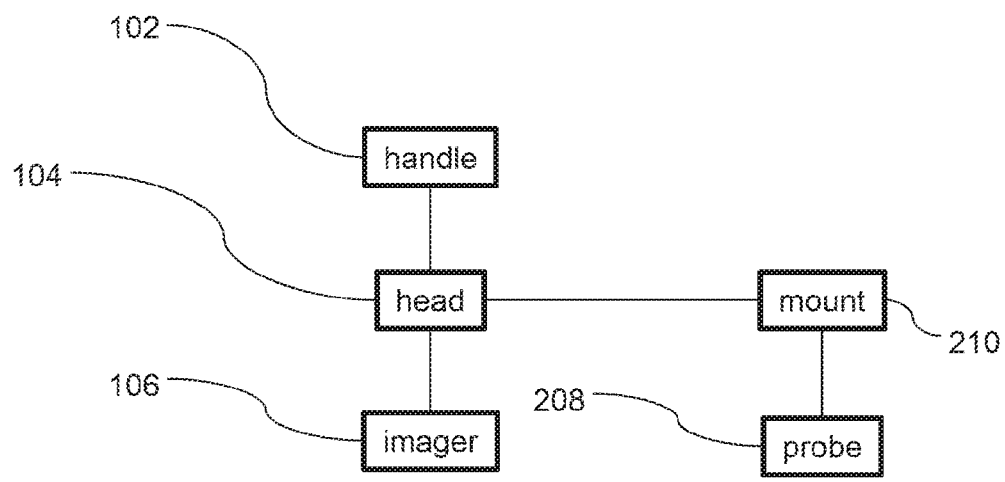
FIG. 2A is a block diagram of an IOS having a probe attachment mounted thereon, in accordance with some exemplary embodiments of the invention.

FIG. 2A is a block diagram showing of an IOS having a probe attachment mounted thereon, in accordance with some exemplary embodiments of the invention. In some embodiments, an IOS scanner may include a mount 210 for attaching a probe attachment 208. For example, mount 210 may include a snap in mount and/or a screw in mount and/or a protrusion and/or a locking switch and/or a locking pin and/or a tightening element (for example a screw).

In some embodiments an IOS with a detachable probe 208 may include a calibration procedure to determine the position and/or size of the tip of probe 208. Optionally, probe 208 may be part of a exchangeable set of tools that may serve different functions and/or may have different shapes and/or sizes for example for patients having larger and/or smaller mouths and/or whose teeth are looser and/or tighter. Optionally, the IOS may be used with probe 208 unattached for conventional IOS scanning and/or with probe 208 attached for scanning and/or other functions using probe 208.

Figure 2B:
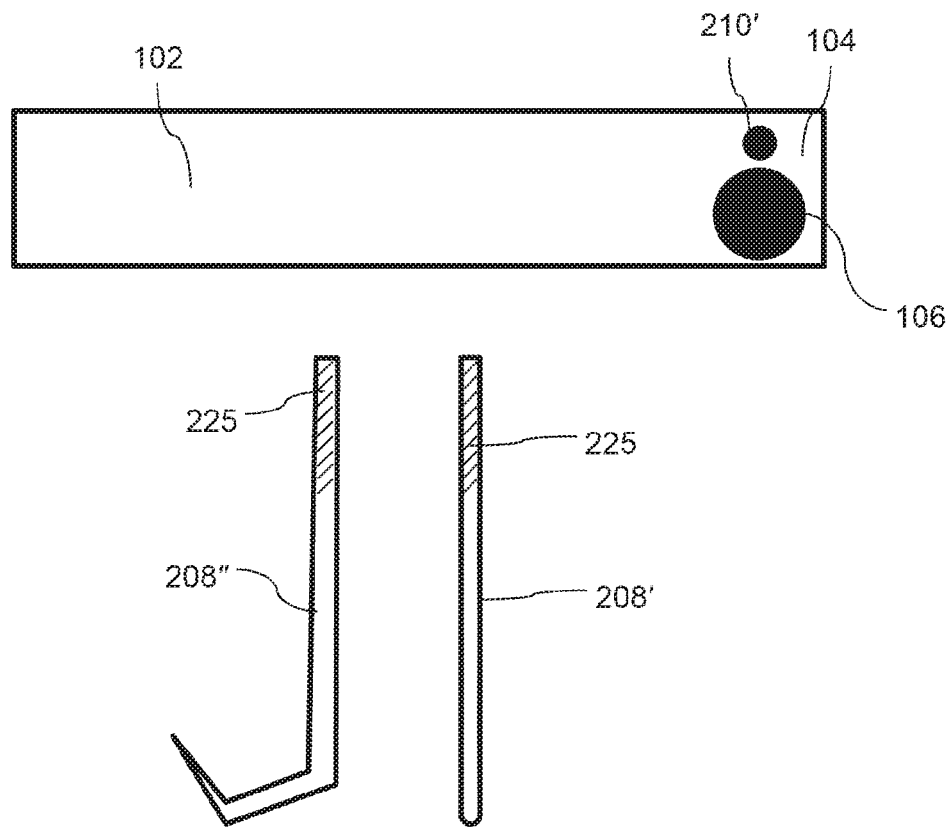
FIG. 2B is a schematic showing of an IOS configured to attach a probe thereon, in accordance with some exemplary embodiments of the invention.

FIG. 2B is a schematic diagram showing of an IOS having a probe attachment mountable thereon, in accordance with some exemplary embodiments of the invention. For example, the IOS includes a threaded mount 210'. Mount 210' secures one of a plurality of different probes for example a straight probe 208' and/or a bent probe 208". For example, thread 225 of the probe 208', 208" may connect to the mount 201'

In some embodiments, a probe 208', of a first shape may be used for one part of the mouth while a probe 208" of a second shape may be used for a different part of the mouth. For example, a straight probe 208 may be used for the facial side of front teeth while an angled probe 208', 208" may be used for the lingual side. Optionally, changing the probe will allow use of the IOS with the probe to scan an entire mouth.

Figure 2C:
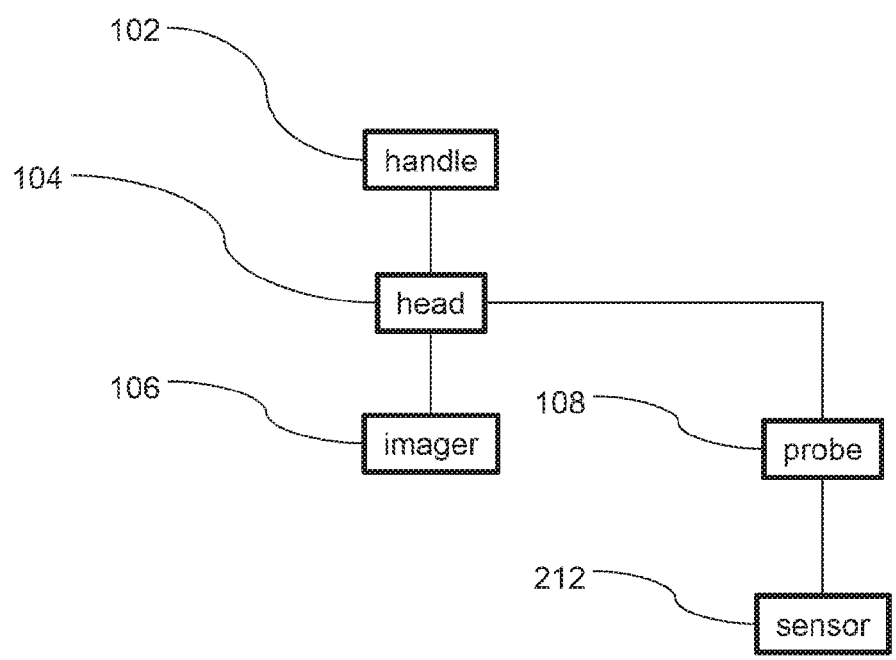
FIG. 2C is a block diagram showing of an IOS having a laterally extending probe with a sensor, in accordance with some exemplary embodiments of the invention.

FIG. 2C is a block diagram showing of an IOS having a probe 108 with a sensor 212 thereon, in accordance with some exemplary embodiments of the invention. For example, a probe mounted sensor 212 may be used to image and/or measure a region that is not accessible to the IOS sensor 106. Alternatively or additionally a probe mounted sensor 212 may be used to monitor progress of an intervention.

In some embodiments, a probe mounted sensor 212 includes an imager and/or a range finder. In some embodiments, an imager may include an ultrasound imager an optical imager (for example a monochrome imager and/or a multi-color imager and/or an ultraviolet UV imager and/or an infrared IR imager and/or an OCT imager). Optionally, a probe mounted imager may be used along with imager 106 of the IOS to make a stereoscopic and/or 3D image of an object (for example the two imagers may have overlapping fields of view). In some embodiments, a range finder may include a laser range finder and/or an ultrasonic range finder.

In some embodiments, a probe mounted sensor 212 may include a force sensor. For example, force on a probe 108 may be measured by a pressure sensor for example near the probe 108 tip. Alternatively or additionally, force on a probe may be measured by a strain sensor for example on a shank of probe 108. Alternatively or additionally, a force sensor may be located at the joint between the probe and head 104. Alternatively or additionally pressure on a probe may be estimated by measuring deformation (e.g. elastic bending) of the probe. For example, deformation may be evaluated from images produced by the IOS. For example, a force sensor may be used to evaluate the stiffness of a structure (for example a tooth and/or a bone) and/or the softness of a structure (for example gums and/or mucosa). For example, softness may be evaluated by correlating deformation of the tissue with the force applied.

Figure 2D:
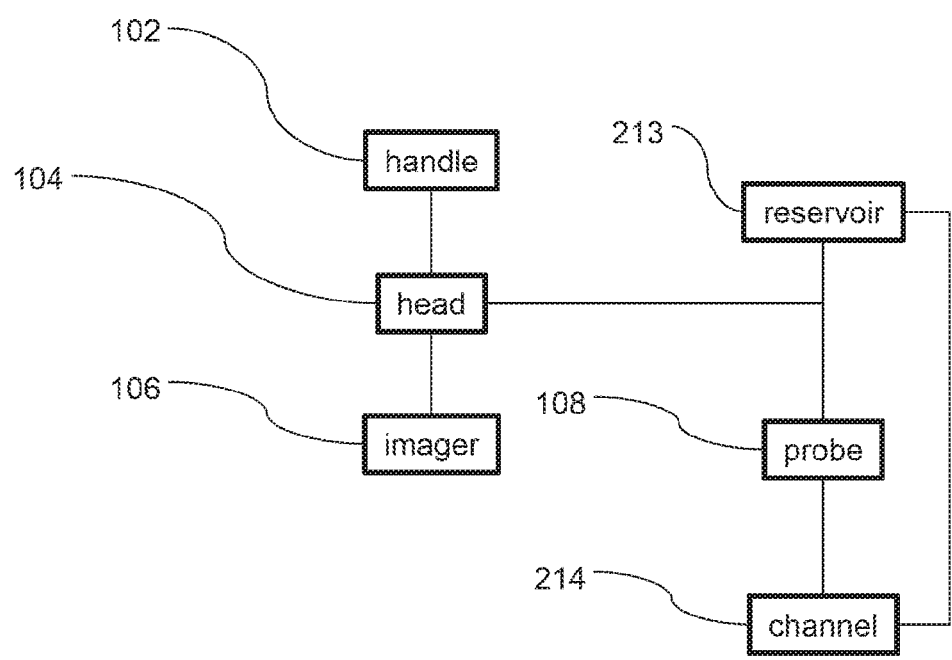
FIG. 2D is a block diagram showing of an IOS having a laterally extending probe with a channel, in accordance with some exemplary embodiments of the invention.

FIG. 2D is a block diagram showing of an IOS having a lateral probe 108 including a channel 214, in accordance with some exemplary embodiments of the invention. Optionally a channel 214 is hollow and/or connected to a reservoir 213. For example, fluid in reservoir 213 may be to introduce into a zone being mapped by the IOS and/or explored with probe 108. For example, a drug may be introduced to treat a condition and/or reduce pain. Alternatively, a cleaning fluid (for example water) may be introduced through channel 214. Alternatively or additionally an abrasive compound may be introduced through channel 214, for example for polishing and/or grinding oral features. Alternatively or additionally channel 214 may be used to suction fluid out from a zone being mapped by the IOS and/or explored with probe 108. Alternatively or additionally, channel 214 include an optical fiber for introducing light into and/or viewing a zone and/or a zone being mapped by the IOS and/or explored with probe 108. Alternatively or additionally, channel 214 may include an optical fiber. For example, the optical fiber may be used for channeling light to a sensor and/or an imager. Alternatively or additionally, a tool may pass through channel 214. For example, wires and/or a tissue ablator may be passed through channel 214 to affect tissue in an oral cavity. Optionally an optical fiber may be used to pass a laser signal for tissue ablation and/or cutting oral features.

Figure 2E:
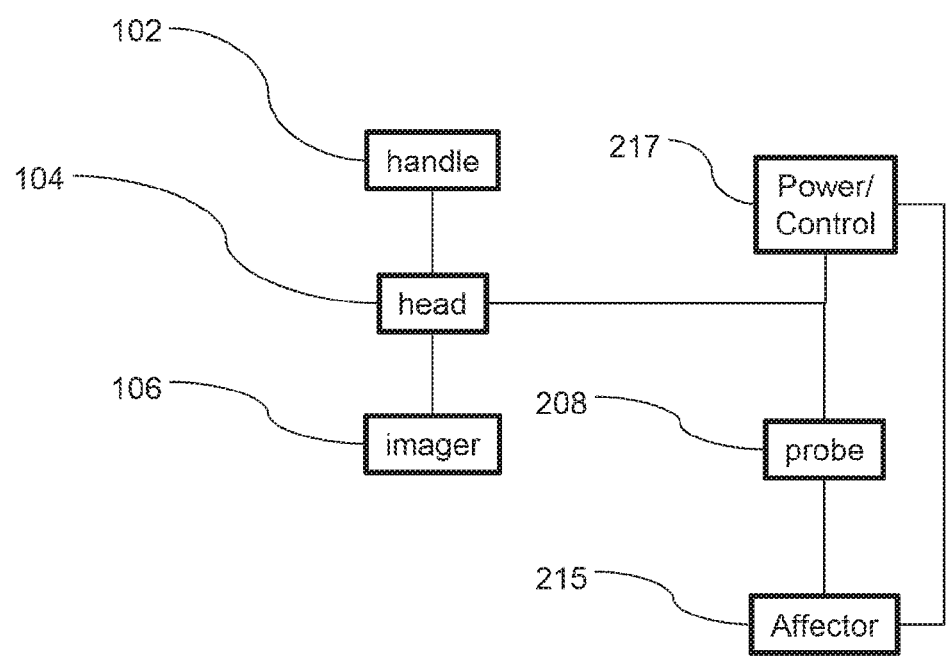
FIG. 2E is a schematic showing of an IOS having a laterally extending probe with an affector, in accordance with some exemplary embodiments of the invention.

FIG. 2E is a block diagram illustration of an IOS having a lateral probe 108 and an affector 215. For example, an affector 215 may include an ablator. Optionally, a power source 217 supplies energy to affector 215. For example, power source 217 and/or affector 215 may be controlled by a controller for example including a processor.

FIGS. 3A-3E are schematic illustrations of IOS including a laterally extending imaging or sensing probes, in accordance with some embodiments of the invention.

Figure 3A:
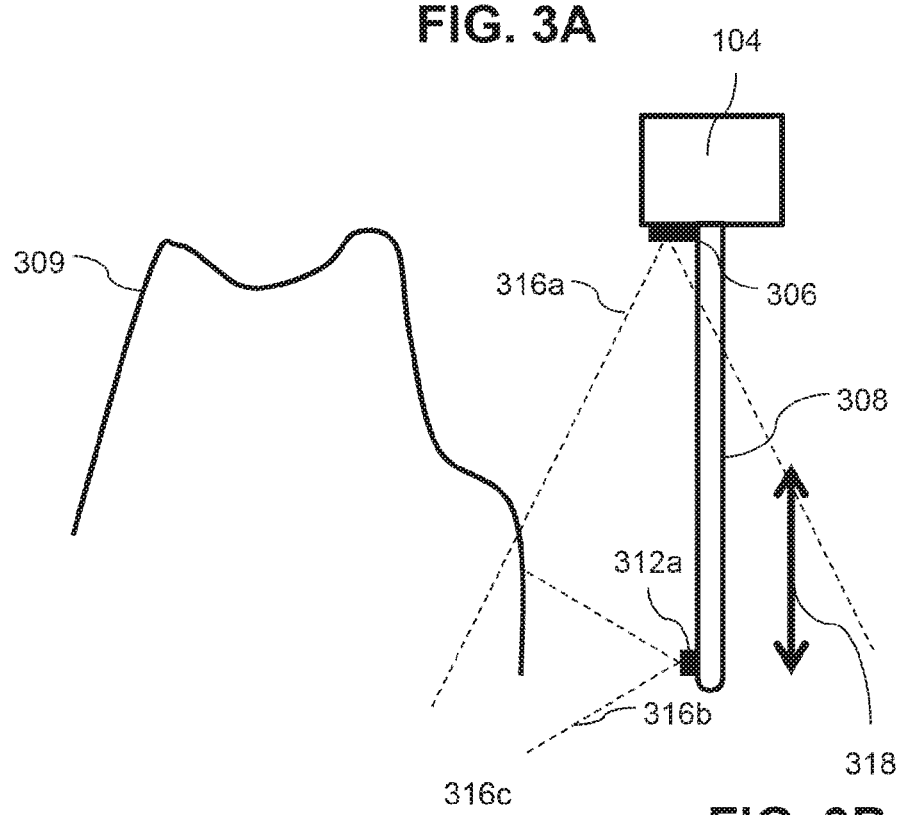
FIGS. 3A-3C are schematic showings of IOS including a laterally extending imaging or sensing probe, in accordance with some embodiments of the invention.

FIG. 3A is a schematic illustration of a probe 308 including an imager 312a in accordance with an embodiment of the current invention. Optionally, a field of view 316b of sensor 312a of probe 308 overlaps with a field of view 316a of imager 306 of the IOS.

In some embodiments, imager 312a will face laterally away from a side of probe 308. Optionally, imager 312a is used to image difficult to reach locations. For example imager 312a may improve accuracy of an imaging of a surface angled away from the IOS imager 306, for example a side view of a steep wall of tooth 309. Optionally the probe may be moved for scanning a structure with imager 312a, for example as illustrated arrow 318. Alternatively or additionally, imager 312a may be used to view subgingival features. For example, measured features may include inflammation, and/or calculus (for example the location and extent and/or thickness) and/or plaque. For example, the tip of the probe and/or sensor 312b may be inserted into a periodontal pocket to make a measurement. In addition to and/or alternatively, a sensor may be directed along the axis of probe 308.

Figure 3B:
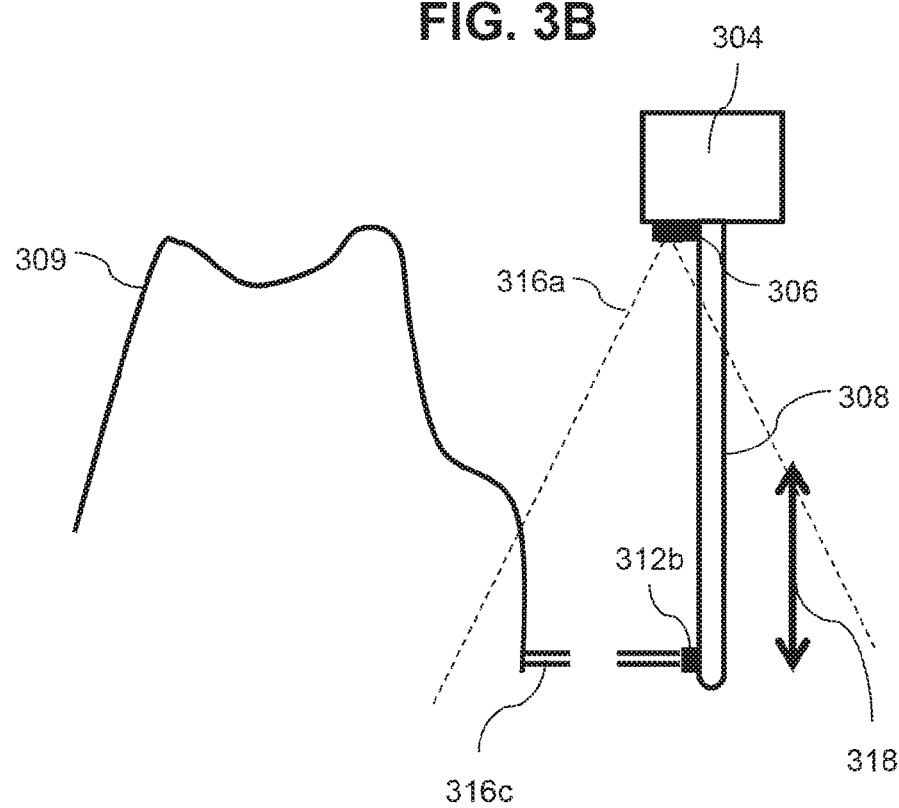

FIG. 3B is a schematic illustration of a probe 308 including a narrow FOV sensor 312b in accordance with an embodiment of the current invention. Optionally, a sensor 312b is used to measure a feature in a field of view 316a of imager 306 of the IOS.

In some embodiments, sensor 312b will face laterally away from a side of probe 308. Optionally, sensor 312b is used to measure features in difficult to reach locations. Optionally the probe may be moved for scanning a structure with sensor 312b, for example as illustrated arrow 318. Alternatively or additionally, sensor 312b may be used to detect and/or identify and/or measure subgingival inflammation, and/or calculus and/or plaque. For example, sensor 312b may include a range finder and/or a color measuring sensor and/or a reflectivity measuring sensor. For example, while sensor 312b is identifying features, IOS sensor 306 may be used to map the location and/or extent of the feature. For example, the location of plaque and/or calculus may be entered into a 3D model of the mouth.

Figure 3C:
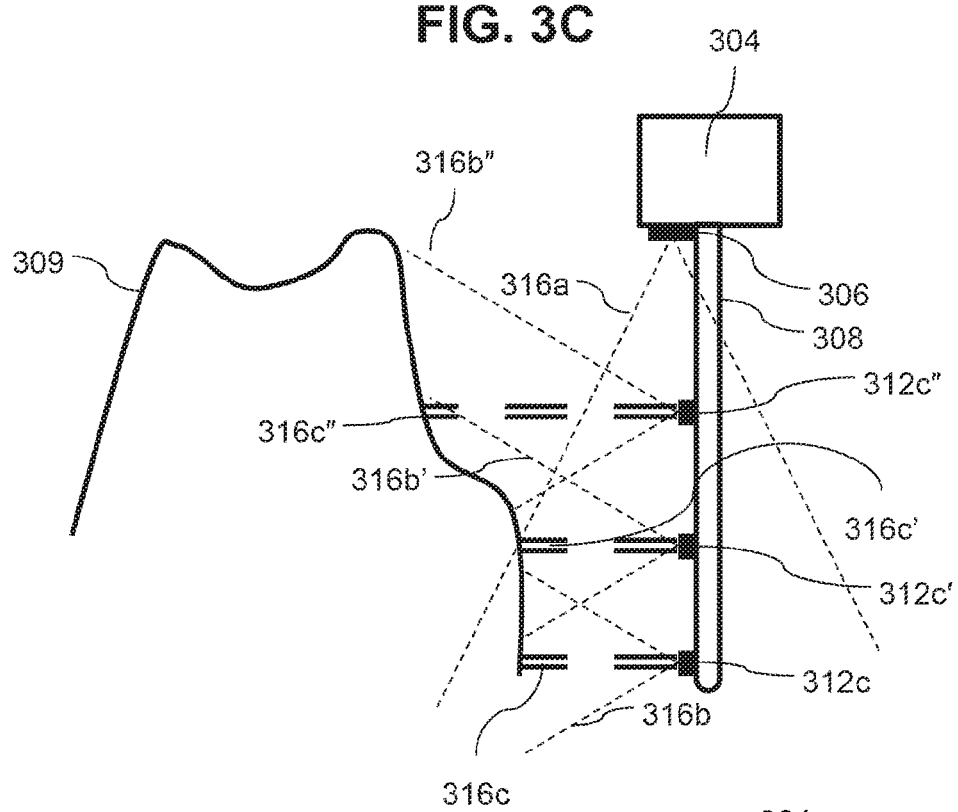

FIG. 3C is a schematic illustration of an IOS including probe having a plurality of sensors in accordance with an embodiment of the present invention. For example, probe 308 is shown with three sensors 312c, 312c' and 312c" having fields of view 316b, 316b' and 316b" respectively. Optionally, the fields of view 316b, 316b' and 316b" overlap; for example, as overlapping fields of view 316b, 316b' and 316b". For example overlapping fields of view 316b, 316b' and 316b" may facilitate stereoscopic and/or 3D imaging.

Optionally, multiple fields of view 316b, 316b' and 316b" may facilitate imaging a large surface of a tooth 309. For example, a surface having a length ranging between 1 to 2 mm and/or between 2 to 8 mm and/or between 8 to 15 mm and/or between 15 to 30 mm. Alternatively or additionally sensors 312c, 312c' and 312c" may include sensors with a narrow FOV 316c, 316c' and 316c". For example, FOV's 316c, 316c' and 316c" may not overlap.

In some embodiments, one or more of the sensors 312c, 312c' and/or 312c" may be replaced by an illuminator. For example, an illuminator may illuminate a narrow field of illumination, for example a zone having a width of greater than 2 mm. Alternatively or additionally, an illuminator may illuminate a wide field of illumination, for example a zone having a width of less than 2 mm. For example, an illuminator may include a light emitting diode (LED) and/or a laser.

In some embodiments, sensors 312c, 312c' and/or 312c" may be used for 3D scanning. For example, overlapping scanners may be used for stereoscopic imaging. Alternatively or additionally, a combination of scanners and illuminators may be used to produce a 3D image. For example, probe 308 may include a laser line scanner.

Figure 3D:
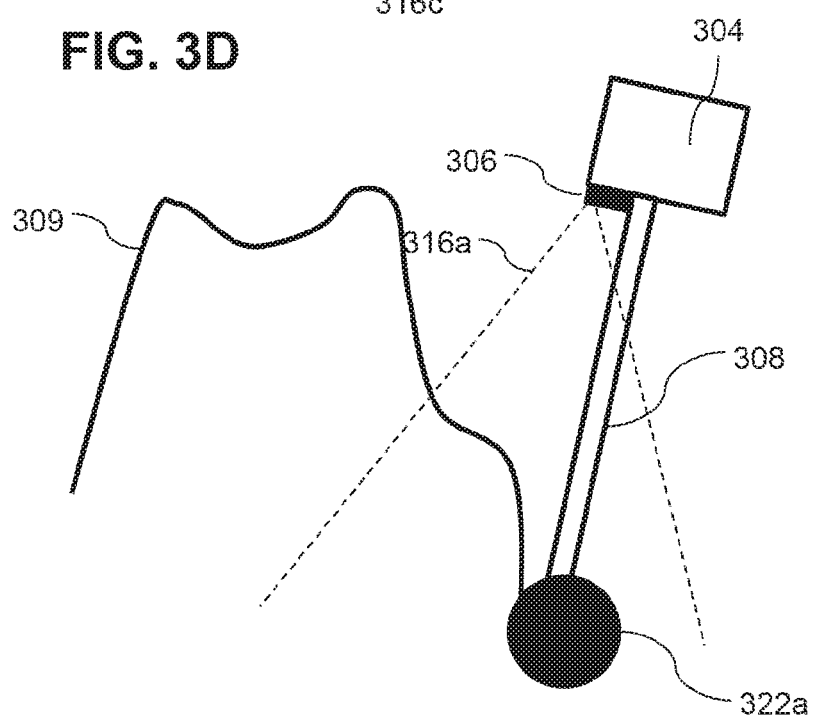
FIGS. 3D-3F are schematic showings of IOS including a laterally extending pressure sensing probe, in accordance with some embodiments of the invention.
Figure 3E:
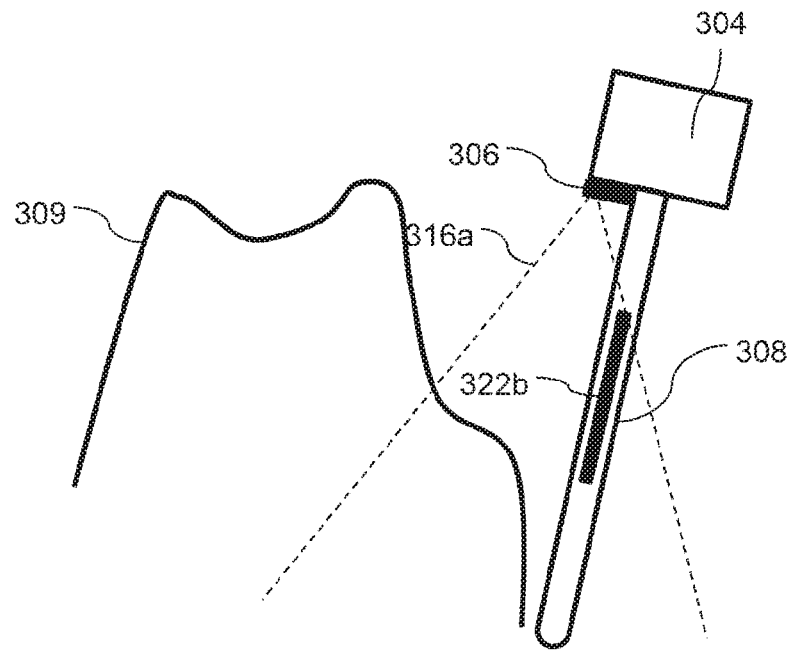
Figure 3F:
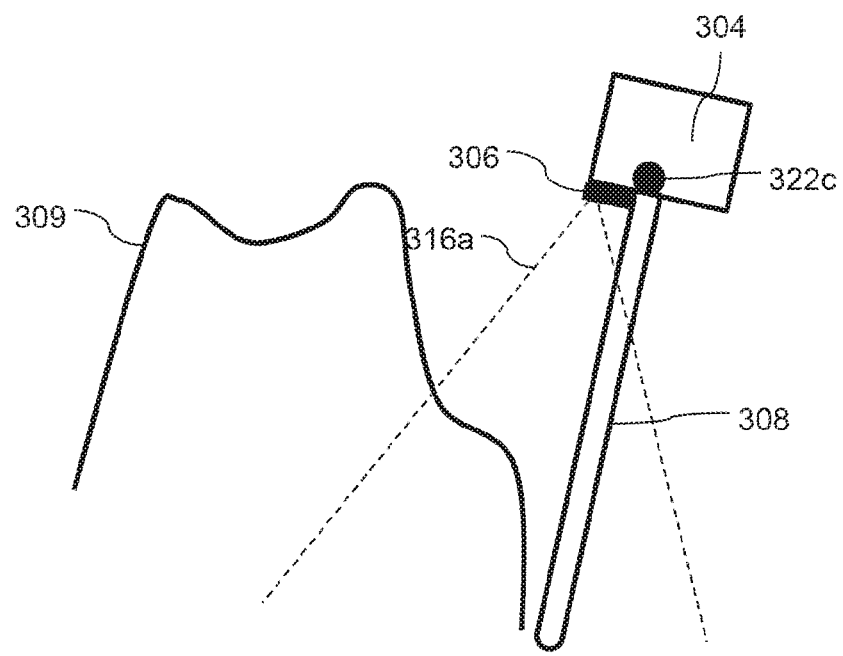

FIGS. 3D, 3E and 3F are schematic illustrations of alternative embodiments of a scanner including a pressure sensor. For example, a probe may include a pressure sensor at a distal portion thereof (for example sensor 322a as illustrated in FIG. 3D). Alternatively or additionally, a stress sensor may be provided at the base of a probe 308 (for example sensor 322c as illustrated in FIG. 3F). Alternatively or additionally, a strain sensor may be including in probe 308 (for example sensor 322b as illustrated in FIG. 3E). Alternatively or additionally, pressure may be estimated based on the image produced by sensor 306 of the IOS head 304. For example the pressure on a flexible and/or elastic probe 308 may be estimated based on the location of contact of the probe 308 and an object and/or the distortion of the probe 308. For example, an elastic probe may be calibrated to know how much lateral force is required at the tip of the probe to bend the probe to a particular angle. For example, from the direction and location of the point of contact between the elastic probe and an object and from the bending of the probe, the force between the probe and the object can be computed.

Figure 4A:
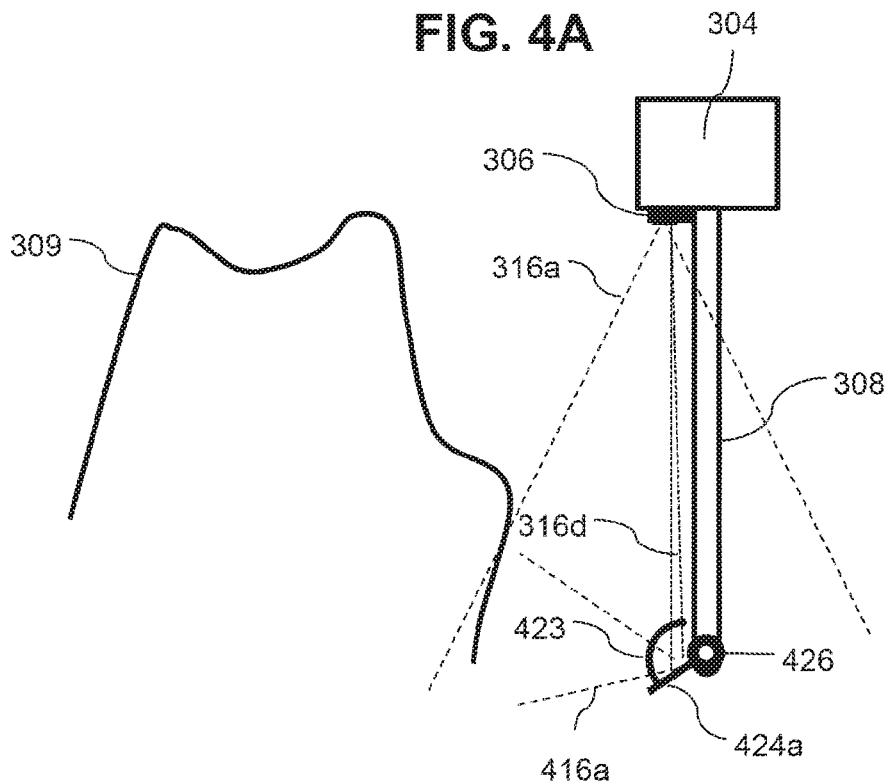
Figure 4B:
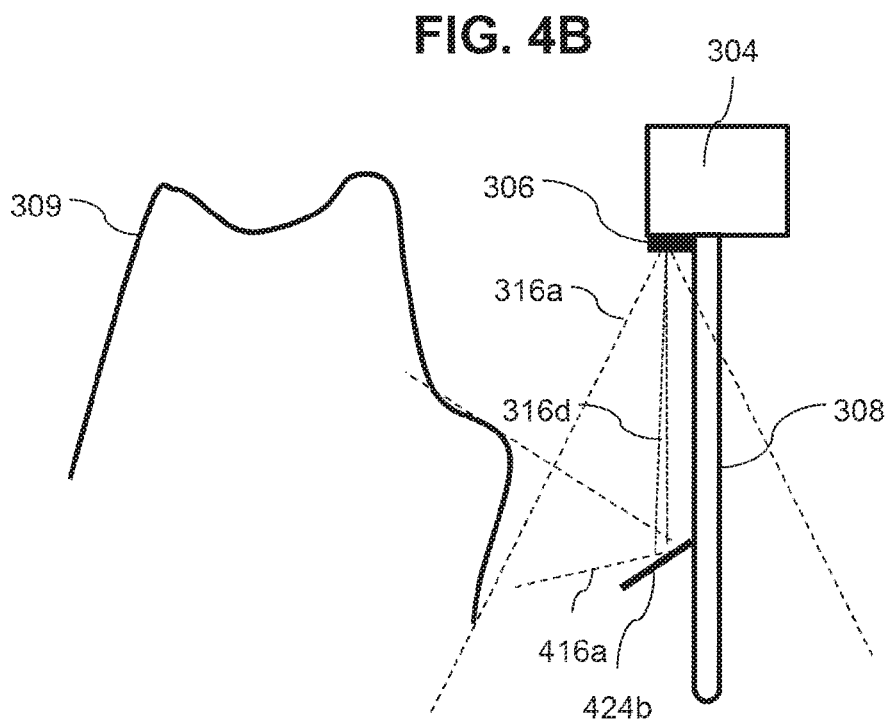

FIGS. 4A-4C are schematic showings of an IOS including a laterally extending probe having a reflector in a field of view 316a of the IOS, in accordance with some embodiments of the invention. For example, a reflector may include a mirror. Optionally a reflector may by straight, and/or curved (for example concave and/or convex). For example, a reflector may give IOS sensor 106 a wider view and/or a view at an additional angle and/or a view at an additional view point than the unmodified view 316a of sensor 306. Optionally the mirror may be used to get a side view of a tooth 309 and/or another structure (for example to see inside a recess for example a cavity in a tooth or gums).

In some embodiments (for example as illustrated in FIG. 4A) a mirror 424a may be located near a tip of probe 308. For example, a portion 316d of FOV 316a of sensor 306 may be directed at mirror 424a. Optionally, the mirror 424a may allow IOS sensor 306 see an additional FOV 416a. Optionally mirror 424b may be mounted on a pivot 426. For example, pivot 426 may facilitate adjusting of an angle and/or FOV 416a of mirror 424a. Alternatively or additionally, pivot 426 may facilitate pivoting mirror 424a out of the way of an obstacle while positioning probe 308. For example, pivot 426 may include an elastic element that allows mirror 424*a* to pivot out of the way and/or return to its pose. For example, mirror 424*a* may be located within 1 mm of the tip of probe 308 and/or within 5 mm and/or within 20 mm and/or within 100 mm.

In some embodiments, a mirror may be directed to produce a field of view 416*a* approximately perpendicular to the probe and/or approximately perpendicular to the mean direction unmodified FOV of the IOS sensor 306. Alternatively or additionally an angle 423 between the mean direction of the surface of the mirror and the a line from the base of the mirror and the IOS sensor 306 may range for example between 40 to 50 degrees and/or between 50 to 80 degrees and/or between 10 to 40 degrees. In some embodiments, angle 423 may be fixed. Alternately or additionally, angle 423 may be adjustable.

In some embodiments (for example as illustrated in FIG. 4B), a mirror 424*b* may be mounted on an intermediate section of the probe 308. For example, mirror 416*b* may be more than 100 mm from the tip of the probe.

In some embodiments, (for example as illustrated in FIG. 4C) a probe 308 may have a widened portion at or near its tip. For example, a tip of a probe may form a ball. Optionally, a reflective surface 424*c* of the widened portion may be located in the FOV 316*a* of the IOS sensor 306. For example, reflective surface 424*c* may be convex and/or may give an expanded FOV 416*b* at an angle to the unmodified FOV 316*a* of sensor 306.

FIGS. 5A-5B are schematic illustrations of an IOS including a laterally extending probe having a channel therein, in accordance with some embodiments of the invention. In some embodiments a channel may be partially or completely filled. In some embodiments a channel may be permanently filled. Alternatively or additionally, the channel may be filled with a temporary object and/or the contents of the channel may be changed. For example by a channel may include of fiber, and/or wire. Optionally an opening of channel may be on various locations and/or directed in various directions. For example opening 511*b* of channel 514*b* is on a distal end probe 308 as illustrated in FIG. 5B. Optionally, opening 511*b* has a field of effect 530*b*. Optionally probe 308 is straight and/or field of effect 530*b* is directed along the long axis of probe 308. Alternatively or additionally, opening 511*a* of channel 514*a* is located on a side of the probe 308 for example illustrated in FIG. 5A. Optionally probe 308 is straight and/or a field of effect 530*a* is directed laterally with respect to the long axis of probe 308. For example, a field of effect may include an area onto which a material is sprayed and/or a field of illumination of a light emitting fiber and/or a field of view of a sensor connected to an optical fiber. Optionally, a channel in a probe may be in fluid communication with a reservoir 513 in the head of the device and/or the handle and/or outside the device. Optionally, a channel in a probe may be in communication with a fluid source and/or an energy source outside the device In some embodiments, reservoir 513 may contain a material to introduce into the mouth and/or may serve to store material removed from the mouth. Alternatively or additionally, reservoir 513 may include a channel to a source of a material to be introduced into the mouth (for example a source of high pressure fluid) and/or to a vacuum. Alternatively or additionally, the reservoir 513 may in include an energy source. For example, the reservoir may include a battery and/or a signal generator and/or a connection to an external power source. For example, power source may supply electrical power to an ablator. For example, the channel 514*a*, 514*b* may include a wire to pass electrical current. For example, a power source may include a light source (e.g. a non-coherent illumination source (e.g. of white light and/or Ultraviolet UV light and/or of Infra-Red IR light) and/or a coherent light source for example a laser). For example, channel 514*a*, 514*b* may include a light guide for example an optical fiber. Optionally, energy passing along channel 514*a*, 514*b* may be used to perform ablation, coagulation, cutting etc. Alternatively or additionally, reservoir 513 may include a sensor, for example an electrical tester and/or an optical sensor.

In some embodiments, while a probe is being used in a procedure, the IOS is optionally used to track progress of the procedure. For example, the probe may be used for scaling a tooth while the IOS is used to determine the initial extent of plaque and/or calculus. In some embodiments, sensors on the probe will be used along with the IOS to improve identification of oral features and/or pathologies and/or their characteristics. For example, the probe may be used to explore a region while the IOS maps the explored region and/or detects optical properties of the region. In some embodiments, a probe will transfer materials into and/or out of the mouth to improve the performance of the IOS and/or of a probe mounted sensor (for example to increase light and/or visibility and/or to provide markings and/or acoustic coupling).

In some embodiments, a channel may be used to transfer materials into or out from a mouth of a patient. For example, a fluid (for example water) and/or a gas (for example air) may be injected through a channel and/or sprayed onto an object. Materials may be introduced at increased pressure, for example of between 0.1 to 1 atm and/or between 0.01 to 0.3 and/or between 1 atm to 5 atm and/or between 5 to 20 atm. For example, the introduced material may be used to rinse the object, for example to wash away blood. Alternatively or additionally a vacuum may be applied to a channel, for example for sucking the blood and/or other fluids/from a mouth. For example, sucking away liquid and/or spraying gas may dry teeth and/or decrease specular reflections from the tooth. In some embodiments, reduced spectral reflection may improve the accuracy of 3D imaging. Alternatively or additionally a hemostatic material may be introduced, for example to reduce bleeding. Alternatively or additionally, an anesthetic material may be introduced, for example to reduce pain. Alternatively or additionally a hemostatic material may be introduced, for example to reduce bleeding. Alternatively or additionally an anti-bacterial material may be introduced, for example to reduce inflammation. In some embodiments a material may be applied to teeth (for example sprayed on the teeth) through a channel to create features on the teeth and help create 3D models. For example a fluid containing particles may be sprayed onto teeth. The particles may be used as visible features for locating features on a tooth. In some embodiments, a channel in a probe may be used for spraying or insert a material that causes gum retraction and/or a material that opens a sulcus. Alternatively a channel may be used to transfer a material for affecting a surface; for example a milling and/or polishing solution. For example, a milling solution containing particles may be sprayed onto a tooth through a channel in a probe.

In some embodiments, a channel may be used for a fiber and/or a wire. For example a hollow probe may include an internal fiber. Optionally, the fiber includes an optical fiber that transports light. For example, a light source may be included in reservoir 513 and/or at a proximal end of the fiber. For example, the light carried by the fiber may be coherent and/or the light source may include a laser. Alternatively or additionally the light may be non-coherent and/or the light source may include a light emitting diode.

In some embodiments, the fiber passing through probe 308 acts as a source of light. For example, probe 308 may include holes and/or windows that project light columns for calibration and/or measuring distance. Alternatively or additionally a fiber may carry light effective to cut tissue. For example, a hollow probe may include an internal fiber used for delivering light for soft tissue management, such as cutting gums and/or stopping bleeding for example by clotting blood.

In some embodiments a light transmitting fiber may be connected to a lights sensor. For example hollow probe may contain internal fiber connected to a light sensor that measures light reflected from an object towards the probe and/or the tip thereof and/or light reflected from the probe. For example, changes in reflected light may be used to identify when the probe is touching an intra-oral object, for example a tooth. For example, the sensor may measure changes in intensity and/or color. Alternatively or additionally, light may be measured with an optical detector on the probe, for example on or near a tip of the probe. In some embodiment, a fiber and light sensor may be used as a newton-meter for contact/force measurement detected via changes in light.

In some embodiments, an optical fiber will be used to measure distance. For example, a fiber may be connected to an optical length meter. Optionally, one or more fibers will be open approximately perpendicular to the axis of probe 308. For example, the fiber may be used to measure a distance from the side of probe 308 to an oral feature, for example a wall of a tooth. Alternatively or additionally, an optical length meter may be connected to a ribbon of fibers. For example, the device may measure distance from each fiber end to an oral feature. Alternatively or additionally, a probe channel may transfer light without an optical fiber. For example the channel may include a light reflecting interior or other options to transfer light for any of the purposes described above with respect to optical fibers.

Figure 6:
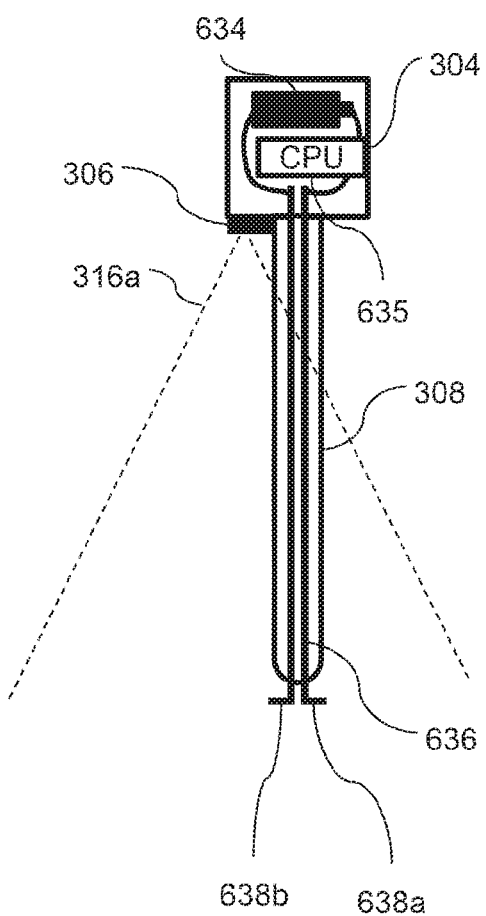
FIG. 6 is a schematic showing of IOS including a laterally extending probe having an affector, in accordance with some embodiments of the invention.

FIG. 6 is a schematic showing of IOS including a laterally extending probe having an affector, in accordance with some embodiments of the invention. Optionally, an affector may include electrodes 638a and/or 638b. For example, electrodes 638a, 638b may be connected by a wire 636 to a power source 634 and/or a controller 635. Optionally, controller 635 may include a processor. Optionally the power source 636 and/or controller may produce an electrical current (AC or DC and/or at a radio frequency). For example the affector may be used to ablate tissue and/or stop bleeding and/or measure resistance. Alternatively or additionally, a heated object may be mounted to a probe as an affector. Alternatively or additionally, an affector may transfer light to an intra-oral object. For example, light may be used for ablation and/or milling. For example, a tooth may be milled in preparation for a procedure such as attachment to prosthesis.

FIG. 7A is a schematic showing of IOS including a telescopic probe, in accordance with some embodiments of the invention. In any of the embodiments described herein, a probe may be fixed and/or telescoping and/or reversibly mounted to the handle 302. For example, the IOS handle 302, head 304 and/or sensor 306 may be used as a standard IOS (for example with the probe 708 and/or 208' and/or 208" collapsed and/or removed). Alternatively and/or additionally, the probe (for example with the probe 708 and/or 208' and/or 208") may be extended and/or attached and then used for any of the procedures and/or embodiments as described herein. Optionally, a telescoping probe 708 may be extended automatically and/or manually. Optionally, the telescoping probe 708 may be configured for use in a fully retracted and/or a fully extended state. Alternatively or additionally, the telescoping probe may also work in a partially extended state.

In some embodiments, a telescoping probe 708 includes one or more nested parts. Optionally, the parts may retract one into the other and/or extend one from the other. The probe optionally extends and/or locks into an extended position. For example, the parts may be connected to a linear actuator and/or interconnected by screw threads and/or another locking mechanism.

Figure 7B:
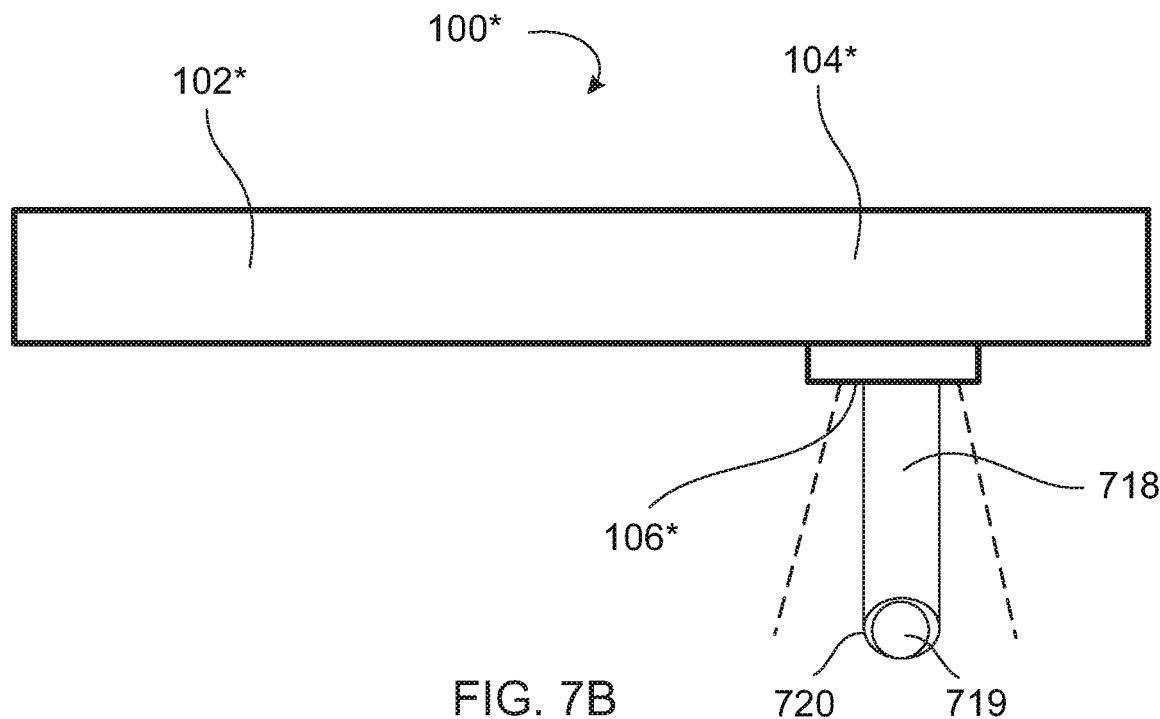
FIG. 7B is a schematic showing a probe with a tip designed for smooth or gliding movement along an oral surface in accordance with some embodiments of the invention.

FIG. 7B is a schematic showing a probe with a tip designed for smooth or gliding movement along an oral surface in accordance with some embodiments of the invention.

FIG. 7B is a schematic showing an IOS 100* with a probe 718; an imager 106*; a head 104* and a handle 102*.

In some embodiments, the probe 718 is designed with a ball 719 at a tip 720 of the probe 718. In some embodiments the probe 718 is optionally designed so that the ball 719 can roll, optionally like a ball-point pen refill.

In some embodiments, the probe 718 is optionally designed with a round tip 720.

In some embodiments, the probe 718 is optionally designed with a tip 720 made of a smooth material, such as, by way of some non-limiting examples, Teflon, nylon.

In some embodiments, the ball 719 is designed to roll as it touches a scanned object, for example teeth or gums.

In some embodiments, the scanner includes a component to measure a rolling distance of the ball 719. By way of a non-limiting example, markings such as lines or dots are drawn on the ball, and the scanner optionally images the markings, optionally with an imager, and the rolling distance is optionally calculated.

By way of another non-limiting example, the surface of the ball 719 optionally includes (optionally subtractive or additive) mechanical lines that are optionally sensed by a force sensor.

By way of another non-limiting example, the ball 719 is optionally optically clear and striped to act similarly to a computer mouse or scroll wheel encoder. In some embodiments the probe is optionally hollow, and optionally includes one or more internal optical fibers to enable viewing movement of the ball or through the ball, or collect information from the ball or through the ball.

In some embodiments, air pressure liquids, anti-aggregant or anti-clot material optionally keeps the ball 719 from sticking to the probe tip 720, potentially assisting the ball 719 rolling.

Figure 7C:
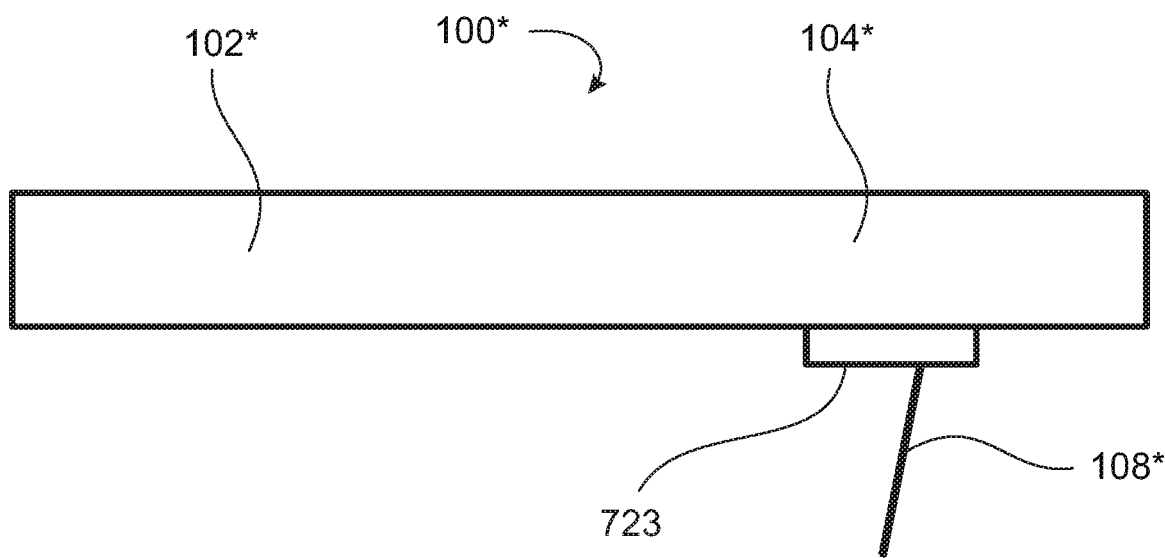
FIGS. 7C and 7D are schematics showing an option for release of a probe from an IOS, in accordance with some embodiments of the invention.
Figure 7D:
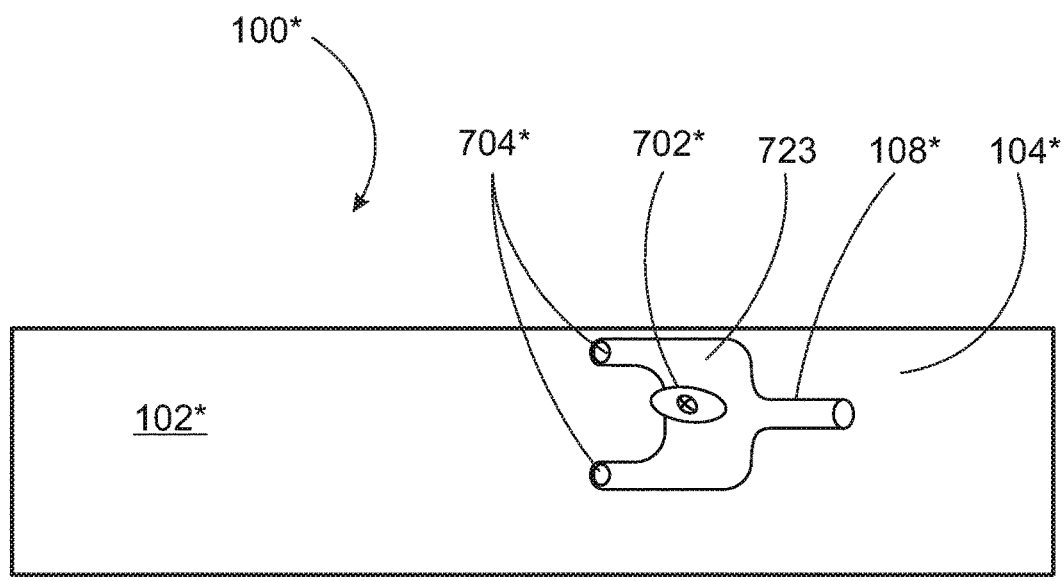

FIGS. 7C and 7D are schematics showing an IOS 100* with an option for release of a probe from an IOS, in accordance with some embodiments of the invention.

FIGS. 7C and 7D show a probe 108*; a probe release mechanism 723; a head 104* (in some embodiments with an optional scanner or imager, not shown) and a handle 102*, where FIG. 7C is a side view and FIG. 7D is a bottom view.

FIG. 7D shows the example embodiment where the probe release mechanism 723 is configured to release the probe 108* by inserting a tool into one or more openings 704* in the probe release mechanism 723. By way of a non-limiting example there may be two openings 704* in the probe release mechanism 723, shaped to receive tips of a forceps (not shown). The forceps may optionally be squeezed or spread, acting via the openings 704* on a probe holder 702* to release the probe 108* from the IOS 100*.

FIGS. 7C and 7D show an option for a quick release of the probe from the IOS.

In some embodiments a quick release is used in order to replace a probe 108* between patients or to replace the probe 108* type according to an anatomy of the patient, for example to replace to a shorter probe in case of shorter molar teeth, and/or to a narrower probe in case of a narrow opening between two teeth and/or to a probe with a force sensor for example to measure the force applied to a tooth.

In some embodiments the quick release is optionally done with a specific tool that can create enough force to remove the probe 108* from its place. In some embodiments, a tool that is already usually used by dentists can be used, for example, a tooth ring placing forceps.

In some embodiments the probe holder 702* grips the probe 108* along a section long enough to provide stability against side forces shifting the probe 108* relative to an imager (not shown).

In some embodiments the IOS 100* is optionally calibrated to determine the location of a probe 108* after replacement.

Figure 7E:
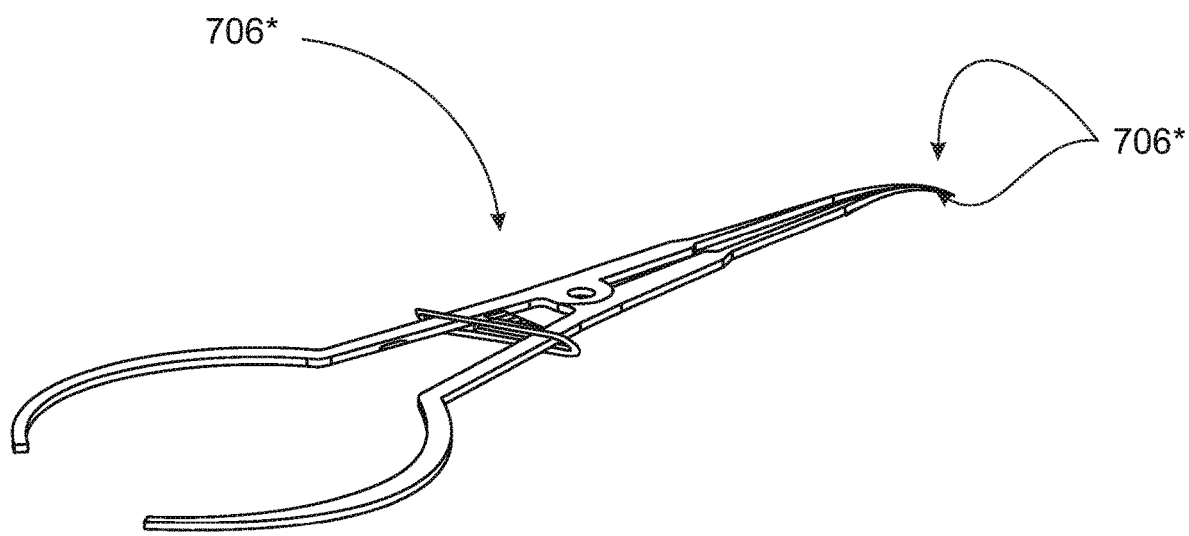
FIG. 7E is an image of an optional tool for release of a probe from an IOS, in accordance with some embodiments of the invention.

FIG. 7E is an image of an optional tool for release of a probe from an IOS, in accordance with some embodiments of the invention.

FIG. 7E shows a forceps 706* which has tips 708* which can be used for releasing a probe from an IOS, for example, referring to FIG. 7C, by inserting the tips 708* into the openings 704* as described above.

Figure 7F:
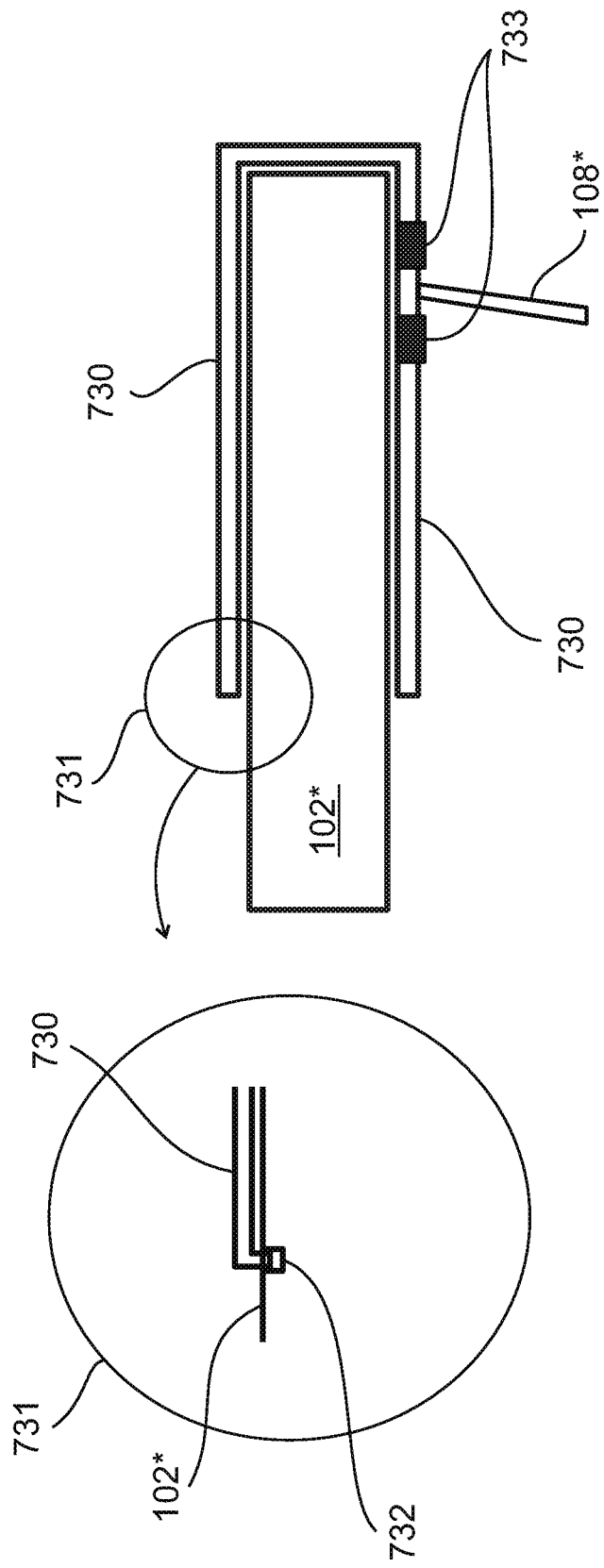
FIG. 7F is a schematic showing a sleeve with a probe that is placed over an IOS, in accordance with some embodiments of the invention.

FIG. 7F is a schematic showing a sleeve with a probe that is placed over an IOS, in accordance with some embodiments of the invention.

FIG. 7F shows a probe 108* attached to a sleeve 730 and the sleeve 730 is placed over an IOS 102*.

In some embodiments the sleeve 730 optionally includes a release component 732 for attaching to and detaching from the IOS 102*. In some embodiments the release component 732 is a quick release component 732. An enlarged portion 731 of FIG. 7F shows an optional quick release component 732.

In some embodiments the sleeve 730 optionally includes a clear window or windows 733 to enable a scanner to image through the window(s) 733 in the sleeve 730.

In some embodiments the sleeve 730 is made fully or partially of a light transferring material such as polycarbonate.

In some embodiments the sleeve 730 can be autoclaved, in order to sterilize between uses.

In some embodiments the sleeve 730 is configured so that when placed over the IOS 102* such that relative movement between the sleeve 730 and the IOS 102* is limited to less than 1 micron or 5 microns.

In some embodiments the release component 732 of the sleeve 730 is configured such that relative movement between the sleeve 730 and the IOS 102* is limited to less than 1 micron or 5 microns.

Figure 7G:
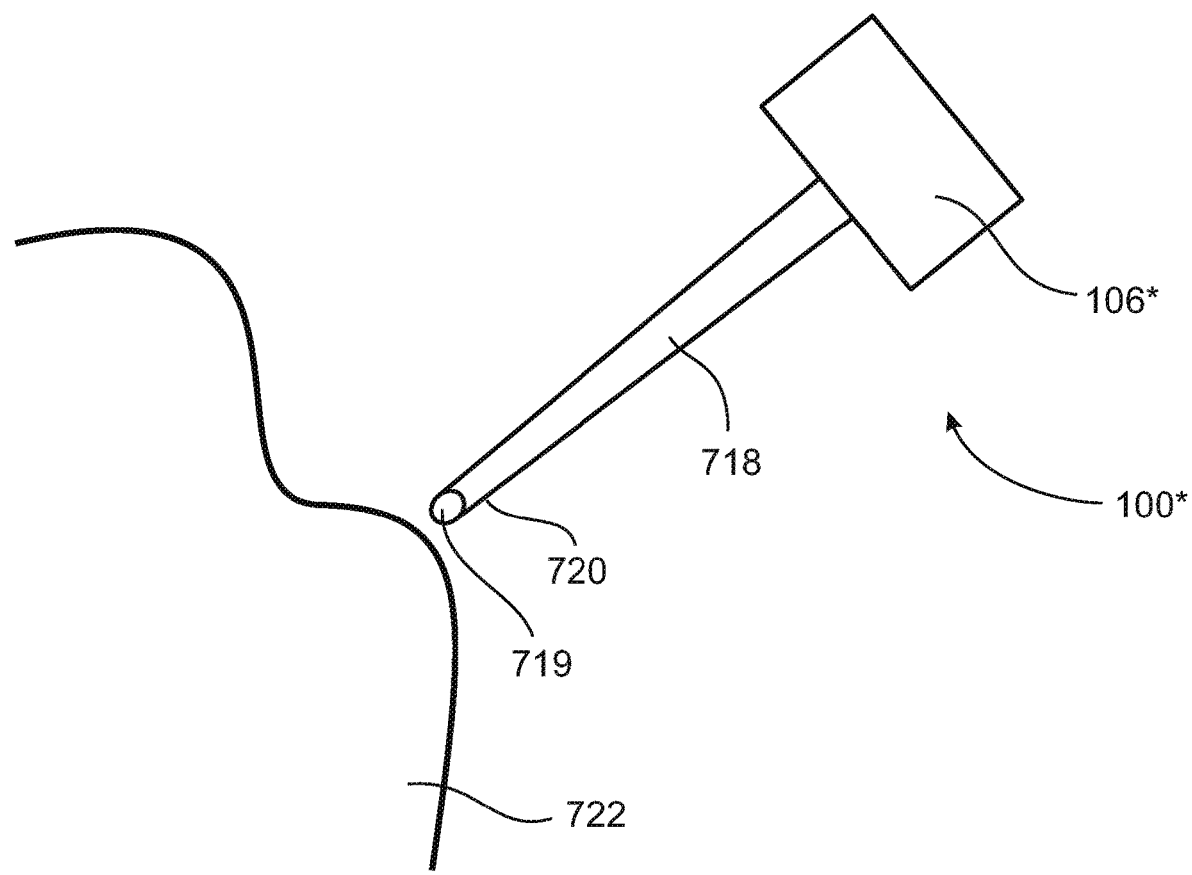
FIG. 7G is a schematic showing a probe with a tip including a ball designed for smooth movement along an oral surface in accordance with some embodiments of the invention.

FIG. 7G is a schematic showing a probe with a tip including a ball designed for smooth movement along an oral surface in accordance with some embodiments of the invention.

FIG. 7G is a schematic showing an IOS 100* with an imager 106* and a probe 718.

The probe 718 of FIG. 7G is designed with a ball 719 at a tip 720 of the probe 718. In some embodiments the probe 718 is optionally designed so that the ball 719 can roll, optionally like a ball-point pen refill.

FIG. 7G shows the ball 719 at the tip 720 of the probe 718 rolling along a surface of a tooth 722.

Exemplary Measurements Using IOS with Laterally Extending Probe

FIGS. 8A-8K are schematic drawings showing various dental structures which may be measured using an IOS and a probe, in accordance with some embodiments of the invention.

Figure 8A:
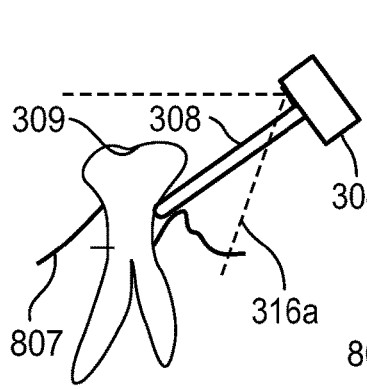
FIGS. 8A-8K are schematic drawings showing various dental structures which may be measured using an IOS and a probe in accordance with some embodiments of the invention.

FIG. 8A illustrates an IOS scanner with a probe exploring a periodontal pocket between a tooth 309 and a gum 807 in accordance with an embodiment of the current invention. For example, a probe 308 may be a simple probe without an additional sensor. Alternatively or additionally, a pocket may be explored using a probe with a probe mounted sensor, for example as illustrated in FIG. 13B.

Figure 8B:
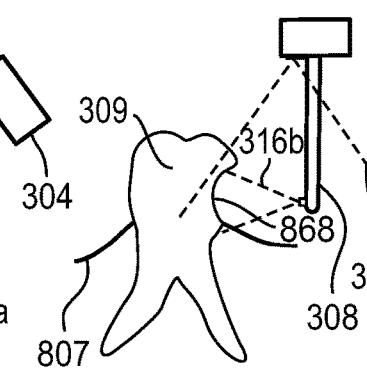

FIG. 8B illustrates an IOS scanner including a probe measuring a recess 868 in a tooth in accordance with an embodiment of the current invention. For example, a recess 868 may be scanned at high resolution in order to fit an implant. Optionally, probe 308 is used to position a FOV 316*b* of probe mounted sensor to get a good view of the recess 868. Alternatively or additionally, a probe mounted sensor may inserted into the recess 868. Alternatively or additionally, a probe may be used to physically contact an internal portion of the recess 868. A probe physically contacting an internal portion of the recess 868 optionally includes a probe mounted sensor. Alternatively or additionally probe physically contacting an internal portion of the recess 868 may not include a probe mounted sensor.

Figure 8C:
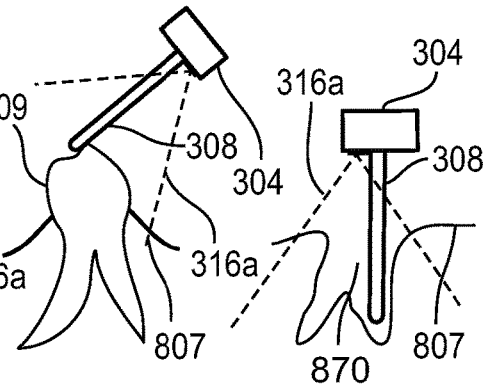

FIG. 8C illustrates an IOS scanner including a probe measuring an exterior surface of a tooth in accordance with an embodiment of the present invention. For example, use of the probe to measure the outer surface may improve the accuracy of a 3D map and/or STL file. Alternatively or additionally, use of a probe along with the IOS scanner may produce a high accuracy map of the surface of the tooth and/or facilitate production of an improved fitting onlay. For example, mapping the surface may include touching points on the surface with the probe. Alternatively or additional, a probe mounted sensor may be used to scan a tooth surface.

Figure 8D:
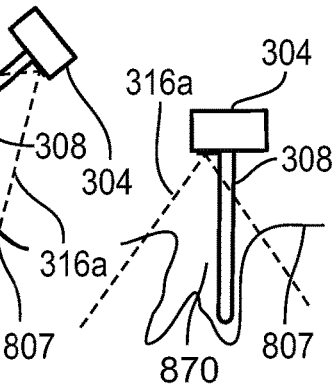

FIG. 8D illustrates an IOS scanner including a probe measuring recess, for example a socket 870 remaining after extraction of a tooth in accordance with an embodiment of the present invention. For example, use of the probe to measure the socket 870 may improve the accuracy of a 3D map and/or STL file. Alternatively or additionally, use of a probe along with the IOS scanner may produce a high accuracy map of an inner surface of the socket and/or facilitate production of an improved fitting prosthesis, for example an inlay, an onlay and/or an implant fitting to a feature in the socket 870. Alternatively or additional a probe mounted sensor may be used to scan an extraction socket 870. For example, the probe mounted sensor may be inserted into the socket 870. Alternatively or additionally a probe mounted sensor may be positioned outside the socket 870 to have a FOV with good coverage of the socket 870, for example close to and/or adjacent to the opening of the socket 870. Optionally, data from measurement of the socket 870 may be used to produce an implant for immediate and/or primary implantation. An IOS including a probe is optionally used to measure grooves, holes and cavities in bone, for example to be designated for medical objectives, for example, for dental implants.

Figure 8E:
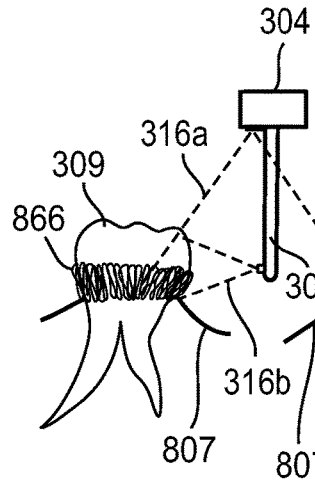

FIG. 8E illustrates a use of an IOS including a probe to measure a tooth abrasion 866 in accordance with an embodiment of the current invention. Optionally, probe 308 is used to position a FOV 316*b* of a probe mounted sensor to get a good view of the abrasion 866. Alternatively or additionally, a probe may be used to physically contact the abrasion 866. A probe physically contacting a the abrasion 866 optionally includes a probe mounted sensor. Alternatively or additionally, a probe physically contacting abrasion 866 may not include a probe mounted sensor.

Figure 8F:
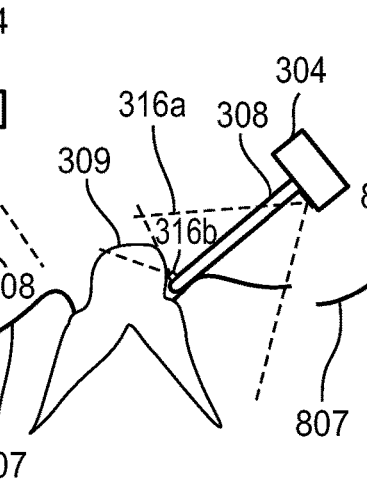

FIG. 8F illustrates an IOS scanner including a probe measuring a region prepared for a prosthesis (for example a surface of a tooth prepared for a crown) in accordance with an embodiment of the current invention. For example, prepared region may be scanned at high resolution in order to fit a prosthesis. Optionally, probe 308 is used to position a FOV 316b of probe mounted sensor to get a good view of the region. Optionally the probe contacts the region. A probe physically contacting region optionally includes a probe mounted sensor. Alternatively or additionally probe physically contacting region may not include a probe mounted sensor.

Figure 8G:
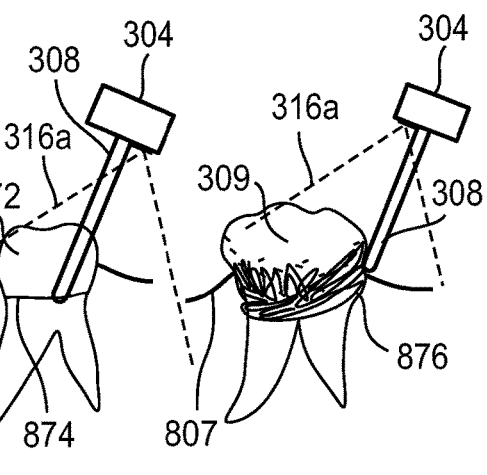

FIG. 8G illustrates an IOS scanner including a probe measuring a prostheses after attachment in accordance with an embodiment of the present invention. For example, the probe is used to measure the joint 874 between a natural structure (for example between a prepared tooth 309 and a crown 872) and the prosthesis. Alternatively or additionally, the probe may be used along with the IOS scanner to measure a height of a prosthesis and/or to measure closure of the prosthesis with an antagonistic tooth. In some embodiments a IOS scanner with a probe may measure a post insertion fit of a prosthesis without a probe mounted sensor. Alternatively or additionally, a probe measuring a post insertion fit of a prosthesis may include a probe mounted sensor.

Figure 8H:
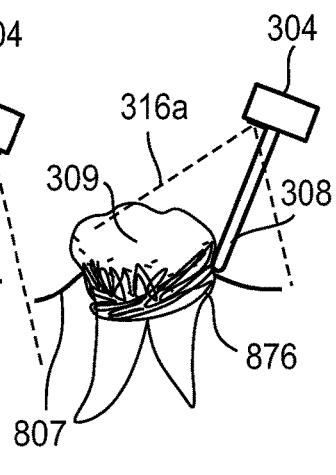

FIG. 8H illustrates an IOS including a probe used to measure and/or treat a calculus and/or a plaque deposit 876 in accordance with an embodiment of the current invention. For example, a probe 308 may be used to contact deposit 876, for example to measure the deposit 876 and/or to scrape the deposit 876. Optionally, the IOS will be used to map the 3D extent of the deposit 876 and/or to track progress in its removal. In some embodiments, probe 308 will be a simple probe. For example, the probe may measure by contact and/or remove deposit 876 by physical scaling. Alternatively or additionally, a probe may include a sensor and/or an affector (for example an ultrasonic scaler) that may take part in the measurement and/or treatment.

Figure 8I:
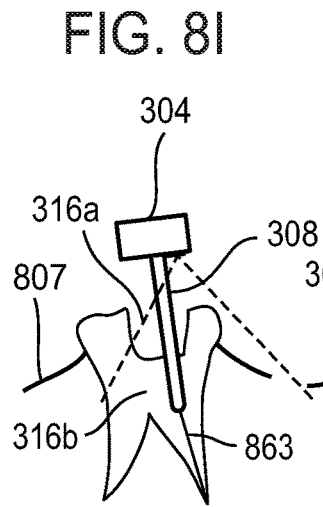

FIG. 8I illustrates an IOS scanner including a probe measuring and/or treating a root of a tooth in accordance with an embodiment of the present invention. For example, the probe 308 may be used to remove organic tissues and debris 863 in a root and/or the IOS may be used to measure the extent of the procedure. Alternatively or additionally, use of a probe along with the IOS scanner may produce a high accuracy map of the removed tissue and/or facilitate production of an improved fitting prosthesis, for example an inlay, an onlay and/or an implant. In some embodiments, probe 308 may be a simple probe. Alternatively or additional the probe may include a probe mounted sensor. Alternatively or additional the probe may include a probe mounted affector. For example, the probe may include a laser and/or a light channel to ablate the nerve 863 and/or a vacuum to remove nerve tissue and/or debris. In some embodiments the probe may be curved and/or flexible.

Figure 8J:
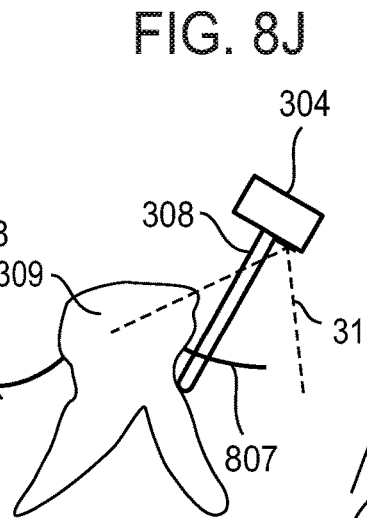

FIG. 8J illustrates an IOS scanner including a probe measuring a sub-gingival structure in accordance with an embodiment of the present invention. For example, a probe may be inserted through soft tissue (for example gums 807) to contact and/or measure hard tissue underneath. In some embodiments the probe 308 is optionally inserted through the gingiva of the gums 807 and optionally touches a bone in which the teeth are embedded. Such embodiments may be used to diagnose and for planning of periodontal surgery and/or in order to add measurement results to a periodontal chart and/or to a 3D model. In some embodiments a thickness of the gingiva tissue is optionally measured, optionally based on knowing the probe length, and knowing, optionally using the 3D scanner, where the gingiva is, and calculating the thickness of the gingiva.

In some embodiments, the probe 308 is made with a sharp tip, to ease insertion into a space between a tooth and gums and/or through soft tissue.

In some embodiments, a pressure sensor is optionally used to detect when the probe 308 contacts bone.

Figure 8K:
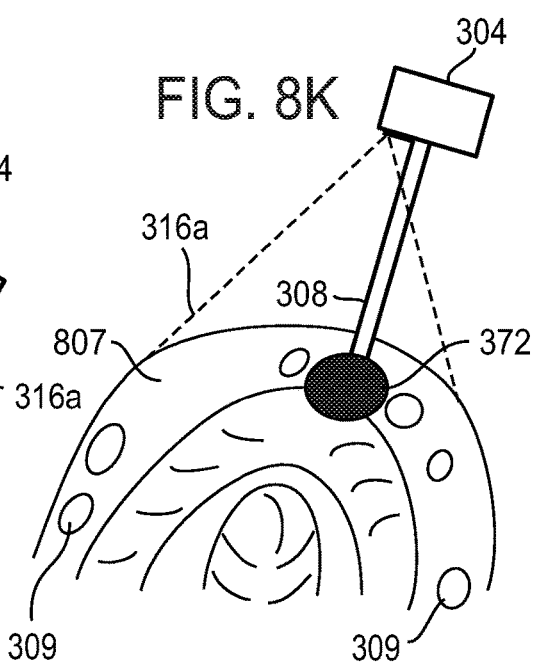

FIG. 8K illustrates an IOS scanner measuring soft tissue in accordance with an embodiment of the current invention. For example, a scanner may be used to measure mucosa for fitting a removable prosthesis. For example, a IOS and/or probe may be used to measure a 3D form of the tissue and/or a mechanical property, for example elasticity. The tip 372 of the probe may optionally include an enlarged portion for improving measurement of soft tissue and/or to protect the tissue from damage. Alternatively or additionally the probe may include a sensor, for example a force sensor.

FIG. 8L is a simplified illustration of an IOS measuring gingiva surrounding a dental implant in accordance with some embodiments of the invention.

FIG. 8L shows gingiva 807* adjacent to an implant 808, and an IOS head 304 and probe 308.

In some embodiments the IOS head 304 and the probe 308 are optionally used to collect data for producing a 3D model of the gingiva 807*, and optionally of the implant 808, and optionally of an abutment.

In some embodiments the IOS head 304 and the probe 308 are optionally used to collect data for producing a 3D model of the gingiva 807* with no abutment.

In some embodiments the IOS head 304 and the probe 308 are optionally used to collect data for producing a 3D model of the gingiva 807* with an abutment present.

In some embodiments the 3D model is optionally used to design a custom abutment, which is optionally shaped according to the gingiva shape.

FIGS. 8M and 8N are simplified illustrations of an IOS measuring parameters of a dental implant in accordance with some embodiments of the invention.

FIGS. 8M and 8N show an IOS head 304 using a probe 308 measuring parameters of a dental implant 809.

Example parameters measured by the probe 308 include, by way of some non-limiting examples, a location of the dental implant 809, orientation of the dental implant 809, shape of the dental implant, and similar geometric parameters, optionally relative to adjacent teeth (not shown), and/or relative to a jaw bone and/or relative to gums.

In some embodiments the measurement is optionally done using a number of known point 810 locations on the implant 809.

In some embodiments the number of points is selected to enable determining a specific shape of an implant 809 that are enough in order to know the parameters due to the implant synthetic shape.

In some embodiments measurement of the implant 809 is optionally done in presence of blood covering some or all of the implant 809, for example after implant 809 insertion into bone or after opening covering gingiva 807* to expose the implant 809.

In some embodiments detection and/or location and/or measurement of the implant 809 is optionally using a metal detecting component (not shown) in the IOS head 304 and/or the probe 308 and/or a tip of the probe 308.

In some embodiment the metal detecting component optionally includes a one or more conductive loops, similar to those a metal detector head, connected to a metal detection circuitry in the IOS head 304.

In some embodiments the metal detector is optionally used to detect and/or locate an implant below gingiva, before punching the gingiva and exposing the implant. Such an embodiment potentially enables direction the punching or cutting open of the gingiva to the right place.

In some embodiments detecting a center of the implant is optionally done taking into account symmetry of the implant, that is, detecting a point where the metal detector detects the metal equally from all sides.

In some embodiments the metal detector optionally determines a location of the metal implant relative to a sensor inside the probe. The probe position is optionally determined relative to a scene captured by the scanner/imager. The implant location is optionally determined relative to, for example, teeth location.

In some embodiments an implant location is optionally printed on a printout which is optionally placed on a tooth or teeth, optionally with registering marks printed, and showing a location of the implant, in some embodiments even having a cut-out or opening at a location suitable for punching a gum to expose the implant.

In some embodiments measurement parameters are optionally determined based on knowing a tip position in scanned images, or in the scanner coordinate system.

In some embodiments reaching and/or locating a bone or tooth or implant is optionally determined by a force sensed by a force sensor.

In some embodiments, crown measurements are optionally determined based on measuring a prepared tooth.

In some embodiments, a custom abutment is optionally designed based on measuring the gingiva surrounding an implant.

In some embodiments, the probe is used to validate drill work.

In some embodiments, the probe is used to choose an implant size, shape or type when drill holes in the bone are measured.

In some embodiments the measurements are used to prepare a periodontal chart.

In some embodiments, data from the probe is optionally added to a 3D model. In some embodiments, data from the probe is optionally added to a 3D model at model location where there is no data from other scanner(s) and/or to potentially refine and/or improve accuracy of data from the other scanner(s).

In some embodiments the measurement is optionally done through blood 815 to a few points on the gingiva 807* or on bone (not shown) or a tooth, which can optionally be used to calculate position and/or orientation of the implant 809.

Figure 8O:
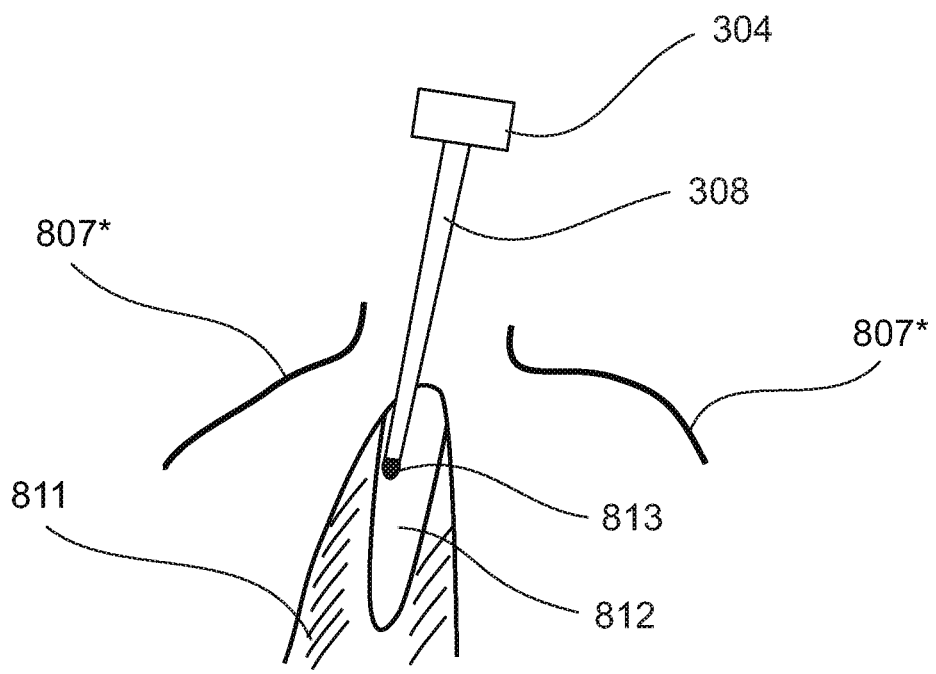
FIG. 8O is a simplified illustration of an IOS measuring a hole made by a drill in accordance with some embodiments of the invention.

FIG. 8O is a simplified illustration of an IOS measuring a hole made by a drill in accordance with some embodiments of the invention.

FIG. 8O shows gingiva 807*, bone 811 and a hole 812 in the bone 811, and an IOS head 304 and probe 308.

FIG. 8O shows the IOS head 304 measuring the hole 812, for example a hole 812 made by one or more of various drill(s) in a drilling process before an implant is inserted. By way of a non-limiting example, the probe 308 optionally measures one or more of a depth of the hole 812, a width of the hole 812, a shape of the hole 812 and an inside threading made by the drill.

In some embodiments the measurements are optionally compared to a desired result corresponding to an implant planned for use and its geometric parameters.

In some embodiments, an optional ball 813 at a tip of the probe 308 optionally has a diameter which is desired for an implant, and potentially enables verifying that the hole 812 is wide enough for the desired implant.

In some embodiments the measurements are optionally used to measure drill holes prior to implanting an implant, to verify that a drill has reached bone and produced a hole of suitable width, depth, shape, and thread.

Figure 8P:
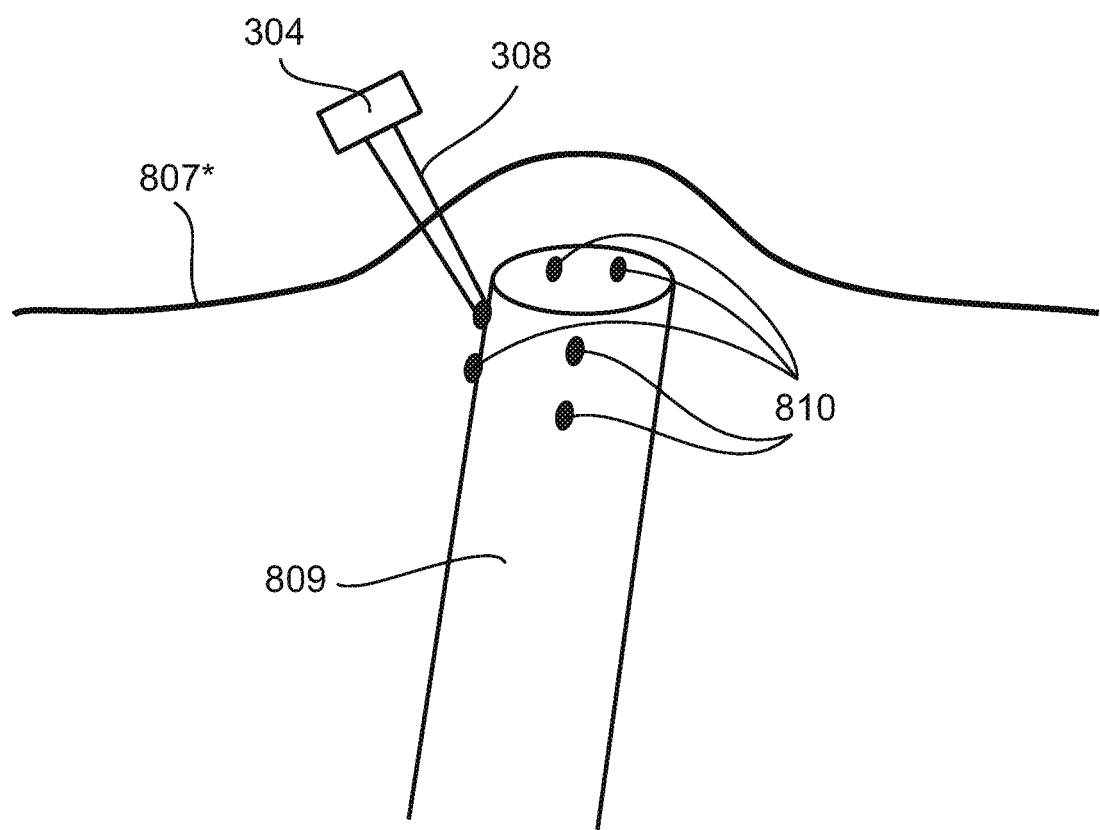
FIG. 8P is a simplified illustration of an IOS measuring parameters of a dental implant in accordance with some embodiments of the invention.

FIG. 8P is a simplified illustration of an IOS measuring parameters of a dental implant in accordance with some embodiments of the invention.

FIG. 8P shows an IOS head 304 using a probe 308 measuring parameters of a dental implant 809.

Example parameters measured by the probe 308 include, by way of some non-limiting examples, a location of the dental implant 809, orientation of the dental implant 809, shape of the dental implant, and similar geometric parameters, optionally relative to adjacent teeth (not shown), and/or relative to a jaw bone and/or relative to gums.

In some embodiments the measurement is optionally done using a number of known point 810 locations on the implant 809.

In some embodiments the number of known points 810 is optionally small, for example 6. In some embodiments, 6 known points 810 in a scan are optionally enough to produce a three-dimensional model and correctly register the model relative to a mouth with 6 degrees of freedom (DOF).

In some embodiments the spatial registration optionally gives up a DOF, for example rotation around a long axis of the implant 809 and 5 known points 810 are optionally used.

In some embodiments 3 known points 809 are used on an implant

In some embodiments a hollow cavity shape (not shown in FIG. 8P) represents the known points, providing a position and optionally an orientation vector for registration.

In some embodiments a hollow cavity shape (not shown in FIG. 8P) represents the known points, providing a position and optionally an orientation vector for registration and an addition known point is used in the registration.

In some embodiments the number of points is selected to enable determining a specific shape of an implant 809 that are enough in order to know the parameters due to the implant synthetic shape.

In some embodiments the known point 810 locations are optionally any touching point on an implant.

In some embodiments 3 known points are optionally marked on an implant. In some embodiments the 3 known points marked on the implant are not all on a straight line. In some embodiments data regarding the relative positions and/or distance between the 3 known points is known, optionally provided by an implant manufacturer. In some embodiments the probe is moved to make contact with the 3 known points, the known points are identified, and the implant is optionally registered in space and/or located with a model of the oral cavity based on knowing the size and shape of the implant relative to the locations of the 3 known points.

In some embodiments the implant is manufactured with probing holes at known locations on the implant. When the probe contacts the probing holes, the orientation and/or location of the implant is optionally calculated. by way of a non-limiting example, a 1 mm distance between 2 points can mean that the 2 points are the points at 12 o'clock and 3 o'clock of the implant (for example this is how the implant was manufactured) and a 2 mm distance between 2 points means that the 2 points are points at 3 o'clock and at 8 o'clock, for example.

In some embodiments the known point 810 locations are optionally configured so that a distance between the locations is greater than N pixels in an image or scan of the locations. In some embodiments the number of pixels N is greater than 2 pixels, or greater than a number N in a range between 2 and 5,000.

Figure 9:
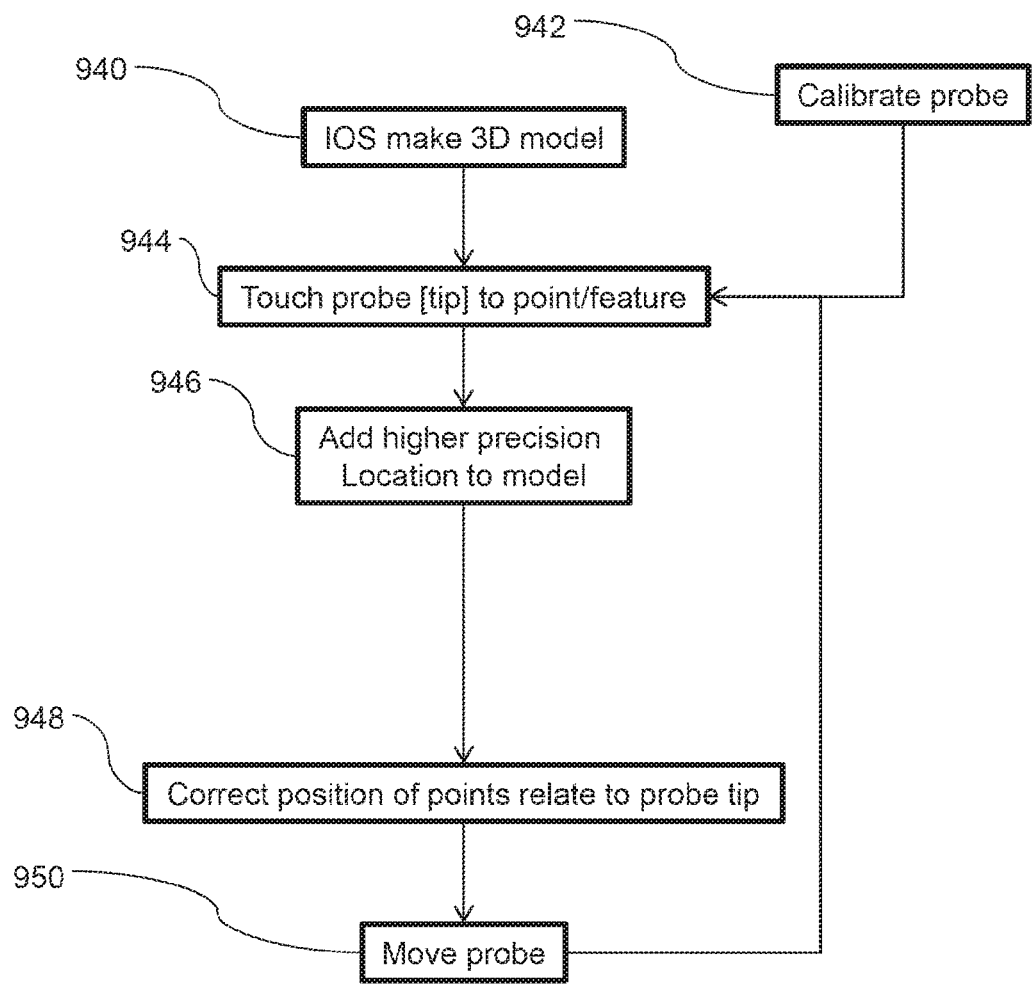
FIG. 9 is a flowchart of a method of improving IOS mapping accuracy, in accordance with some embodiments of the invention.

FIG. 9 is a flowchart of a method of improving IOS mapping accuracy, in accordance with some embodiments of the invention. In some embodiments, the IOS is used to make an initial 3D model 940 of a feature and/or a portion of the mouth and/or of the whole mouth. Optionally, the probe is used measure 944 at a higher accuracy the feature and/or a sub-region of the mapped area and/or another area. The high accuracy measurement is optionally added 946 to the 3D model. In some embodiments, the high accuracy measurement may be used to correct 948 the location of other points in the model at improved accuracy. Optionally, the probe may be moved 950 and/or further points may be measured 944 as needed. Optionally, the probe may be calibrated 942, before during and/or after scanning.

In some embodiments, an IOS scanner with a probe may be used to determine a locations and/or shape of a surface. For example, the probe may be used to touch 944 a point on the surface and/or the precise position of the point touched by the probe may be used to correct 948 the position of the surface. Alternatively or additionally, the probe may be touched 944 to multiple points on the surface and/or dragged across the surface and/or the points may be added 946 to build a high precision 3D model of the surface. For example, the surface may be modelled as a plane and/or a curve. In some embodiments, multiple points may be defined on the surface (for example by touching 944 each point with the probe). The distance between the defined points may be used to define a measure and determine distance along the surface and/or in other parts of a 3D model. In some embodiments, a fiducial marker (for example the tip of the probe) may be placed on the surface. The precise distance measure of the marker is optionally used to determine distances on the surface and/or to produce a high precision model of the surface and/or to correct 948 the locations of other points to a high precision.

In some embodiments, a calibrated probe is combined with a 3D camera. For example, the accuracy of the measurements done with the probe may significantly exceed the initial accuracy of the 3D scanner. Optionally, a processor runs an algorithms that finds the probe location from the scanner location in at least one 3D frame. For example, the probe location can be obtained from many 3D points and/or features measured by the scanner in the same frame.

For example, many IOS produce depth maps, for instance using structured light, and/or by aligning multiple images together to get a single 3D model. A typical accuracy of a point on a tooth in a model produced by an IOS is for example approximately 30 um. However the overall accuracy of alignment of a single depth map image that contains thousands of points to a 3D model may be significantly better. For example, the accuracy of the probe tip with respect to the rest of the model may be 10 μm instead of 30 μm. In some, embodiments this internal alignment of the probe measured point to the rest of the model may increase the accuracy of large areas on the model to within 10 μm.

In some embodiments, an IOS with a probe may be used measure a tooth prepared for fixed prosthesis (for example a crown for example as illustrated in FIG. 8F and/or an inlay for example as illustrated in FIG. 8B and/or an onlay for example as illustrated in FIG. 8C). For example, the IOS may be used to make 940 an initial 3D model of prepared tooth and/or the area around the prepared tooth. The probe is optionally brought in contact with areas of the prepared tooth (for example as illustrated in FIG. 8F). For example, the probe may be used to measure the extent of the shoulder and/or the edges and/or cusps of the prepared tooth. Alternatively or additionally, the probe may be used to measure closure between a prepared tooth and an antagonistic tooth. The high accuracy measurements are optionally used to prepare a more precisely crown, for example a crown that will better fit the prepared tooth and/or better mesh with an antagonistic tooth.

In some embodiments, the data from the probe combined with the data from the camera may be used to improve the accuracy of an STL file. For example, accurate locations of multiple points in a single depth mapped image may be computed based on their relationship to sample points in the image that were touched by the probe and/or measured using the probe. The accurate locations may be added to the STL file and/or used to correct the STL file.

In some embodiments, the data from the probe is optionally combined with data from a prior art dental scanner. In that case, the measurements from the probe are optionally combined with the measurements of the prior art scanner. In that way, the prior art scan can provide additional data, for example from areas that were not scanned an embodiment of the present invention, or not scanned well enough. Problematic areas that can be scanned with the probe embodiment and that are hard to get using a prior art scanner can be, by way of some non-limiting examples, deep holes like a hole inside an abutment or a space between two adjacent teeth, especially below a finish line of a crown.

In some embodiments, the sample points may be on supragingival areas that are seen by the camera and were measured with the probe (for example as illustrated in FIG. 3A-3F, 8F, 8G, 8C). Optionally, a portion of the probe (for example the probe tip and/or graduations along the probe) may be used as a fiduciary marker. For example, by imaging a scaled object on the probe, the scale of an image from the IOS may be made more precise. In some embodiments, improved scaling on the IOS image will allow determining more precise geometric relationships between features and/or higher accuracy location of features. Optionally, a probe tip may be dragged along a surface, for example to measure a line along the surface and/or to get an accurate measure of the roughness of the surface.

In some embodiments, a IOS scanner with a probe is used to measure a surface for placement of an onlay. In some embodiments an onlay implant or graft is fixed to the bone with pins/screws, for example to obtain primary fixation. For example this may be used in cases where there is not enough volume of bone for the conventional implant and/or where the dentist decides not to use augmentation procedure surgery. In some embodiments, an onlay will be produced via 3-D printing. For example, printing of titanium or CoCr using laser sintering. In some embodiments, data to produce the implant is obtained from a CT scan of the bone. Optionally an IOS scanner including a probe in accordance with an embodiment of the current invention may be used to produce a precise STL file of the outer surface selected to be underneath the onlay, for example a surface of the bone. Optionally, the data from the STL file is combined with the data from the CT scan to raise the accuracy of the final STL file. The combined CT, STL data is optionally used to determine the location and/or the size of the prosthesis and/or fixating screws of the prosthesis. In some embodiments, the IOS scanner probe in these cases will enable to produce a more accurate prosthesis. In some cases an onlay will be mounted to exposed bone or tooth, for example measurement may be similar to a crown described above. Alternatively or additionally, an onlay will be fitted to parts of a bone or tooth that are obscured. For example, measurement for such an onlay may be similar to measurements for an implant. In some embodiments, a CT and/or a STL file will be sent to a manufacturer who will produce the onlay and send it to the dental practitioner. In some cases data from a IOS scanner will be sent directly to an on-site 3D printer. For example, on-site printing or CNC may make it possible to reduce the time and/or number of dental visits for producing an implant and/or onlay.

In some embodiments, an IOS scanner with a probe may be used to measure a plaque layer or calculus, for example as illustrated in FIG. 8H. For example, the probe may be used in conjunction with the IOS sensor to locate and/or measure and/or evaluate exposed plaque deposits. Alternatively or additionally a probe may be used to explore a periodontal pocket for example to determine the depth of the pocket, for example as illustrated in FIG. 8A and/or FIG. 13A and/or FIG. 13B. Alternatively or additionally, the probe may be used to locate, measure and/or evaluate plaque deposits under the gum line. For example, the tip of the probe may be dragged along an obscured surface. For example, the presence of scales may be revealed by changes in roughness of the surface that are apparent in the 3D map made based on images of the position of the probe as it passes along the surface. Alternatively or additionally, a sensor may be provided near the tip of the probe. Optionally, the probe tip and/or sensor may be inserted into the periodontal pocked. For example, the sensor data may be used to locate, measure and/or evaluate a plaque deposit. For example, the IOS sensor may be used to evaluate the depth to which the probe is inserted in a periodontal pocket and/or the scale of movements as a probe is dragged along a surface. Optionally an IOS sensor may be used to determine a location of a probe (for example the IOS may sight and/or locate an exposed part of the probe, the location a concealed part of the probe and/or a sensor on the probe may be calculated for example based on the location of an exposed portion of the probe and the geometry of the probe). The sensor on the probe is optionally used to evaluate a concealed feature, for example including a subgingival deposit.

In accordance with some embodiments of the current invention, an IOS scanner and probe may be used to detect measure and/or evaluate tooth abrasion, for example as illustrated in FIG. 8E. In some embodiments a probe may be fitted with a gauge to measure deposits of scale and/or plaque. For example, a gauge may include an ultrasonic range finder. Optionally, deposits may be measured above the gum line (supra gingival) and/or below the gum line (sub gingival). Measurement techniques listed above with respect to plaque may be applied to measure abrasion and/or scale deposits. Alternatively or additionally, a probe may include an ultrasonic scaler. For example, a tooth may be measured and/or deposits may be evaluated. For example, the scaling may be directed using images of the IOS while the probe is being used to remove the deposits. For example, IOS images and/or other sensor data may be used evaluate the progress of the scaling.

Figure 10:
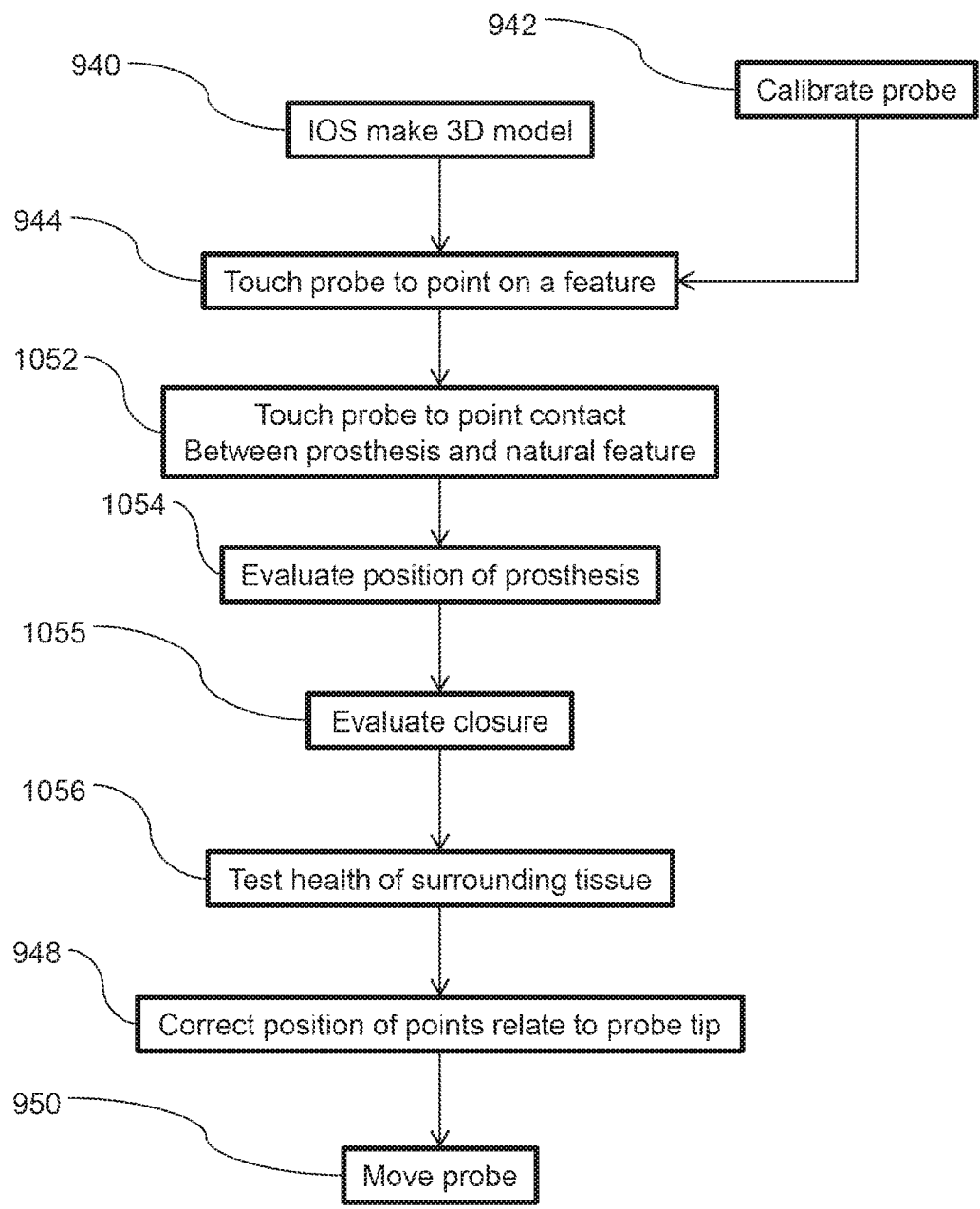
FIG. 10 is a flowchart of a method of intraoral mapping for an artificial object, in accordance with some embodiments of the invention.

FIG. 10 is a flow chart illustrating post placement measuring of a prosthesis in accordance with an embodiment of the current invention. In some embodiments, a probe may be used to increase accuracy of measurement of the location and/or fit of a the prosthesis. For example, the probe tip may be placed in contact with the prosthesis and/or dragged along a surface of the prosthesis, for example to determine an exact location of the feature. For example, the probe (and/or a tip thereof) may be placed on 1052 and/or dragged along a joint where a prosthesis contacts a native structure. For example, the fit of the prosthesis at the joint (for example a finish line of a crown) may be evaluated and/or the placement of the prosthesis may be evaluated 1054, for example as illustrated in FIG. 8G. While the fit of the prosthesis is being measured, the location of the probe may be determined using IOS images and/or by matching features in an STL file, This may improve measurement of the location of mismatched features of the prosthesis and the native structure. Optionally, the probe may be used to evaluate 1055 closure and/or positioning of prosthesis (for example a crown) with respect to antagonistic teeth. Measurements are optionally made of exposed features and/or caught in the IOS image (for example when testing the positioning of a crown and/or overlay). Alternatively or additionally measurements may be made of fit of concealed features, for example the matching of an implant and/or an extraction cavity. Optionally, measurements of concealed objects are made while touching the object with a probe and/or using a probe mounted sensor.

In some embodiments, the height of a prosthesis may be evaluated 1054 and compared to an expected height, for example to determine if the prosthesis was properly fit. Alternatively or additionally, a probe may be used to measure a feature of a prosthesis and/or a prepared location for placement of the prosthesis. For example, a thread width of a screw thread and/or matching of threads may be measured in situ.

In some embodiments a IOS with a probe may be used to measure features of a man-made element itself (for example size, surface quality of a prosthesis). Alternatively or additionally, the IOS with a probe may be used to measure the placement of the man-made element with respect to a natural element (for example bone, teeth, gingiva, etc.) and/or with respect to other man-made elements. For example an IOS with a probe may be used to measure a dimension on an inlay and/or the insert height of an implant to the bone.

Figure 11:
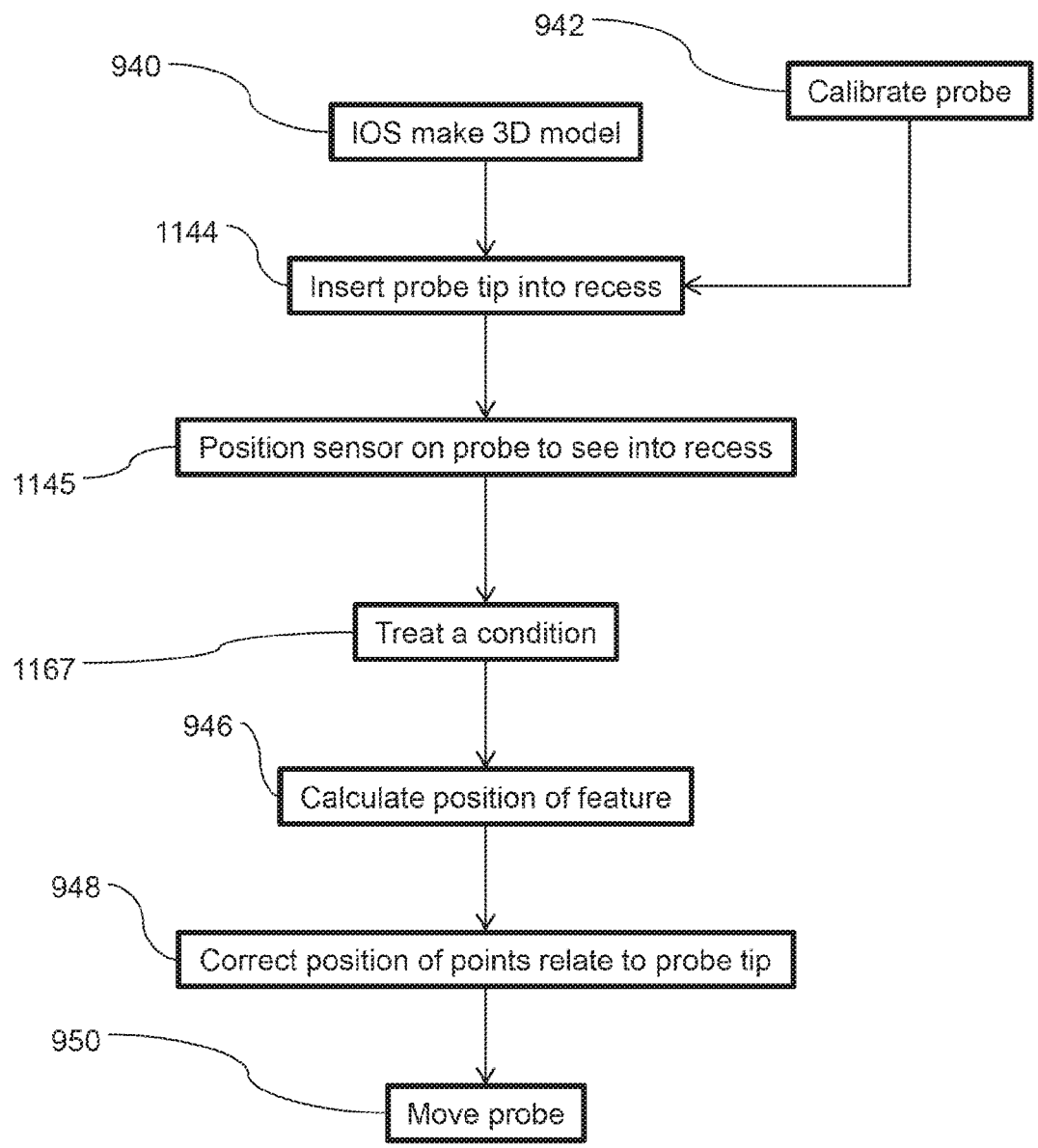
FIG. 11 is a flowchart of a method of intraoral mapping a recess, in accordance with some embodiments of the invention.

FIG. 11 is a flow chart illustration of a method of measuring a recess in an oral cavity with an IOS including a probe in accordance with an embodiment of the current invention. In some instances, the inside of the recess may be obscured from an IOS scanner. In some embodiments a probe may be inserted 1144 into a recess and/or contact points in the recess, for example to measure a location on the walls of the recess and/or depth of the recess 8D. Alternatively or additionally, a sensor and/or light source on a probe may be positioned 1145 to get a better view of the recess, for example as illustrated in FIG. 8B. For example, the sensor 1145 of the probe may be positioned to view a recess from outside the recess. Alternatively or additionally the sensor may be inserted 1144 into a recess to view from the inside (for example inside a periodontal pocket as illustrated for example in FIG. 8F.

In some cases, a prosthesis, for example an implant and/or an inlay and/or an onlay, may be inserted 1144 into a recess. For example, the prosthesis may be inserted 1144 into a recess in a tooth and/or into a recess in a bone and/or into a recess in the gingiva. For example the probe may be used to measure a post extraction socket, for example as illustrated in FIG. 8D. Optionally, measurement data may be stored and/or sent to a manufacturer when ordering the prostheses. Alternatively or additionally, data from the measurements may be sent directly to a 3D printer to produce prosthesis. For example, the prosthesis may be printed on-site and/or in real time. For example, a dentist may measure and place prosthesis. For example the scanner may include a processor and/or a network adaptor allowing it to directly communicate with a printer.

In some embodiments, a probe may be inserted 1144 inside of a recess to measure the recess and/or determine a health condition and/or treat a health condition. For example a probe may be used to explore and/or clean a root 863 for example as illustrated in FIG. 8I. For example, the probe may be used to measure root apex depth. Optionally, a probe of an IOS may perform 1167 a treatment. For example a probe for probing a root may include a channel. For example the channel may be used to sterilize the root (for example by introducing a chemical and/or by heat or a laser) alternatively or additionally a channel may be used to apply a vacuum to clean the root. Optionally the IOS may be used to map the location and/or evaluate the effect of the treatment.

For example, an embodiment of the current invention may be used to characterize the shape of a post extraction socket in the bone to prepare an exact fitting implant, For example, the root of a tooth may be engaged in the alveolar bone. After extracting the tooth and/or root, a cavity may remain in the bone. The cavity may be referred to herein as a "socket". The anatomy of the socket may correspond to the root that was previously held in it.

In some embodiments, measurements and/or a 3D map and/or 3D printed prosthesis may be produced quickly using an embodiment of the current invention. For example the pre preparation measurement of the bone and/or 3D map quickly enough to leave the dentist free to prepare that bone in the same sitting. Alternatively or additionally, after preparing the bone, a post preparation map of the bone may be made at the same sitting. and/or design for the prosthesis may be made in the same sitting. Alternatively or additionally, after preparing post preparation measurement of the bone production of the prosthesis (for example by 3D printing) and/or attaching of the prosthesis may be done in the same sitting. In some embodiments, using an embodiment of the present invention the number of sitting required to measure, prepare, produce and/or attach a prosthesis may be reduced. Optionally this shortens the time and/or cost of installing a prosthesis.

Some dental implants may be limited to a cylindrical shaped. In some cases, the cylindrical shape will not correspond to the socket anatomy which may for example be conical shaped. In case of multi rooted tooth such as a molar there may be a more significant discrepancy between the socket and a conventional prosthesis. Placing such an implant may include drilling and/or augmenting the bone. to produce a properly shaped socket for mounting the implant. In accordance with an embodiment of the current invention measuring of a socket and/or production of a custom insert is facilitated. In accordance with an embodiment of the current invention measuring of a socket and/or production of the insert is facilitated.

In some cases, a bone has appropriate height, but has insufficient width to receive a conventional implant. Optionally, a dentist and/or a surgeon can create a cavity in the bone, for example resembling a groove along the bone. Optionally, before creating the cavity in the bone, a 3D map giving precise information about of the shape of the bone may be obtained using an IOS with a probe, for example to produce a 3D map. For example, a surgeon may use the 3D map to plan where and/or how to connect the onlay to the bone. For example, the 3D map may be used to determine where there is sufficient bone to connect to the onlay and/or what kind of connection is possible between the onlay and the bone. For example, a surgeon may use the 3D map to plan where to form the groove and/or what size to make the groove and/or what shape to make the groove.

In some embodiments a 3D map of the bone will be prepared using an embodiment of the present invention after the bone has been prepared. For example, the 3D file obtained by the probe and scanner may be used to produce an implant that precisely fits the outer surface of the bone and/or precisely fits into the groove. In some embodiments, the current invention facilitates production and/or fitting of a custom onlay that fits on the outer surface of the bone and/or a natural cavity and/or a cavity drilled by the dentist. For example this may enable the dentists to use an onlay in compromised bone conditions without bone augmentation and/or with less augmentation than conventional procedures. The custom prosthesis may be attachable to bones that were not able to support a conventional implant and/or a custom implant may be more stable than a conventional implant.

In some embodiments, using the probe and the scanner may facilitate immediate implantation. High accuracy mapping may improve primary fixation in some embodiments. For example, using a precisely fit and/or custom made prosthesis, surgery may be less complicated and/or less technical sensitive and/or suitable for less trained and experience dentists. Using an IOS probe combination may eliminate the need to augment the bone. In some cases this will lower the price of the surgery and/or reduce the side effects (swelling and infections). Measurement of the socket at higher resolution with an IOS probe may in some embodiments produce a better fitting prosthesis and/or eliminate the need to drill into bone for example to fit the prosthesis. Optionally, elimination of the need to drill into the bone will give the dentist the opportunity to have a more conservative surgery and/or lower the chances to harm other tissues for example nerves and sinuses. For example, a reduced time and primary fixation procedure may replace a multi-step implantation process that would require 6-8 weeks of recovery after the tooth extraction, in order for the socket to heal and be ready for the surgery of implant insertion.

In some cases, inserting the implant may include primary fixation of the implant in the bone. In some embodiments, an IOS with a probe is used to characterize the shape of a post extraction socket in the bone. For example, STL file, obtained from the scanner, can be exported to create an well-fitting implant to the anatomy of the socket. For example, the IOS with probe may be used to map multiple cavities in a socket of a multi-rooted tooth. Creating a well-fitting implant is optionally done via 3D printing. The resulting implant is optionally attached to the bone with reduced preparation of the bone, for example without drilling.

Using the probe optionally facilitates immediate implantation in some cases. For example this may shorten the time needed between the extraction of the tooth and delivering the final prosthesis and/or reduce the number of surgical procedures. In some embodiments the above may result in faster, less costly procedures, more comfort to the patient and/or more simplicity to the dentist.

Figure 12:
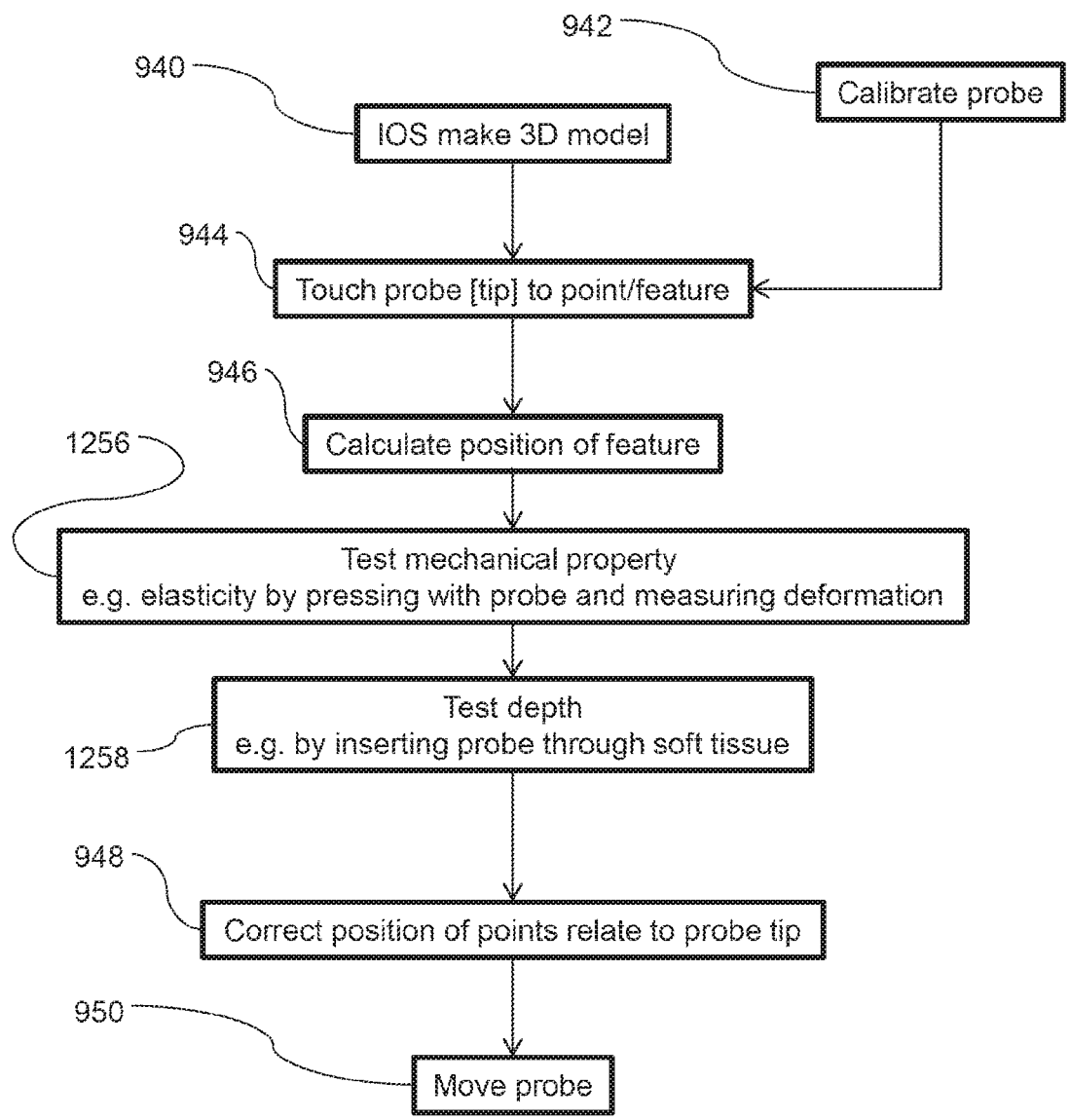
FIG. 12A is a flowchart of a method of intraoral mapping of soft tissue, in accordance with some embodiments of the invention.
FIG. 12B is a simplified illustration of a probe used as a feature in an IOS scan in accordance with some embodiments of the invention.

FIG. 12A is a flowchart of a method of intraoral mapping soft tissue in accordance with some embodiments of the invention. For example, an IOS including a probe may be used to map out the surface of the lining mucosa. This data may be used for producing and/or fitting a removable prosthesis, for example to treat edentulism.

In some embodiment, an IOS with a probe may be used to scan the oral mucosa. Scanning the mucosa may be challenging due to lack of features (for example when there are no teeth). In some embodiments, the probe, touching the mucosa can improve the ability to produce an STL file and/or improve its accuracy.

In some embodiments, the probe is optionally used as a feature which can be identified and located in an oral scan or map produced by the IOS.

In some embodiments the probe is optionally used as a feature in a map or scene with only few features, by way of a non-limiting example in a scan of a partially edentulous arch. The probe, touching the gingiva, is optionally used as a feature that the processing unit can use in order to create a model, potentially a more accurate model than previously.

In some embodiments the probe is placed at a stationary place while the scanner orientation is changed, to capture different areas around the probe. Such example embodiments potentially produce a more accurate model, optionally based on more features in a scene.

Figure 12B:
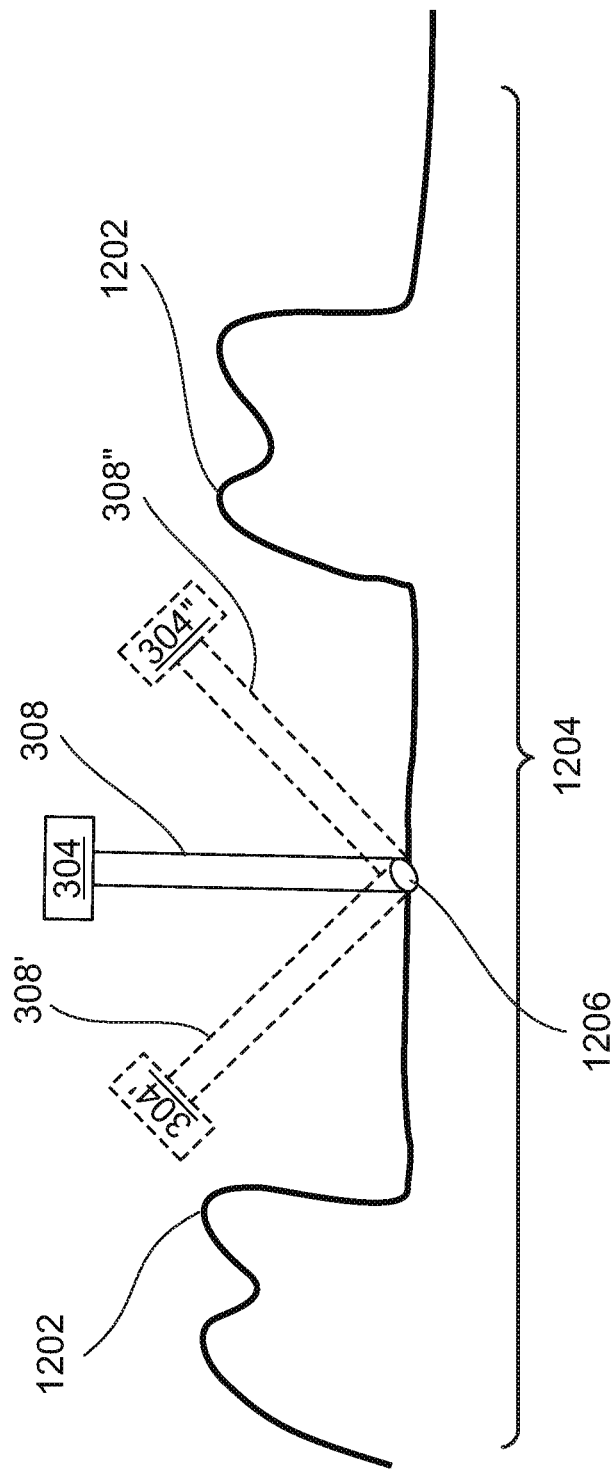

FIG. 12B is a simplified illustration of a probe used as a feature in an IOS scan in accordance with some embodiments of the invention.

FIG. 12B shows an IOS head 304 304' 304" and a probe 308 308' 308", and example teeth 1202 in an example intra-oral section 1204 to be scanned.

FIG. 12B shows the IOS head 304 304' 304" scanning the intra-oral section 1204 to be scanned from several angles, by way of a non-limiting example three angles as shown in FIG. 12B.

In some embodiments a tip 1206 of the probe 308 is optionally kept at one specific location in the intra-oral section 1204 to be scanned, and optionally provides a static position, enabling one method of identifying a same location in scans from the three angles.

In some embodiments other known features in the three scans, for example the teeth 1202, are optionally used to identify same location(s) in scans from the three angles.

In some embodiments the IOS head 304 is manipulated to move between the three positions 304 304' 304". The 3 positions are optionally used, by way of a non-limiting example, to capture image(s) of a first tooth 1202 and a location of the probe tip 1206, then optionally to capture image(s) of the probe tip 1206, then optionally capture image(s) of the probe tip location 1206 and a second tooth 1202.

In some embodiments known locations of the first tooth 1202 and the second tooth 1202 are optionally used to correctly register a location of the probe tip 1206 relative to the teeth 1202.

In some embodiments, once locations of the first and the second tooth positions are registered relative to the same probe position, the location of the first and the second teeth are optionally also registered in a 3D model of the mouth.

In some embodiments, an IOS for mapping the surface of the lining mucosa the probe has an enlarged tip 372. For example, tip 372 may be formed into a sphere with large diameter for example in the range of 1-5 mm and/or 5-10 mm and/or 10-20 mm. Alternatively or additionally a sphere may be mounted on tip 372. The sphere may facilitate better mapping of the surface of the lining mucosa features which are relevant for removable prosthesis good fit. Optionally, widened tip may be made out of steel and/or hard rubber and/or plastic.

In some embodiments a physical property of the tissue may be tested 1256. For example, the elasticity of the surface of the lining mucosa is measured 1256 or mapped. Optionally, the surface of the lining mucosa is scanned with said probe. For example, scanning may include applying low force with the probe during scan of the surface of the lining mucosa and or measuring 1256 the deformation of the surface. For example the applied force may range between 0.001 to 0.1 Newton and/or between 0.01 to 0.1 Newton and/or between 0.01 to 0.1 Newton and/or between 0.1 to 1 Newton.

In some embodiments, the applied force may be measured from the probe deflection. Alternatively or additionally, the applied force may be measured using force sensor on the probe (for example as illustrated in FIGS. 3D-3F). The deformation of the tissue as the sphere is pushed into the surface of the lining mucosa may be measured, for example, using the 3D scanner. From the combination of the deformation of the tissue and the applied force the elasticity can be computed. In addition, The vitality of an area may be measured, for example using the flow of the blood out and into the area when applying and removing the force. The changes in the blood supply is optionally measured using the camera to capture changes in color due to the changes in the quantity and/or pressure of blood present. Alternatively or additionally, a depth of soft tissue may be measured 1258. For example, a sharp probe may be pushed through soft tissue until it reaches a hard feature (for example bone or tooth). The depth of penetration can then be recorded as the depth of the tissue. Optionally, the resistance to penetration of the tip may be measured.

Figure 13A:
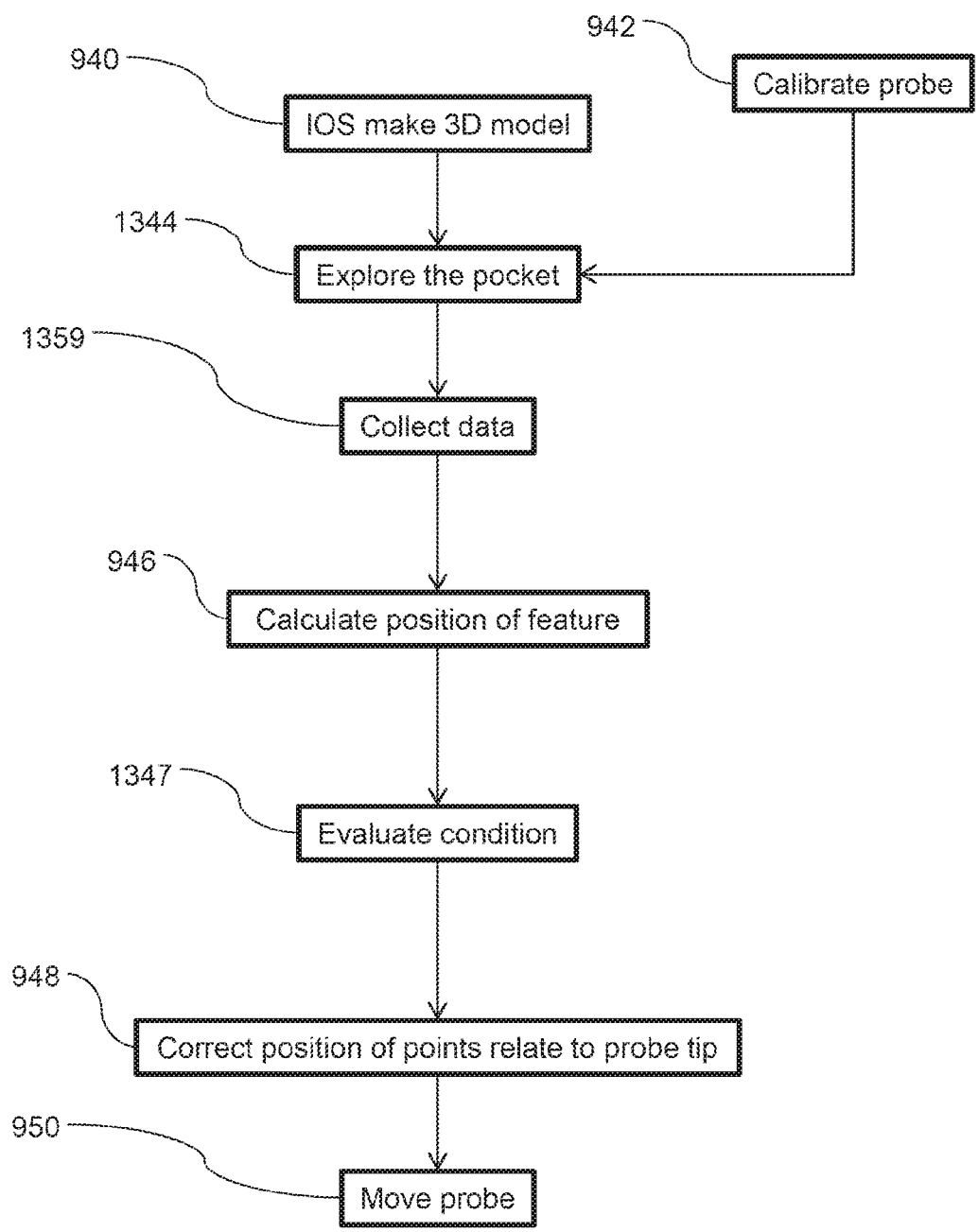
FIG. 13A is a flowchart of a method of intraoral mapping of a periodontal pocket, in accordance with some embodiments of the invention.
Figure 13B:
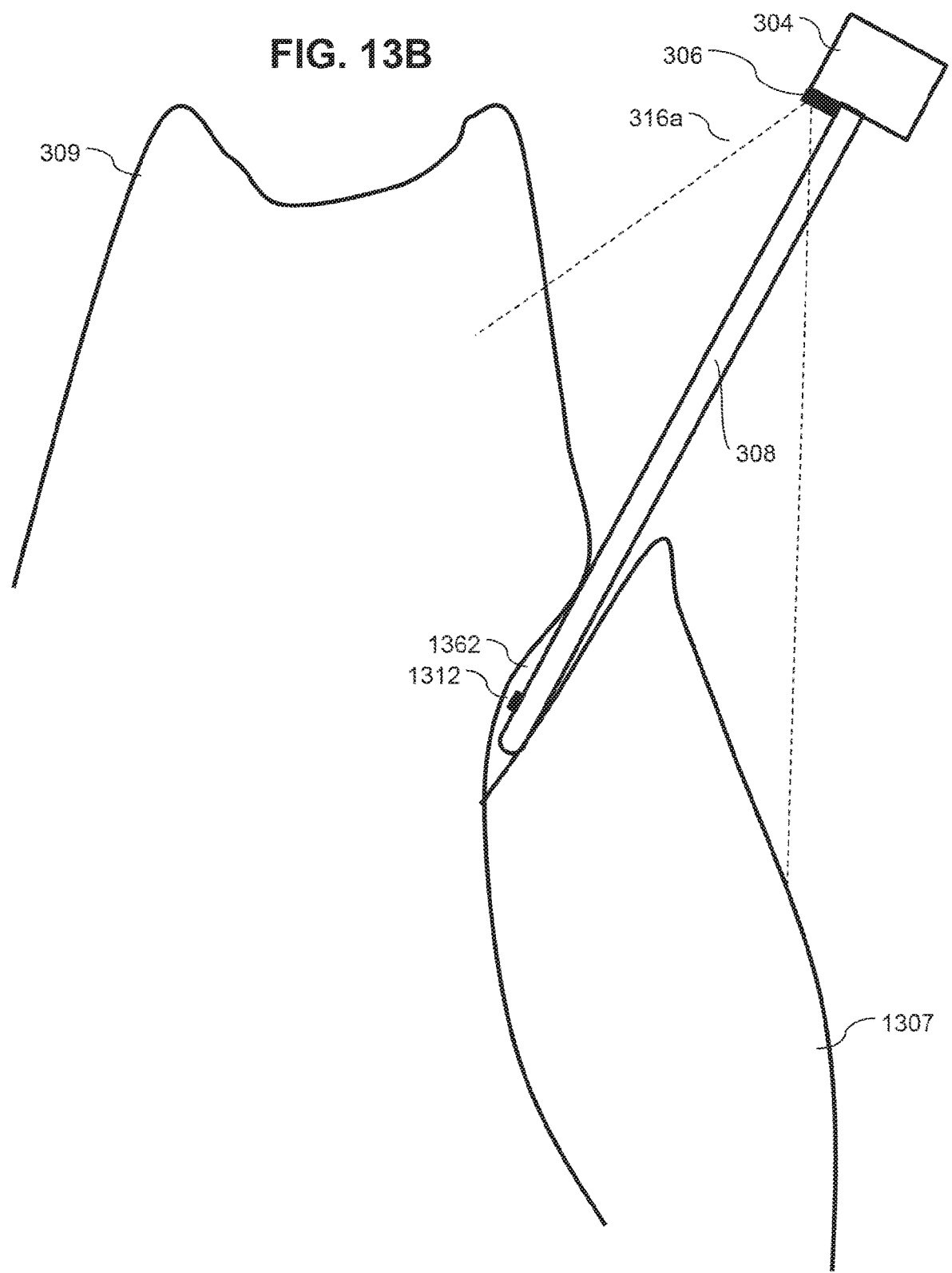
FIG. 13B is a schematic showing of a side-looking IOS in a periodontal pocket, in accordance with some embodiments of the invention.

FIG. 13A is a flow chart illustrating use of a IOS including a probe to explore a periodontal pocket in accordance with an embodiment of the current invention. In some embodiments a probe will be inserted into a periodontal pocket. Optionally the pocket will be explored 1344 using the probe. Optionally, data will be collected 1359 from the IOS and/or probe mounted sensors. The 3D location of the probe and/or areas being explored is optionally calculated using the IOS. Optionally, data and position information will be used to evaluate 1347 periodontal health. In some embodiments, data will be collected 1359 from a probe based sensor (for example an optical sensor 1312 as illustrated for example in FIGS. 13B, 3A-3C and/or a force sensor for example sensors 322a-322c as illustrated in FIGS. 3D-3F and/or a remote sensor for example an external x-ray imager and/or an external sensor connect to the probe for example through an optical fiber as described for example in relation to FIGS. 5A and 5B)

In some embodiments, during exploration 1344 the probe may be inserted to the end of the pocket. Optionally, the IOS will image an exposed portion of the probe, for example extending out of the pocket and/or the IOS will calculate 946 the position of the probe and/or depth of the pocket may be measured.

In some embodiments, the probe will be used to exert pressure on an object. Optionally, the IOS may collect 1359 data about the movement of the object and/or tissue and/or teeth due to forces exerted by the probe. For example, pressure may be exerted on an object inside the periodontal pocket. Alternatively or additionally, data about the force exerted by the probe on an object may be collected 1359 using force sensors on the probe (for example as described with respect to FIGS. 3D-3F) and/or the IOS may collect 1359 data on bending of the probe (for example from images of the probe) the force exerted is optionally calculated based on bending of the probe apparent from IOS images. Optionally, periodontal health will be evaluated based the position of probed objects, the size of the pocket and/or the stiffness and/or softness of teeth and/or other tissue.

Figure 14:
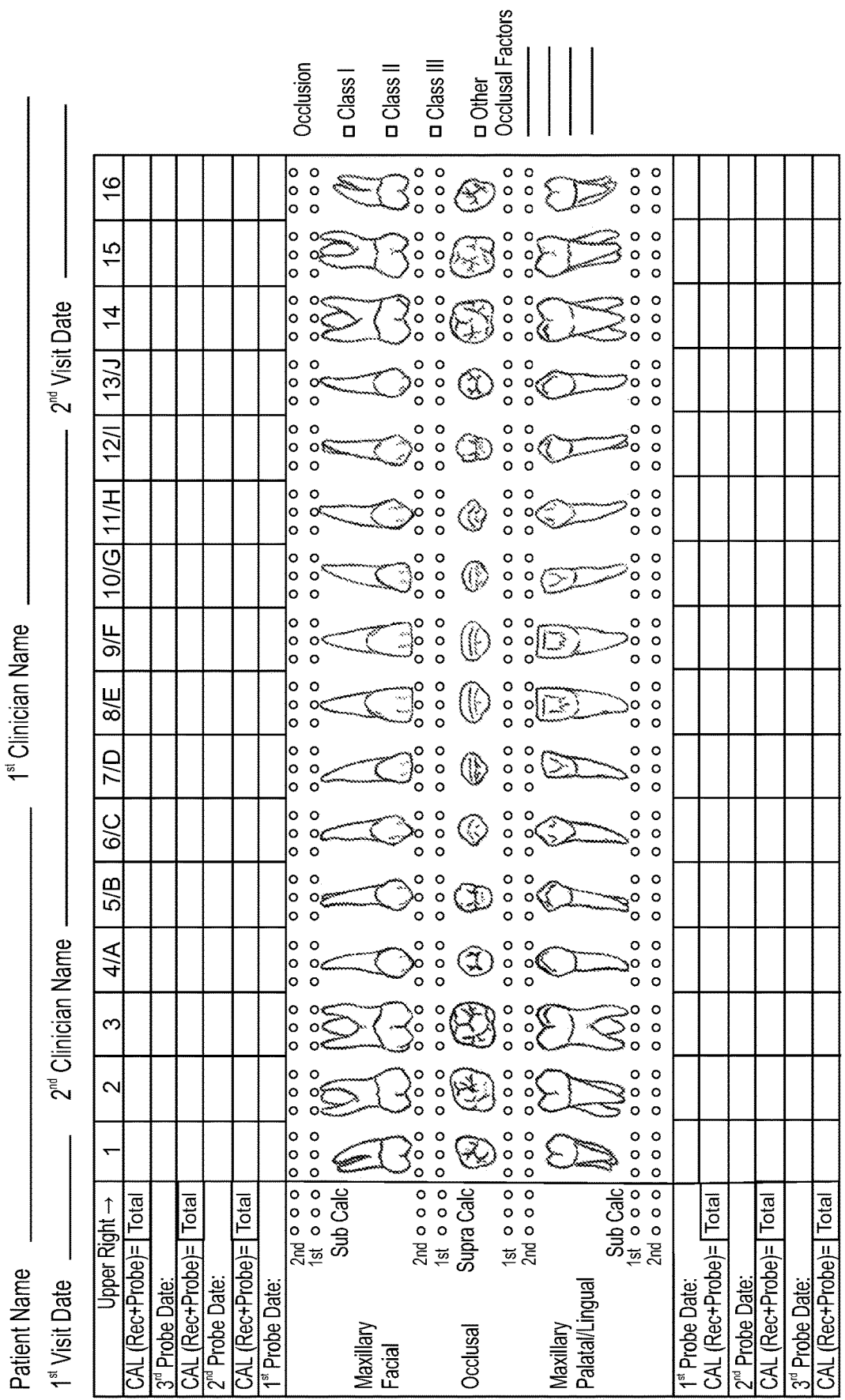
FIG. 14 is a portion of a chart display optionally provided by periodontal imaging, in accordance with some embodiments of the invention.

In some embodiments, a sensor on the probe will be used to collect 1359 data on periodontal health. For example, the probe may include an optical sensor (for example sensor 1312 illustrated in FIG. 13B) near the tip thereof. For example the sensor may include, for example a large FOV imaging sensor and/or a small FOV sensor or the like. Alternatively or additionally, optical sensing at the tip may be via an optical fiber (for example through a channel as illustrated in FIG. 5A-5B) transmitting light to a remote sensor. The images may be evaluated 1347 to diagnose inflammation and/or bleeding (for example from the color of teeth and/or other tissue). Data from a sensor on the probe and/or from the IOS sensor may be used to locate a CEJ (cement to enamel junction) and/or a mukoginigival line for example based on the color difference. Optionally the position of measured features is calculated 946 and/or combined with a 3D model. The 3D data optionally is used to evaluate 1347 the location and/or extent of periodontal conditions. Alternatively or additionally, the 3D data may be used to output a personalized periodontal chart for example as illustrated in FIG. 14. The periodontal chart is optionally generated automatically.

In some embodiments, the probe may also be used to collect 1359 data and/or the IOS may be used calculated position 946 and/or map CAL (clinical attachment level/ loss). The probe may also be used to collect data 1359 on furcation involvement. The probe may also be used to collect 1359 data on subgingival plaque. For example plaque may be to identified and/or measured using fluorescence. For example, the probe may include optical fibers and/or probe mounted sensors and/or illumination sources to measure fluorescence.

In some embodiments full dental charting which lists and describes the health of teeth and gums is automatically produced.

In some embodiments, Periodontal charting includes one or more, and up to six measurements (e.g. in millimeters) that are taken around each tooth.

In some embodiments the charting is done during dental checkups, by the hygienist and/or the dentist.

In some embodiments the charting provides a graphic method of organizing and presenting information about a patient's dental health, i.e. it is a graphical tool for organizing information about teeth and gums.

In some embodiments the chart includes a graphical, or pictorial, representation of the patient mouth. In some embodiments the chart shows one or even all of the teeth as a real image, optionally using 2D or 3D graphics, optionally using color and/or shading.

In some embodiments the chart includes additional information on the condition of the teeth and gums, such as, for example: areas of decay (cavities), missing teeth, depths of the gum pockets, bleeding points during probing, gum recession, abnormalities in the teeth, such as rotations, erosion, or abrasions in the teeth or enamel, damage to the teeth, presence of crowns, bridges, implants, and fillings, attachment of the teeth to the gums, movement and/or mobility in the teeth, bleeding in the gums, exposed teeth furcation, presence of suppuration.

In some embodiments, the chart information is stored in a memory as a record, optionally in the cloud.

In some embodiments stored chart information is optionally compared to current chart information, for example during a dental checkup, potentially enabling progress of dental health to be tracked.

In some embodiments, the charting process optionally begins by finding a scanned tooth number so the measured parameters can be attributed to a correct scanned tooth. A hygienist and/or a dentist optionally examines the teeth, optionally by probing gums to check the depths of the gum pockets. In some embodiments up to six readings per tooth are recorded in the periodontal charting process.

In some embodiments the IOS automatically identifies the probing location around the tooth, and optionally display a pocket depth in the chart accordingly.

In some embodiments, if a tooth has mobility and moves during the probing, the IOS optionally identifies the mobility level and adds the mobility level to the chart.

In some embodiments, movement of a tooth is optionally obtained by applying force, optionally lateral force, to a crown area of the tooth, optionally with a tip portion of the probe, and measuring and/or calculating movement of the tooth relative to a model or to known points in an image and/or by measuring and/or calculating a bending of the probe.

In some embodiments, a color image obtained from the IOS is used for detection of parameters such as the CEJ, mucogingival junction, bleeding, suppuration, presence of crowns, bridges, implants, and fillings.

In some embodiments, a 3D model obtained from IOS with or without the addition of the probe information is optionally used for detection of tooth furcation and the free gingival line.

In some embodiments a clinical attachment level (CAL) is optionally automatically presented by calculating relevant data, such as, for example, pocket depth, free gingival line, CEJ, mucogingival line. Data from an X-ray image is optionally combined in a calculation, such as, by way of a non-limiting example, a length of a tooth and/or a root of a tooth.

In some embodiments, if some features are hidden by blood, for example furcation or CEJ, the probe is used to detect the feature, for example furcation, even in the presence of blood. The detection is optionally performed by touching the furcation with the probe, or by detecting the CEJ using a color difference between enamel and cement/ cementum in an image optionally captured, optionally by a fiber, optionally through the probe, optionally while air pressure clears a view between the fiber and the enamel and/or cementum.

FIG. 13B is a schematic illustration of a IOS including a probe 308 exploring a periodontal pocket 1362 between a tooth 309 and gums 1307. In some embodiments, a tip of a probe 308 will be used to explore a periodontal pocket 1362. Optionally, information gathered by the probe will be integrated with 3D mapping.

In some embodiments, the device may automatically compute pocket depth as a function of position. For example, the IOS may track the position of probe 308 over time and/or find the maximum insertion depth as a function of a 3D location and/or compute a spatial distribution of pocket depth. Alternatively or additionally, the user may signal to the IOS when probe 308 has reached the end of the pocket and/or reaching the end of a pocket may be registered by a pressure sensor.

In some embodiments a probe 308 may include a tool. For example, an optical sensor 1312 and/or a light source may be provided near the tip of probe 308. Optionally sensor 1312 is used to detect and/or identify periodontal features. In some, embodiments optical data gathered by sensor 1312 may be combined with data gathered by IOS sensor 306 to map features in 3D and/or to find relationship between exposed features and periodontal or unexposed features. FIG. 14 illustrates a periodontal chart. In some embodiments, an IOS with a probe will be connected to a processor and/or an output device that will automatically generate the table from sensor data and/or 3D IOS information. Optionally the processor will store a 3D map of dental features (for example teeth) and/or data on periodontal conditions and/or their locations. For example, as a dental practitioner probes periodontal pockets with the probe, a processor may store data on periodontal conditions. For example, periodontal conditions may be determined by the processor based on probe measurements and/or sensor measurements for example as described in the description of FIG. 13A, 13B. Optionally, the processor will determine the location of the measured condition based on output of the IOS sensor and/or in relation to a 3D map (for example an STL file). For example, the probe location when a particular condition was measured will be correlated with the locations of various teeth to determine the particular tooth and/or on particular face of the tooth on which the condition was measured. The probe location at the time of measurement is optionally detected by an IOS sensor and/or stored by the processor. The resulting correlation between dental structures and measured conditions may be output as a periodontal chart listing detected conditions and/or the location of the conditions on various intra-oral features for example as illustrated in FIG. 14.

It is expected that during the life of a patent maturing from this application many relevant IOS will be developed; the scope of the term IOS is intended to include all such new technologies for scanning and/or 3D reconstruction a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A dental probe comprising:
a body having a proximal end and a distal end; said distal end extending in a first direction;
at least one fixed imager configured for imaging in a second direction different from the first direction; and
a probe extending in the second direction and at least part of said probe is always within a field of view of the imager,
wherein:
the probe comprises an ultrasonic sensor component located at a distal end of said probe;
said ultrasonic sensor component located at a known fixed location in relation to said dental probe;
wherein:
said ultrasonic sensor is configured for scanning lateral to said probe; and
wherein said ultrasonic sensor comprises a size configured to allow the insertion of said distal end of said probe in a subgingival area.

2. The dental probe of claim 1, wherein the ultrasonic sensor comprises an ultrasonic distance sensor.

3. The dental probe of claim 1, wherein the ultrasonic sensor comprises an ultrasonic imager.

4. The dental probe of claim 1, wherein the probe comprises a side viewing ultrasonic imager (IVUS).

5. The dental probe of claim 1, wherein the probe comprises a Piezoelectric Micromachined Ultrasound Transducer (PMUT) array.

6. The dental probe of claim 1, wherein the probe includes a channel for dispensing acoustic coupling liquid.

7. The dental probe of claim 1, wherein the probe includes a mechanical contact sensor.

8. The dental probe of claim 1, wherein the ultrasonic sensor includes a plurality of sensors.

9. The dental probe according to claim 1, wherein, the probe includes an ultrasonic scaler configured for removing plaque, and wherein the imager is configured to determine if said plaque was removed by said ultrasonic scaler.

10. The dental probe of claim 1, wherein the probe is a quick release component configured for quick release from the body.

11. The dental probe of claim 10, wherein the quick release is configured for releasing using a dentist tool.

* * * * *